United States Patent
Sun et al.

(10) Patent No.: US 11,024,424 B2
(45) Date of Patent: Jun. 1, 2021

(54) COMPUTER ASSISTED CODING SYSTEMS AND METHODS

(71) Applicant: Nuance Communications, Inc., Burlington, MA (US)

(72) Inventors: Weiyi Sun, Medford, MA (US); Ravi Kondadadi, Rosemount, MN (US); Brian William Delaney, Bolton, MA (US); Girija Yegnanarayanan, Raleigh, NC (US)

(73) Assignee: Nuance Communications, Inc., Burlington, MA (US)

( * ) Notice: Subject to any disclaimer, the term of this patent is extended or adjusted under 35 U.S.C. 154(b) by 548 days.

(21) Appl. No.: 15/796,658

(22) Filed: Oct. 27, 2017

(65) Prior Publication Data
US 2019/0130073 A1    May 2, 2019

(51) Int. Cl.
| | | |
|---|---|---|
| *G16H 50/20* | (2018.01) | |
| *G16H 10/60* | (2018.01) | |
| *G16H 50/70* | (2018.01) | |
| *G16H 40/20* | (2018.01) | |
| *G06K 9/62* | (2006.01) | |

(Continued)

(52) U.S. Cl.
CPC ............ *G16H 50/20* (2018.01); *G06F 40/30* (2020.01); *G06K 9/6223* (2013.01); *G06K 9/6263* (2013.01); *G16H 10/60* (2018.01); *G16H 40/20* (2018.01); *G16H 50/70* (2018.01); *G06N 20/00* (2019.01)

(58) Field of Classification Search
None
See application file for complete search history.

(56) References Cited

U.S. PATENT DOCUMENTS

| 4,696,039 A | 9/1987 | Doddington |
|---|---|---|
| 5,031,113 A | 7/1991 | Hollerbauer |

(Continued)

FOREIGN PATENT DOCUMENTS

| DE | 19533541 C1 | 3/1997 |
|---|---|---|
| DE | 102007021284 A1 | 11/2008 |

(Continued)

OTHER PUBLICATIONS

U.S. Appl. No. 16/526,443, filed Jul. 30, 2019, Spitznagel et al.

(Continued)

*Primary Examiner* — Michael Tomaszewski
*Assistant Examiner* — Jay M. Patel
(74) *Attorney, Agent, or Firm* — Wolf, Greenfield & Sacks, P.C.

(57) ABSTRACT

According to some aspects, a system for automatically processing text comprising information regarding a patient encounter to assign medical codes to the text is provided. The system comprises at least one storage medium storing processor-executable instructions, and at least one processor configured to execute the processor-executable instructions to perform analyzing the text to extract a plurality of facts from the text, identifying at least one of the plurality of facts to be excluded from consideration when assigning medical codes to the text, and evaluating each of the plurality of facts, except for the identified at least one fact, to assign one or more medical codes to the text.

19 Claims, 28 Drawing Sheets

(51) Int. Cl.
*G06F 40/30* (2020.01)
*G06N 20/00* (2019.01)

(56) References Cited

U.S. PATENT DOCUMENTS

| | | |
|---|---|---|
| 5,051,924 A | 9/1991 | Bergeron et al. |
| 5,307,262 A | 4/1994 | Ertel |
| 5,680,511 A | 10/1997 | Baker et al. |
| 5,758,322 A | 5/1998 | Rongley |
| 5,787,394 A | 7/1998 | Bahl et al. |
| 5,909,667 A | 6/1999 | Leontiades et al. |
| 5,924,074 A | 7/1999 | Evans |
| 5,999,896 A | 12/1999 | Richardson et al. |
| 6,003,002 A | 12/1999 | Netsch |
| 6,073,101 A | 6/2000 | Maes |
| 6,173,259 B1 | 1/2001 | Bijl et al. |
| 6,212,498 B1 | 4/2001 | Sherwood et al. |
| 6,292,771 B1 | 9/2001 | Haug et al. |
| 6,360,237 B1 | 3/2002 | Schulz et al. |
| 6,366,882 B1 | 4/2002 | Bijl et al. |
| 6,418,410 B1 | 7/2002 | Nassiff et al. |
| 6,434,547 B1 | 8/2002 | Mishelevich et al. |
| 6,463,413 B1 | 10/2002 | Applebaum et al. |
| 6,487,530 B1 | 11/2002 | Lin et al. |
| 6,519,561 B1 | 2/2003 | Farrell et al. |
| 6,567,778 B1 | 5/2003 | Chao Chang et al. |
| 6,813,603 B1 | 11/2004 | Groner et al. |
| 6,915,254 B1* | 7/2005 | Heinze ............... G16H 50/20 704/9 |
| 7,233,938 B2 | 6/2007 | Carus et al. |
| 7,383,172 B1 | 6/2008 | Jamieson |
| 7,493,253 B1 | 2/2009 | Ceusters et al. |
| 7,610,192 B1 | 10/2009 | Jamieson |
| 7,983,922 B2 | 7/2011 | Neusinger et al. |
| 8,204,756 B2 | 6/2012 | Kim et al. |
| 8,208,641 B2 | 6/2012 | Oh et al. |
| 8,326,653 B2 | 12/2012 | Gottlieb et al. |
| 8,612,261 B1* | 12/2013 | Swanson ............ G06F 19/3418 705/3 |
| 8,694,335 B2 | 4/2014 | Yegnanarayanan |
| 8,756,079 B2 | 6/2014 | Yegnanarayanan |
| 8,943,437 B2 | 1/2015 | Meurs |
| 9,324,321 B2 | 4/2016 | Xue et al. |
| 9,478,218 B2 | 10/2016 | Shu |
| 9,715,576 B2 | 7/2017 | Hayter, II |
| 9,892,734 B2* | 2/2018 | Koll ................... G06F 40/30 |
| 10,319,004 B2 | 6/2019 | Reiser et al. |
| 10,331,763 B2 | 6/2019 | Subramanian et al. |
| 10,366,424 B2 | 7/2019 | Spitznagel et al. |
| 10,366,687 B2 | 7/2019 | Zhan et al. |
| 10,373,711 B2 | 8/2019 | D'Souza et al. |
| 10,754,925 B2 | 8/2020 | D'Souza et al. |
| 2003/0115083 A1 | 6/2003 | Masarie, Jr. et al. |
| 2003/0163461 A1 | 8/2003 | Gudbjartsson et al. |
| 2003/0212544 A1 | 11/2003 | Acero et al. |
| 2004/0044952 A1 | 3/2004 | Jiang et al. |
| 2004/0073458 A1 | 4/2004 | Jensen |
| 2004/0220831 A1 | 11/2004 | Fabricant |
| 2005/0033574 A1 | 2/2005 | Kim et al. |
| 2005/0228815 A1 | 10/2005 | Carus et al. |
| 2005/0240439 A1 | 10/2005 | Covit et al. |
| 2006/0136197 A1 | 6/2006 | Oon |
| 2006/0190300 A1 | 8/2006 | Drucker et al. |
| 2006/0242190 A1* | 10/2006 | Wnek ................... G06F 16/367 |
| 2007/0033026 A1 | 2/2007 | Bartosik et al. |
| 2007/0050187 A1 | 3/2007 | Cox |
| 2007/0088564 A1 | 4/2007 | March et al. |
| 2007/0208567 A1 | 9/2007 | Amento et al. |
| 2008/0002842 A1 | 1/2008 | Neusinger et al. |
| 2008/0004505 A1 | 1/2008 | Kapit et al. |
| 2008/0147436 A1 | 6/2008 | Ohlsson |
| 2008/0222734 A1* | 9/2008 | Redlich ............... H04L 63/02 726/26 |
| 2008/0255835 A1 | 10/2008 | Ollason et al. |
| 2008/0262853 A1 | 10/2008 | Jung et al. |
| 2008/0270120 A1 | 10/2008 | Pestian et al. |
| 2009/0157411 A1 | 6/2009 | Kim et al. |
| 2009/0210238 A1 | 8/2009 | Kim et al. |
| 2009/0216528 A1 | 8/2009 | Gemello et al. |
| 2009/0281839 A1* | 11/2009 | Lynn ................... G06Q 50/22 705/3 |
| 2009/0326958 A1 | 12/2009 | Kim et al. |
| 2010/0023319 A1 | 1/2010 | Bikel et al. |
| 2010/0049756 A1 | 2/2010 | Chemitiganti et al. |
| 2010/0076772 A1 | 3/2010 | Kim et al. |
| 2010/0076774 A1 | 3/2010 | Breebaart |
| 2010/0161316 A1* | 6/2010 | Haug ................... G06F 40/216 704/9 |
| 2010/0198602 A1 | 8/2010 | Oh et al. |
| 2010/0250236 A1 | 9/2010 | Jagannathan et al. |
| 2010/0274584 A1* | 10/2010 | Kim ..................... G06Q 50/24 705/3 |
| 2011/0040576 A1 | 2/2011 | Madan et al. |
| 2012/0078763 A1* | 3/2012 | Koll ..................... G06Q 30/04 705/34 |
| 2012/0089629 A1 | 4/2012 | Koll et al. |
| 2012/0109641 A1 | 5/2012 | Boone et al. |
| 2012/0215559 A1 | 8/2012 | Flanagan et al. |
| 2012/0245961 A1 | 9/2012 | Yegnanarayanan |
| 2013/0035961 A1* | 2/2013 | Yegnanarayanan ..... G06F 19/00 705/3 |
| 2013/0041685 A1 | 2/2013 | Yegnanarayanan |
| 2013/0067319 A1* | 3/2013 | Olszewski ............. G06F 16/35 715/234 |
| 2013/0073301 A1 | 3/2013 | Rao et al. |
| 2013/0080187 A1 | 3/2013 | Bacon et al. |
| 2013/0246079 A1 | 9/2013 | Habboush et al. |
| 2013/0297347 A1 | 11/2013 | Cardoza et al. |
| 2013/0297348 A1 | 11/2013 | Cardoza et al. |
| 2013/0318076 A1* | 11/2013 | Chiticariu ............. G06F 40/242 707/723 |
| 2014/0164023 A1 | 6/2014 | Yegnanarayanan |
| 2014/0244257 A1 | 8/2014 | Colibro et al. |
| 2014/0257803 A1 | 9/2014 | Yu et al. |
| 2014/0278460 A1 | 9/2014 | Dart et al. |
| 2014/0280353 A1 | 9/2014 | Delaney et al. |
| 2014/0343957 A1* | 11/2014 | Dejori ................... G16H 50/20 705/2 |
| 2014/0372142 A1 | 12/2014 | Reddy |
| 2014/0372147 A1 | 12/2014 | White |
| 2014/0372216 A1* | 12/2014 | Nath ................... G06Q 30/0251 705/14.54 |
| 2015/0039299 A1 | 2/2015 | Weinstein et al. |
| 2015/0039301 A1 | 2/2015 | Senior et al. |
| 2015/0039344 A1 | 2/2015 | Kinney |
| 2015/0046178 A1 | 2/2015 | Jindal |
| 2015/0066974 A1 | 3/2015 | Winn |
| 2015/0095016 A1* | 4/2015 | Karres ................... G16H 10/20 704/9 |
| 2015/0112680 A1 | 4/2015 | Lu |
| 2015/0134361 A1* | 5/2015 | Molenda ................ G06Q 50/24 705/3 |
| 2015/0149165 A1 | 5/2015 | Saon |
| 2015/0161522 A1 | 6/2015 | Saon et al. |
| 2015/0161995 A1 | 6/2015 | Sainath et al. |
| 2015/0178874 A1 | 6/2015 | Harris et al. |
| 2015/0356057 A1 | 12/2015 | Subramanian et al. |
| 2015/0356198 A1 | 12/2015 | D'Souza et al. |
| 2015/0356246 A1 | 12/2015 | D'Souza et al. |
| 2015/0356260 A1* | 12/2015 | D'Souza ............... G06F 19/328 705/2 |
| 2015/0356458 A1* | 12/2015 | Berengueres .......... G06N 20/00 706/12 |
| 2015/0356646 A1 | 12/2015 | Spitznagel et al. |
| 2015/0356647 A1 | 12/2015 | Reiser et al. |
| 2015/0371634 A1 | 12/2015 | Kim |
| 2015/0379241 A1 | 12/2015 | Furst et al. |
| 2016/0012186 A1 | 1/2016 | Zasowski et al. |
| 2016/0085743 A1 | 3/2016 | Haley |
| 2016/0260428 A1 | 9/2016 | Matsuda et al. |
| 2016/0300034 A1* | 10/2016 | Huddar ................ G16H 10/60 |
| 2016/0364532 A1 | 12/2016 | Honeycutt et al. |
| 2017/0039326 A1* | 2/2017 | Stankiewicz ......... G06Q 10/063 |

(56) References Cited

U.S. PATENT DOCUMENTS

| | | | |
|---|---|---|---|
| 2017/0061085 A1* | 3/2017 | Nossal | G06F 40/211 |
| 2017/0104785 A1* | 4/2017 | Stolfo | G06N 20/00 |
| 2017/0116373 A1* | 4/2017 | Ginsburg | G16H 40/20 |
| 2017/0169815 A1 | 6/2017 | Zhan et al. | |
| 2017/0300635 A1* | 10/2017 | Ganesan | G16H 15/00 |
| 2017/0323060 A1 | 11/2017 | D'Souza et al. | |
| 2017/0323061 A1 | 11/2017 | D'Souza et al. | |
| 2018/0032678 A1* | 2/2018 | Dandala | G06F 19/00 |
| 2018/0032679 A1* | 2/2018 | Dandala | G06F 3/0482 |
| 2018/0052961 A1* | 2/2018 | Shrivastava | G16H 40/63 |
| 2018/0081859 A1 | 3/2018 | Snider et al. | |
| 2018/0089373 A1* | 3/2018 | Matsuguchi | G16B 99/00 |
| 2018/0090142 A1* | 3/2018 | Li | G10L 15/22 |
| 2018/0119137 A1* | 5/2018 | Matsuguchi | C12Q 1/6827 |
| 2018/0373844 A1 | 12/2018 | Ferrandez-Escamez et al. | |
| 2019/0080450 A1* | 3/2019 | Arar | G06T 7/0012 |
| 2019/0325859 A1 | 10/2019 | Zhan et al. | |
| 2019/0385202 A1 | 12/2019 | Reiser et al. | |
| 2020/0126130 A1 | 4/2020 | Spitznagel et al. | |
| 2020/0126643 A1 | 4/2020 | D'Souza et al. | |

FOREIGN PATENT DOCUMENTS

| | | |
|---|---|---|
| EP | 1 361 522 A2 | 11/2003 |
| WO | WO 98/19253 A1 | 5/1998 |
| WO | WO 2013/133891 A1 | 9/2013 |
| WO | WO 2015/084615 A1 | 6/2015 |

OTHER PUBLICATIONS

U.S. Appl. No. 15/632,152, filed Jun. 23, 2017, Oscar et al.
Aronow et al., Ad Hoc Classification of Radiology Reports. Journal of the American Medical Informatics Association. 1999;6(5):393-411.
Bateman et al., The Quest for the Last 5%: Interfaces for Correcting Real-Time Speech-Generated Subtitles. Interactive Posters. CHI 2000. 2 pages.
Birnbaum et al., Report: A Voice Password System for Access Security. AT&T Technical Journal. 1986. 7 pages.
Bisani et al., Automatic Editing in a Back-End Speech-to-Text System. Proceedings of ACL-08: HLT. 2008:114-20.
Heng-Hsou et al., An Event-Driven and Ontology-Based Approach for the Delivery and Information Extraction of E-mails. IEEE. 2000. 103-9.
Hewitt et al., Real-Time Speech-Generated Subtitles: Problems and Solutions. ISCA Archive. 6th International Conference on Spoken Language Processing (ICSLP 2000). 2000. 5 pages.
Mendonca et al., Extracting information on pnemonia in infants using natural language processing of radiology reports. Journal of Biomedical Informatics. 2005;38:314-21.
Naik, Speaker Verification: A Tutorial. IEEE Communications Magazine. 1990:42-8.
Newman et al., Speaker Verifcation Through Large Vocabulary Continuous Speech Recognition. Dragon Systems, Inc. 1996. 4 pages.
Rosenberg, Evaluation of an Automatic Speaker-Verification System Over Telephone Lines. Manuscript received Sep. 9, 1975. The Bell System Technical Journal. 1976;55(6):723-44.
Shvaiko et al., Ontology Matching OM—2008. Papers from the ISWC Workshop. 2008. 271 pages.
Sistrom et al., Managing Predefined Templated and Macros for a Departmental Speech Recognition System Using Common Software. Journal of Digital Imaging. 2001;14(3):131-41.
Soderland et al., Automated Classification of Encounter Notes in a Computer Based Medical Record. MEDINFO 1995 Proceedings. 1995 IMIA. 9 pages.
Sonntag et al., A Discourse and Dialogue Infrastructure for Industrial Dissemination. German Research Center for AI (DFKI). Proceeding IWSDS'10 Proceedings of the Second international conference on Spoken dialogue systems for ambient environments. 2010. 12 pages.
Sonntag et al., RadSpeech's Mobile Dialogue System for Radiologists. IUI'12. 2012. 2 pages.
Suhm, Multimodal Interactive Error Recovery for Non-Conversation Speech User Interfaces. Dissertation. 1998. 292 pages.
Taira et al., Automatic Structuring of Radiology Free-Text Reports. infoRAD. Radiology 2001;21:237-45.
U.S. Appl. No. 14/296,214, filed Jun. 4, 2014, Spitznagel et al.
U.S. Appl. No. 14/296,249, filed Jun. 4, 2014, Subramanian et al.
U.S. Appl. No. 14/296,256, filed Jun. 4, 2014, D'Souza et al.
U.S. Appl. No. 14/296,274, filed Jun. 4, 2014, D'Souza et al.
U.S. Appl. No. 14/296,295, filed Jun. 4, 2014, D'Souza et al.
U.S. Appl. No. 16/402,867, filed May 3, 2019, Subramanian et al.
U.S. Appl. No. 15/977,451, filed May 11, 2018, D'Souza et al.
U.S. Appl. No. 16/502,626, filed Jul. 3, 2019, D'Souza et al.
U.S. Appl. No. 14/296,303, filed Jun. 4, 2014, Reiser et al.
U.S. Appl. No. 16/395,954, filed Apr. 26, 2019, Reiser et al.
U.S. Appl. No. 14/965,637, filed Dec. 10, 2015, Zhan et al.
U.S. Appl. No. 16/459,335, filed Jul. 1, 2019, Zhan et al.
U.S. Appl. No. 15/372,338, filed Dec. 7, 2016, D'Souza et al.
U.S. Appl. No. 15/366,905, filed Dec. 1, 2016, D'Souza et al.
U.S. Appl. No. 15/710,319, filed Sep. 20, 2017, Snider et al.
PCT/US2015/033130, Aug. 6, 2015, International Search Report and Written Opinion.
PCT/US2015/033642, Sep. 9, 2015, International Search Report and Written Opinion.
PCT/US2015/033648, Aug. 11, 2015, International Search Report and Written Opinion.
PCT/US2016/061326, Feb. 21, 2017, International Search Report and Written Opinion.
PCT/US2016/061326, Jun. 21, 2018, International Preliminary Report on Patentability.
PCT/US2017/052542, Dec. 14, 2017, International Search Report and Written Opinion.
PCT/US2017/052542, Apr. 4, 2019, International Preliminary Report on Patentability.
International Search Report and Written Opinion for International Application No. PCT/US2015/033642 dated Sep. 9, 2015.
International Search Report and Written Opinion for International Application No. PCT/US2015/033130 dated Aug. 6, 2015.
International Search Report and Written Opinion for International Application No. PCT/US2015/033648 dated Aug. 11, 2015.
International Search Report and Written Opinion for International Application No. PCT/US2016/061326 dated Feb. 21, 2017.
International Preliminary Report on Patentability for International Application No. PCT/US2016/061326 dated Jun. 21, 2018.
International Search Report and Written Opinion for International Application No. PCT/US2017/052542 dated Dec. 14, 2017.
International Preliminary Report on Patentability for International Application No. PCT/US2017/052542 dated Apr. 4, 2019.
[No Author Listed], Asthma specificity and tobacco use highlight ICD-10-CM respiratory changes. HCPro. JustCoding News. 2014. 4 pages.
[No Author Listed], Chronic lower respiratory diseases J40-J47. 2015 ICD-10-CM Diagnosis Codes. ICD10Data.com 2015. 6 pages.
[No Author Listed], Injury, poisoning and certain other consequences of external causes S00-T88. 2015 ICD-10-CM Diagnosis Codes. ICD10Data.com 2015. 35 pages.
Abrash et al., Connectionist Speaker Normalization and Adaptation. Proc. EUROSPEECH'95, 1995. 4 pages.
Cimiano et al., "Learning concept hierarchies from text with a guided hierarchical clustering algorithm," In C. Biemann and G. Paas (eds.), Proceedings of the ICML 2005 Workshop on Learning and Extending Lexical Ontologies with Machine Learning Methods, Bonn, Germany, (2005).
Fan et al., "PRISMATIC: Inducing Knowledge from a Large Scale Lexicalized Relation Resource," Proceedings of the NAACL HLT 2010 First International Workshop on Formalisms and Methodology for Learning by Reading, pp. 122-127, Los Angeles, California, Jun. 2010.
Ferrao et al., Clinical Coding Support Based on Structured Data Stored in Electronic Health Records. IEEE International Conference on Bioinformatics and Biomedicine Workshops. 2012. 790-7.

(56) References Cited

OTHER PUBLICATIONS

Florian et al., "A Statistical Model for Multilingual Entity Detection and Tracking," Proceedings of the Human Language Technologies Conference 2004 (HLT-NAACL'04), (2004).
Gemello et al., Linear hidden transformations for adaptation of hybrid ANN/HMM Models. Speech Communication. 2007;49:827-35.
Gomez-Perez et al., "An overview of methods and tools for ontology learning from texts," Knowledge Engineering Review 19:3 p. 187-212, 2004.
Omar, Fast Approximate I-Vector Estimation Using PCA. Proc. ICASSP. IEEE, 2015;4495-9.
Salton et al., "A Vector Space Model for Automatic Indexing," Communications of the ACM, vol. 18, No. 11, Nov. 1975.
Saon et al., Speaker Adaptation of Neural Network Acoustic Models Using I-Vectors. IEEE. 2013;55-9.
Senior et al., Improving DNN speaker independence with I-vector inputs. 2014 IEEE International Conference on Acoustics, Speech and Signal Processing (ICASSP), IEEE. 2014;225-9.
Welty et al., "Large Scale Relation Detection," Proceedings of the NAACL HLT 2010 First International Workshop on Formalisms and Methodology for Learning by Reading, pp. 24-33, Los Angeles, California, Jun. 2010.
U.S. Appl. No. 16/928,519, filed Jul. 14, 2020, D'Souza et al.

\* cited by examiner

FIG. 3A

- Patient Name: John Doe    Sex: M    Creation Date: 01-18-2011
- Document Type: Discharge Summary Problems  Medications  Allergies  Social History  Procedures  Vital Signs    Hide All Chief complaint: Patient is presenting chest pain and shortness of breath.

Medical history: The patient is hypertensive. He is also obese.

Social history: He smokes one pack per day. Drinks occasionally.

Problems(4) — 310

Add Fact

| Name | Status |
|---|---|
| × Unspecified Chest Pain | active |
| × Shortness of Breath | active |
| × Unspecified Essential Hypertension | history |
| × Obesity Unspecified | history |

Medications(1) — 320

Add Fact

| Name | Status | Schedules |
|---|---|---|
| × | | None |

Allergies(0) — 330

Add Fact

| Name | Type | Status |
|---|---|---|

Save  Dictate  Complete  Cancel

Document List — 710
- History & Physical
  - 6/13/2014
  - 6/15/2014
- Discharge Summary — 712
  - 6/18/2014
- Emergency Room Record
  - 6/13/2014
- Consultation
  - 6/16/2014
- Progress Notes
  - 6/17/2014
- Operative Report
  - 6/13/2014

Submit — 750

Discharge Summary 6/18/2014 — 720

HISTORY OF PRESENT ILLNESS/ HOSPTIAL COURSE:

The patient is a 63-year old male with a history of multiple medical problems. He was originally admitted on June 13 when he was found unresponsive at home. Left heart catheterization showed normal coronaries, and no pulmonary embolism appreciated on pulmonary angiogram. Bilateral infiltrative changes suggested pneumonia. Patient was treated for that and sent to rehab unit. He developed respiratory distress and was readmitted to the hospital with hypercapnic respiratory failure. He was intubated and put into the — 722 ICU. The patient is doing well today. No acute symptoms. He denies any chest pain or shortness of breath. No fevers or chills.

Code List — 730, 740

| Diagnosis | Procedure | | |
|---|---|---|---|
| | ICD9 | Description | POA |
| ☑ | 518.81 | Acute Respiratory Failure | |
| ○ | 287.5 | Thrombocytopenia NOS | |
| ○ | 338.4 | Chronic Pain Syndrome | |
| ○ | 571.5 | Cirrhosis of Liver w/o Alcohol | |
| ○ | 303.90 | Alcohol Dependence NEC/NOS | |
| ○ | 571.2 | Alcoholic Cirrhosis of Liver | |
| ○ | 428.0 | Congestive Heart Failure, Unspec | |
| ○ | 482.9 | Bacterial Pneumonia NOS | |

Document List (710):
- History & Physical
  - 6/13/2014
  - 6/15/2014
- Discharge Summary (712)
  - 6/18/2014
- Emergency Room Record
  - 6/13/2014
- Consultation
  - 6/16/2014
- Progress Notes
  - 6/17/2014
- Operative Report
  - 6/13/2014

Submit (750)

Discharge Summary 6/18/2014 (720)

HISTORY OF PRESENT ILLNESS/ HOSPTIAL COURSE:

The patient is a 63-year old male with a history of multiple medical problems. He was originally admitted on June 13 when he was found unresponsive at home. Left heart catheterization showed normal coronaries, and no pulmonary embolism appreciated on pulmonary angiogram. Bilateral infiltrative changes suggested pneumonia. Patient was treated for that and sent to rehab unit. He developed respiratory distress and was readmitted to the hospital with hypercapnic respiratory failure. He was intubated and put into the ICU. The (Linked to 518.81) today. No acute symptoms. He denies any chest pain or shortness of breath. No fevers or chills.

(724)

Code List (730):

| Diagnosis | Procedure | | |
|---|---|---|---|
| | ICD9 | Description | POA |
| ☑ | 518.81 | Acute Respiratory Failure | |
| ○ | 287.5 | Thrombocytopenia NOS | |
| ○ | 338.4 | Chronic Pain Syndrome | |
| ○ | 571.5 | Cirrhosis of Liver w/o Alcohol | |
| ○ | 303.90 | Alcohol Dependence NEC/NOS | |
| ○ | 571.2 | Alcoholic Cirrhosis of Liver | |
| ○ | 428.0 | Congestive Heart Failure, Unspec | |
| ○ | 482.9 | Bacterial Pneumonia NOS | |

Document List 710

- History & Physical
  - 6/13/2014
  - 6/15/2014
- Discharge Summary — 712
  - 6/18/2014
- Emergency Room Record
  - 6/13/2014
- Consultation
  - 6/16/2014
- Progress Notes
  - 6/17/2014
- Operative Report
  - 6/13/2014

Submit — 750

720

Discharge Summary 6/18/2014

HISTORY OF PRESENT ILLNESS/HOSPTIAL COURSE:

The patient is a 63-year old male with a history of multiple medical problems. He was originally admitted on June 13 when he was found unresponsive at home. Left heart catheterization showed normal coronaries, and no pulmonary embolism appreciated on pulmonary angiogram. Bilateral infiltrative changes suggested pneumonia. Patient was treated for that and sent to rehab unit. He developed respiratory distress and was readmitted to the hospital with hypercapnic respiratory failure. He was intubated and put into the ICU. The patient is doing well today. No acute symptoms. He denies any chest pain or shortness of breath. No fevers or chills.

Code List — 740

730

| Diagnosis | Procedure | | |
|---|---|---|---|
| | ICD9 | Description | POA |
| ☑ ▷ | 518.81 | Acute Respiratory Failure | |
| ○ | 287.5 | Thrombocytopenia | |
| ○ | 338 | ▷ Show Highlights / Accept / Reject / Replace / Link Text / Unlink Text | |
| ○ | 571 | | |
| ○ | 303 | NEC/NOS | |
| ○ | 571.2 | Alcoholic Cirrhosis of Liver | |
| ○ | 428.0 | Congestive Heart Failure, Unspec | |
| ○ | 482.9 | Bacterial Pneumonia NOS | |

Document List 710

- History & Physical
  - 6/13/2014
  - 6/15/2014
- Discharge Summary — 712
  - 6/18/2014
- Emergency Room Record
  - 6/13/2014
- Consultation
  - 6/16/2014
- Progress Notes
  - 6/17/2014
- Operative Report
  - 6/13/2014

Submit — 750

720

Discharge Summary 6/18/2014

DISCHARGE DIAGNOSES:
1. Acute hypercapnic respiratory failure.
2. Thrombocytopenia. — 726
3. Chronic pain syndrome.
4. History of liver cirrhosis.
5. Alcoholism.
6. Congestive heart failure (CHF)
7. History of multilobular pseudomonas pneumonia in sacral wounds with general deconditioning, weakness and fatigue.

HISTORY OF PRESENT ILLNESS/ HOSPITAL COURSE

The patient is a 63-year old male with a history of multiple medical problems. He was originally admitted on June 13 when he was found

Code List — 740

| Diagnosis | Procedure | | |
|---|---|---|---|
| ICD9 | Description | | POA |
| ☑ 518.81 | Acute Respiratory Failure | | |
| ○ 287.5 | Thrombocytopenia NOS | | |
| ○ 338.4 | Chronic Pain Syndrome | | |
| ○ 571.5 | Cirrhosis of Liver w/o Alcohol | | |
| ○ 303.90 | Alcohol Dependence NEC/NOS | | |
| ○ 571.2 | Alcoholic Cirrhosis of Liver | | |
| ○ 428.0 | Congestive Heart Failure, Unspec | | |
| ○ 482.9 | Bacterial Pneumonia NOS | | |

Submit — 750

Document List — 710

- History & Physical
  - 6/13/2014
  - 6/15/2014
- Discharge Summary
  - 6/18/2014 — 712
- Emergency Room Record
  - 6/13/2014
- Consultation
  - 6/16/2014
- Progress Notes
  - 6/17/2014
- Operative Report
  - 6/13/2014

Discharge Summary 6/18/2014 — 720

DISCHARGE DIAGNOSES:
1. Acute hypercapnic respiratory failure.
2. Thrombocytopenia.
3. Chronic pain syndrome.
4. History of liver cirrhosis.
5. Alcoholism.
6. Congestive heart failure (CH
7. History of multilobular pseudomonas pneumonia in sacral wounds with general deconditioning, weakness and fatigue.

☑ Incorrect Code
More specific code needed
Partial Code
Negated Code
Not Billable
Payor Specific

HISTORY OF PRESENT ILLNESS/ HOSPITAL COURSE

The patient is a 63-year old male with a history of multiple medical problems. He was originally admitted on June 13 when he was found

Code List — 730

| | | Diagnosis | Procedure | | |
|---|---|---|---|---|---|
| | | ICD9 | Description | | POA |
| ○▽ | | | | | |
| ⊘ | | 518.81 | Acute Respiratory Failure | | |
| ⊘ | | 287.5 | Thrombocytopenia NOS | | |
| | | 3.4 | Chronic Pain Syndrome | | |
| | | .5 | Cirrhosis of Liver | | |
| | | | Show Highlights | dence | |
| ⊘ | | 57 | Accept | osis | |
| | | | Rejected Reason | | |
| ⊘ | | 42 | Replace | art | |
| | | | Link Text | | |
| ⊕ | | 482.1 | Unlink Text | Pneumonia due to Pseudomonas | |
| ⊕ | | 041.7 | | Pseudomonas Infection Site NOS | |

— 740

| Save — 810 | | |
|---|---|---|
| Code | Description | POA |
| 1. 518.81 | Acute Respiratory Failure | N |
| 2. 287.5 | Thrombocytopenia NOS | Y |
| 3. 338.4 | Chronic Pain Syndrome | Y |
| 4. 303.90 | Alcohol Dependence NEC/NOS | Y |
| 5. 571.2 | Alcoholic Cirrhosis of Liver | Y |
| 6. 428.0 | Congestive Heart Failure, Unspecified | Y |
| 7. 482.1 | Pneumonia due to Pseudomonas | Y |
| 8. 041.7 | Pseudomonas Infection Site NOS/Dis Class Elsewhere | Y |

FIG. 8

COMPUTER ASSISTED CODING SYSTEMS AND METHODS

BACKGROUND

Medical documentation is an important process in the healthcare industry. Most healthcare institutions maintain a longitudinal medical record (e.g., spanning multiple observations or treatments over time) for each of their patients, documenting, for example, the patient's history, encounters with clinical staff within the institution, treatment received, and/or plans for future treatment. Such documentation facilitates maintaining continuity of care for the patient across multiple encounters with various clinicians over time. In addition, when an institution's medical records for large numbers of patients are considered in the aggregate, the information contained therein can be useful for educating clinicians as to treatment efficacy and best practices, for internal auditing within the institution, for quality assurance, etc.

Historically, each patient's medical record was maintained as a physical paper folder, often referred to as a "medical chart", or "chart". Each patient's chart would include a stack of paper reports, such as intake forms, history and immunization records, laboratory results and clinicians' notes. Following an encounter with the patient, such as an office visit, a hospital round or a surgical procedure, the clinician conducting the encounter would provide a narrative note about the encounter to be included in the patient's chart. Such a note could include, for example, a description of the reason(s) for the patient encounter, an account of any vital signs, test results and/or other clinical data collected during the encounter, one or more diagnoses determined by the clinician from the encounter, and a description of a plan for further treatment. Often, the clinician would verbally dictate the note into an audio recording device or a telephone giving access to such a recording device, to spare the clinician the time it would take to prepare the note in written form. Later, a medical transcriptionist would listen to the audio recording and transcribe it into a text document, which would be inserted on a piece of paper into the patient's chart for later reference.

Currently, many healthcare institutions are transitioning or have transitioned from paper documentation to electronic medical record systems, in which patients' longitudinal medical information is stored in a data repository in electronic form. Besides the significant physical space savings afforded by the replacement of paper record-keeping with electronic storage methods, the use of electronic medical records also provides beneficial time savings and other opportunities to clinicians and other healthcare personnel. For example, when updating a patient's electronic medical record to reflect a current patient encounter, a clinician need only document the new information obtained from the encounter, and need not spend time entering unchanged information such as the patient's age, gender, medical history, etc. Electronic medical records can also be shared, accessed and updated by multiple different personnel from local and remote locations through suitable user interfaces and network connections, eliminating the need to retrieve and deliver paper files from a crowded file room.

Another modern trend in healthcare management is the importance of medical coding for documentation and billing purposes. In the medical coding process, documented information regarding a patient encounter, such as the patient's diagnoses and clinical procedures performed, is classified according to one or more standardized sets of codes for reporting to various entities such as payment providers (e.g., health insurance companies that reimburse clinicians for their services). In the United States, some such standardized code systems have been adopted by the federal government, which then maintains the code sets and recommends or mandates their use for billing under programs such as Medicare.

For example, the International Classification of Diseases (ICD) numerical coding standard, developed from a European standard by the World Health Organization (WHO), was adopted in the U.S. in version ICD-9-CM (Clinically Modified). It is mandated by the Health Insurance Portability and Accountability Act of 1996 (HIPAA) for use in coding patient diagnoses. The Centers for Disease Control (CDC), the National Center for Health Statistics (NCHS), and the Centers for Medicare and Medicaid Services (CMS) are the U.S. government agencies responsible for overseeing all changes and modifications to ICD-9-CM, and a new version ICD-10-CM is scheduled for adoption in 2015.

Another example of a standardized code system adopted by the U.S. government is the Current Procedural Terminology (CPT) code set, which classifies clinical procedures in five-character alphanumeric codes. The CPT code set is owned by the American Medical Association (AMA), and its use is mandated by CMS as part of the Healthcare Common Procedure Coding System (HCPCS). CPT forms HCPCS Level I, and HCPCS Level II adds codes for medical supplies, durable medical goods, non-physician healthcare services, and other healthcare services not represented in CPT. CMS maintains and distributes the HCPCS Level II codes with quarterly updates.

Conventionally, the coding of a patient encounter has been a manual process performed by a human professional, referred to as a "medical coder" or simply "coder," with expert training in medical terminology and documentation as well as the standardized code sets being used and the relevant regulations. The coder would read the available documentation from the patient encounter, such as the clinicians' narrative reports, laboratory and radiology test results, etc., and determine the appropriate medical billing codes to assign to the encounter. The coder might make use of a medical coding system, such as a software program running on suitable hardware, that would display the documents from the patient encounter for the coder to read, and allow the coder to manually input the appropriate medical billing codes into a set of fields for entry in the record. Once finalized, the set of codes entered for the patient encounter could then be sent to a payment provider, which would typically determine the level of reimbursement for the encounter according to the particular codes that were entered.

SUMMARY

Some embodiments include a system for automatically processing text comprising information regarding a patient encounter to assign medical billing codes to the text, the system comprising at least one storage medium storing processor-executable instructions and at least one processor configured to execute the processor-executable instructions to analyze the text to extract a plurality of facts from the text, parse the text into a plurality of text regions, identify at least one of the plurality of text regions, from which at least one of the plurality of facts was extracted, that should not be processed for medical billing code assignment based, at least in part, on content of the respective text region, and process each of the plurality of text regions, except for the identified at least one of the plurality of text regions, to assign one or more medical billing codes to the text based, at least in part, on one or more of the plurality of facts extracted from the processed text regions.

Some embodiments include a method for automatically processing text comprising information regarding a patient encounter to assign medical billing codes to the text, the method comprising analyzing the text to extract a plurality of facts from the text, parsing the text into a plurality of text regions, identifying at least one of the plurality of text regions, from which at least one of the plurality of facts was extracted, that should not be processed for medical billing code assignment based, at least in part, on content of the respective text region, and processing each of the plurality of text regions, except for the identified at least one of the plurality of text regions, to assign one or more medical billing codes to the text based, at least in part, on one or more of the plurality of facts extracted from the processed text regions.

Some embodiments include at least one computer readable medium storing instructions that, when executed by at least one processor, perform a method of automatically processing text comprising information regarding a patient encounter to assign medical billing codes to the text, the method comprising analyzing the text to extract a plurality of facts from the text, parsing the text into a plurality of text regions, identifying at least one of the plurality of text regions, from which at least one of the plurality of facts was extracted, that should not be processed for medical billing code assignment based, at least in part, on content of the respective text region, and processing each of the plurality of text regions, except for the identified at least one of the plurality of text regions, to assign one or more medical billing codes to the text based, at least in part, on one or more of the plurality of facts extracted from the processed text regions.

Some embodiment include a method of training a model to facilitate identifying text regions that are likely to be incorrectly assigned medical billing codes, the method comprising receiving training data comprising a plurality of texts corresponding to respective patient encounters, each of the plurality of texts having been assigned a plurality of medical billing codes reviewed by at least one user, each of the plurality of texts including a respective plurality of text regions, each having been assigned at least one medical billing code, the training data further comprising feedback from the at least one user indicating whether each medical billing code was correctly and/or incorrectly assigned, transforming each of the plurality of text regions of each of the plurality of texts to a respective representation to provide a plurality of representations, clustering the plurality of representations, and labeling each cluster as a false positive cluster or a true positive cluster.

Some embodiment include at least one computer readable medium storing instructions that, when executed by at least one processor, perform a method of training a model to facilitate identifying text regions that are likely to be incorrectly assigned medical billing codes, the method comprising receiving training data comprising a plurality of texts corresponding to respective patient encounters, each of the plurality of texts having been assigned a plurality of medical billing codes reviewed by at least one user, each of the plurality of texts including a respective plurality of text regions, each having been assigned at least one medical billing code, the training data further comprising feedback from the at least one user indicating whether each medical billing code was correctly and/or incorrectly assigned, transforming each of the plurality of text regions of each of the plurality of texts to a respective representation to provide a plurality of representations, clustering the plurality of representations, and labeling each cluster as a false positive cluster or a true positive cluster.

Some embodiment include a system for training a model to facilitate identifying text regions that are likely to be incorrectly assigned medical billing codes, the system comprising at least one storage medium storing processor-executable instructions and at least one processor configured to execute the processor-executable instructions to receive training data comprising a plurality of texts corresponding to respective patient encounters, each of the plurality of texts having been assigned a plurality of medical billing codes reviewed by at least one user, each of the plurality of texts including a respective plurality of text regions, each having been assigned at least one medical billing code, the training data further comprising feedback from the at least one user indicating whether each medical billing code was correctly and/or incorrectly assigned, transform each of the plurality of text regions of each of the plurality of texts to a respective representation to provide a plurality of representations, cluster the plurality of representations, and label each cluster as a false positive cluster or a true positive cluster.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIGS. 3A and 3B are screenshots illustrating an exemplary display of medical facts in a user interface in accordance with some embodiments;

FIG. 4 is a screenshot illustrating an exemplary display of linkage between text and a medical fact in accordance with some embodiments;

FIG. 5 is a screenshot illustrating an exemplary interface for entering a medical fact in accordance with some embodiments;

FIGS. 7A-7F are screenshots illustrating an exemplary user interface for a computer-assisted coding (CAC) system in accordance with some embodiments;

FIG. 8 is a screenshot illustrating an exemplary code finalization screen in accordance with some embodiments;

DETAILED DESCRIPTION

Figure 1:
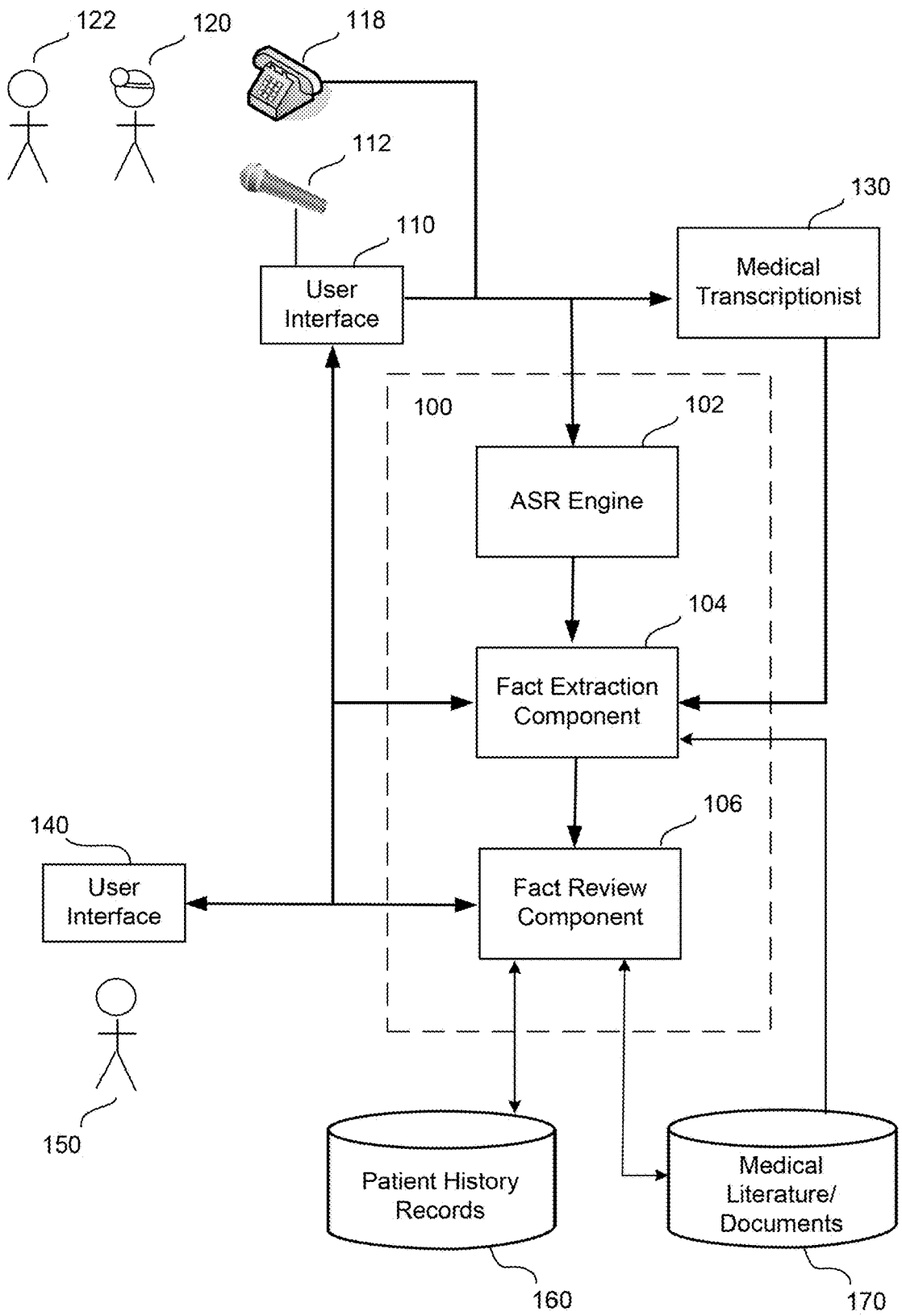
FIG. 1 is a block diagram of an exemplary operating environment for a clinical language understanding (CLU) system that may be employed in connection with some embodiments.

As discussed above, medical billing codes are annotated in patient encounters in order to summarize and normalize the diagnoses made and procedures performed during the patient encounter. As part of the billing process for patent encounters, human medical coders sequence the medical billing codes by importance, with a primary diagnosis first, followed by one or more secondary diagnoses according to coding guidelines. Medical billing codes are also used for maintaining statistics on disorders and treatments and/or for various related research purposes so that sequencing of medical billing codes of patient encounters may follow institution-specific guidelines. Sequencing medical billing codes by importance or significance is an important part of a medical billing coder's job.

Many conventional systems rely on coders to manually generate medical billing codes for patient encounters from the associated documentation. However, manual coding is a time and cost intensive process, requiring trained experts in medical terminology, standardized code sets and relevant regulations to carefully analyze documentation of a patient encounter to accurately assign the proper medical billing codes thereto. To address one or more drawbacks associated with manual coding, Computer-Assisted Medical Coding (CAC) systems have been designed to generate medical billing codes from documentation of a patient encounter, which are then reviewed, edited and sequenced manually by human coders. For example, CAC systems make use of a natural language understanding (NLU) engine to automatically derive semantic information from free-form text documenting a clinical patient encounter to automatically derive and suggest medical billing codes corresponding to the clinical patient encounter.

However, automatically deriving medical billing codes inevitably leads to errors that need to be corrected by the coder. Conventional CAC systems often erroneously assign medical billing codes to facts extracted by the underlying NLU engine in circumstances where a physician expresses information about a patient encounter that is not clinically relevant from a billing perspective. For example, a physician documenting a patient encounter may report that the "These findings are likely related to diverticulitis." A NLU system processing this language may appropriately extract the term "diverticulitis" as a medical fact and correctly label this fact as a disorder. However, conventional CAC systems operating on the output of the NLU may erroneously assign a medical billing code to this medical fact, even though the physician's commentary on what the patient is likely to suffer from is generally not a billable event.

As further examples, commentary on a patient's relatives such as "Mother has a history of endometriosis," statements of negation such as "Patient denies any back pain," recollection of historical conditions and/or procedures such as "Patient had an appendectomy in July 2001," etc., frequently cause conventional CAC systems to suggest medical billing codes to a user even though the clinician may not be documenting billable events. Regions of text with non-diagnostic language such as risk assessment, precautions, etc., frequently give rise to false positive suggestions of medical billing codes to the user. As a result, the user must spend time and effort fixing the erroneous medical billing codes suggested by the CAC system.

The inventors recognized that user feedback indicating whether suggested medical billing codes were correct or incorrect (e.g., by receiving information that suggested medical billing codes were accepted or rejected) can be used as a basis to train the system to learn to identify circumstances that frequently give rise to erroneous medical billing code suggestions (false positives) to improve the performance of a CAC system. Accordingly, one or more problems related to false positive rates of conventional CAC systems is solved by training the system based, at least in part, on information gleaned from a user reviewing, accepting, rejecting and/or otherwise editing medical billing codes suggested by the CAC system. The trained system improves performance by reducing the false positive rate of the CAC system in suggesting medical billing codes to the coder, thereby reducing the time needed for the coder to complete a job and/or improving user satisfaction with the system.

Some embodiments described herein make use of an NLU engine to automatically derive semantic information from free-form text documenting a clinical patient encounter and annotate the text with the derived information including automatically deriving medical codes for the patient encounter. The medical codes may represent medical diagnoses and/or medical procedures, as a non-limiting example, and in some embodiments, may represent or be used as medical billing codes suggested to a user (e.g., via a CAC system). Automatically derived medical billing codes may then be presented to a user (e.g., a medical coding specialist) as suggestions to relieve the user from much or all of the task of assigning medical billing codes for the patient encounter. The user may correct the suggested medical billing codes, for example, by accepting those that the coder agrees with, not accepting those that the coder does not want to keep and/or believes are false positives or otherwise erroneously assigned, or by explicitly rejecting certain medical billing codes.

According to some embodiments, interactions with suggested medical billing codes received from a coder (e.g., additions, deletions, indications of acceptance or rejection, etc.) can be used as feedback to improve the performance of the system in automatically deriving medical codes and, more particularly, reducing the number of false positive medical billing codes that are presented to the user. For example, the feedback may be used as a basis to compile training data to train a diagnostic language relevance (DLR) component to learn the context and/or circumstances that frequently give rise to false positive medical billing code suggestions. The trained DLR component may be utilized to reduce the number of false positive medical billing codes that are presented to the user (e.g., by excluding regions of text that are deemed to include, for example, non-diagnostic language that should not be considered when assessing whether to suggest a medical billing code to a user), solving the problem of conventional CAC systems that have unsatisfactory false positive rates in suggesting medical billing codes (e.g., medical billing codes presented to coder(s) employed by a customer being serviced by the CAC system).

According to some embodiments, a DLR component is trained using training data based on feedback from a particular customer so a DLR component learns the specific preferences, practices and behaviors of the customer. A customer refers herein to any entity that utilizes the services of a CAC system. For example, common customers include hospitals, clinic, or other healthcare institutions, etc. A customer may employ one or more users (e.g., coding specialists) that perform medical coding functions using the CAC system according to the customer's requirements. By using feedback from specific customers separately, a DLR component may be trained for each specific customer. Similarly, by adapting the system via feedback from a respective customer, customer preferences can be learned and the system adapted to optimally reduce false positive rates for the specific customer. According to some embodiments, the training data for a DLR component may be based on feedback from multiple customers, as the aspects are not limited in this respect.

The aspects and embodiments described above, as well as additional aspects and embodiments, are described further below. While a number of inventive features are described above and expanded upon below, it should be appreciated that embodiments of the present invention may include any one of these features, any combination of two or more features, or all of the features, as aspects of the invention are not limited to any particular number or combination of the above-described features. The aspects of the present invention described herein can be implemented in any of numerous ways, and are not limited to any particular implementation techniques. Described below are examples of specific implementation techniques; however, it should be appreciate that these examples are provided merely for purposes of illustration, and that other implementations are possible.

Clinical Language Understanding (CLU) System

An Electronic Health Record (EHR) is an electronic medical record that generally is maintained by a specific healthcare institution and contains data documenting the care that a specific patient has received from that institution over time. Typically, an EHR is maintained as a structured data representation, such as a database with structured fields. Each piece of information stored in such an EHR is typically represented as a discrete (e.g., separate) data item occupying a field of the EHR database. For example, a 55-year old male patient named John Doe may have an EHR database record with "John Doe" stored in the patient_name field, "55" stored in the patient_age field, and "Male" stored in the patient_gender field. Data items or fields in such an EHR are structured in the sense that only a certain limited set of valid inputs is allowed for each field. For example, the patient_name field may require an alphabetic string as input, and may have a maximum length limit; the patient_age field may require a string of three numerals, and the leading numeral may have to be "0" or "1"; the patient_gender field may only allow one of two inputs, "Male" and "Female"; a patient_birth_date field may require input in a "MM/DD/YYYY" format; etc.

Typical EHRs are also structured in terms of the vocabulary they use, as medical terms are normalized to a standard set of terms utilized by the institution maintaining the EHR. The standard set of terms may be specific to the institution, or may be a more widely used standard. For example, a clinician dictating or writing a free-form note may use any of a number of different terms for the condition of a patient currently suffering from an interruption of blood supply to the heart, including "heart attack", "acute myocardial infarction", "acute MI" and "AMI". To facilitate interoperability of EHR data between various departments and users in the institution, and/or to allow identical conditions to be identified as such across patient records for data analysis, a typical EHR may use only one standardized term to represent each individual medical concept. For example, "acute myocardial infarction" may be the standard term stored in the EHR for every case of a heart attack occurring at the time of a clinical encounter. Some EHRs may represent medical terms in a data format corresponding to a coding standard, such as the International Classification of Disease (ICD) standard. For example, "acute myocardial infarction" may be represented in an EHR as "ICD-9 410", where 410 is the code number for "acute myocardial infarction" according to the ninth edition of the ICD standard.

To allow clinicians and other healthcare personnel to enter medical documentation data directly into an EHR in its discrete structured data format, many EHRs are accessed through user interfaces that make extensive use of point-and-click input methods. While some data items, such as the patient's name, may require input in (structured) textual or numeric form, many data items can be input simply through the use of a mouse or other pointing input device (e.g., a touch screen) to make selections from pre-set options in drop-down menus and/or sets of checkboxes and/or radio buttons or the like.

While some clinicians may appreciate the ability to directly enter structured data into an EHR through a point-and-click interface, many clinicians may prefer being unconstrained in what they can say and in what terms they can use in a free-form note, and many may be reluctant to take the time to learn where all the boxes and buttons are and what they all mean in an EHR user interface. In addition, many clinicians may prefer to take advantage of the time savings that can be gained by providing notes through verbal dictation, as speech can often be a faster form of data communication than typing or clicking through forms.

Accordingly, some embodiments described herein relate to techniques for enhancing the creation and use of structured electronic medical records, using techniques that enable a clinician to provide input and observations via a free-form narrative clinician's note. Some embodiments involve the automatic extraction of discrete medical facts (e.g., clinical facts), such as could be stored as discrete structured data items in an electronic medical record, from a clinician's free-form narration of a patient encounter. In this manner, free-form input may be provided, but the advantages of storage, maintenance and accessing of medical documentation data in electronic forms may be maintained. For example, the storage of a patient's medical documentation data as a collection of discrete structured data items may provide the benefits of being able to query for individual data items of interest, and being able to assemble arbitrary subsets of the patient's data items into new reports, orders, invoices, etc., in an automated and efficient manner.

Automatic extraction of medical facts (e.g., clinical facts) from a free-form narration may be performed in any suitable way using any suitable technique(s), as aspects of the present invention are not limited in this respect. In some embodiments, pre-processing may be performed on a free-form narration prior to performing automatic fact extraction, to determine the sequence of words represented by the free-form narration. Such pre-processing may also be performed in any suitable way using any suitable technique(s), as aspects of the present invention are not limited in this respect. For example, in some embodiments, the clinician may provide the free-form narration directly in textual form (e.g., using a keyboard or other text entry device), and the textual free-form narration may be automatically parsed to determine its sequence of words. In other embodiments, the clinician may provide the free-form narration in audio form as a spoken dictation, and an audio recording of the clinician's spoken dictation may be received and/or stored. The audio input may be processed in any suitable way prior to or in the process of performing fact extraction, as aspects of the invention are not limited in this respect. In some embodiments, the audio input may be processed to form a textual representation, and fact extraction may be performed on the textual representation. Such processing to produce a textual representation may be performed in any suitable way. For example, in some embodiments, the audio recording may be transcribed by a human transcriptionist, while in other embodiments, automatic speech recognition (ASR) may be performed on the audio recording to obtain a textual representation of the free-form narration provided via the clinician's dictation. Any suitable automatic speech recognition technique may be used, as aspects of the present invention are not limited in this respect. In other embodiments, speech-to-text conversion of the clinician's audio dictation may not be required, as a technique that does not involve processing the audio to produce a textual representation may be used to determine what was spoken. In one example, the sequence of words that was spoken may be determined directly from the audio recording, e.g., by comparing the audio recording to stored waveform templates to determine the sequence of words. In other examples, the clinician's speech may not be recognized as words, but may be recognized in another form such as a sequence or collection of abstract concepts. It should be appreciated that the words and/or concepts represented in the clinician's free-form narration may be represented and/or stored as data in any suitable form, including forms other than a textual representation, as aspects of the present invention are not limited in this respect.

In some embodiments, one or more medical facts (e.g., clinical facts) may be automatically extracted from the free-form narration (in audio or textual form) or from a pre-processed data representation of the free-form narration using a fact extraction component applying natural language understanding techniques, such as a natural language understanding (NLU) engine. In some embodiments, the medical facts to be extracted may be defined by a set of fact categories (also referred to herein as "fact types" or "entity types") commonly used by clinicians in documenting patient encounters. In some embodiments, a suitable set of fact categories may be defined by any of various known healthcare standards. For example, in some embodiments, the medical facts to be extracted may include facts that are required to be documented by Meaningful Use standards promulgated by the U.S. government, e.g., under 42 C.F.R. § 495, which sets forth "Objectives" specifying items of medical information to be recorded for medical patients. Such facts currently required by the Meaningful Use standards include social history facts, allergy facts, diagnostic test result facts, medication facts, problem facts, procedure facts, and vital sign facts. However, these are merely exemplary, as aspects of the invention are not limited to any particular set of fact categories. Some embodiments may not use one or more of the above-listed fact categories, and some embodiments may use any other suitable fact categories. Other non-limiting examples of suitable categories of medical facts include findings, disorders, body sites, medical devices, subdivided categories such as observable findings and measurable findings, etc. The fact extraction component may be implemented in any suitable form, as aspects of the present invention are not limited in this respect. Exemplary implementations for a fact extraction component are described in detail below.

Some embodiments described herein may make use of a clinical language understanding (CLU) system, an exemplary operating environment for which is illustrated in FIG. 1. CLU system 100, illustrated in FIG. 1, may be implemented in any suitable form, as aspects of the present invention are not limited in this respect. For example, system 100 may be implemented as a single stand-alone machine, or may be implemented by multiple distributed machines that share processing tasks in any suitable manner. System 100 may be implemented as one or more computers; an example of a suitable computer is described below. In some embodiments, system 100 may include one or more tangible, non-transitory computer-readable storage devices storing processor-executable instructions, and one or more processors that execute the processor-executable instructions to perform the functions described herein. The storage devices may be implemented as computer-readable storage media encoded with the processor-executable instructions; examples of suitable computer-readable storage media are discussed below.

As depicted, exemplary system 100 includes an ASR engine 102, a fact extraction component 104, and a fact review component 106. Each of these processing components of system 100 may be implemented in software, hardware, or a combination of software and hardware. Components implemented in software may comprise sets of processor-executable instructions that may be executed by the one or more processors of system 100 to perform the functionality described herein. Each of ASR engine 102, fact extraction component 104 and fact review component 106 may be implemented as a separate component of system 100, or any combination of these components may be integrated into a single component or a set of distributed components. In addition, any one of ASR engine 102, fact extraction component 104 and fact review component 106 may be implemented as a set of multiple software and/or hardware components. It should be understood that any such component depicted in FIG. 1 is not limited to any particular software and/or hardware implementation and/or configuration. Also, not all components of exemplary system 100 illustrated in FIG. 1 are required in all embodiments. For example, in some embodiments, a CLU system may include functionality of fact extraction component 104, which may be implemented using a natural language understanding (NLU) engine, without including ASR engine 102 and/or fact review component 106.

As illustrated in FIG. 1, user interface 110 is presented to a clinician 120, who may be a physician, a physician's aide, a nurse, or any other personnel involved in the evaluation and/or treatment of a patient 122 in a clinical setting. During the course of a clinical encounter with patient 122, or at some point thereafter, clinician 120 may wish to document the patient encounter. Such a patient encounter may include any interaction between clinician 120 and patient 122 in a clinical evaluation and/or treatment setting, including, but not limited to, an office visit, an interaction during hospital rounds, an outpatient or inpatient procedure (surgical or non-surgical), a follow-up evaluation, a visit for laboratory or radiology testing, etc. One method that clinician 120 may use to document the patient encounter may be to enter medical facts that can be ascertained from the patient encounter into user interface 110 as discrete structured data items. The set of medical facts, once entered, may be transmitted in some embodiments via any suitable communication medium or media (e.g., local and/or network connection(s) that may include wired and/or wireless connection(s)) to system 100. Specifically, in some embodiments, the set of medical facts may be received at system 100 by a fact review component 106, exemplary functions of which are described below.

Another method that may be used by clinician 120 to document the patient encounter is to provide a free-form narration of the patient encounter. In some embodiments, the narration may be free-form in the sense that clinician 120 may be unconstrained with regard to the structure and content of the narration, and may be free to provide any sequence of words, sentences, paragraphs, sections, etc., that he would like. In some embodiments, there may be no limitation on the length of the free-form narration, or the length may be limited only by the processing capabilities of the user interface into which it is entered or of the later processing components that will operate upon it. In other embodiments, the free-form narration may be constrained in length (e.g., limited to a particular number of characters).

A free-form narration of the patient encounter may be provided by clinician 120 in any of various ways. One way may be to manually enter the free-form narration in textual form into user interface 110, e.g., using a keyboard. In this respect, the one or more processors of system 100 and/or of a client device in communication with system 100 may in some embodiments be programmed to present a user interface including a text editor/word processor to clinician 120. Such a text editor/word processor may be implemented in any suitable way, as aspects of the present invention are not limited in this respect.

Another way to provide a free-form narration of the patient encounter may be to verbally speak a dictation of the patient encounter. Such a spoken dictation may be provided in any suitable way, as aspects of the present invention are not limited in this respect. As illustrated in FIG. 1, one way that clinician 120 may provide a spoken dictation of the free-form narration may be to speak the dictation into a microphone 112 providing input (e.g., via a direct wired connection, a direct wireless connection, or via a connection through an intermediate device) to user interface 110. An audio recording of the spoken dictation may then be stored in any suitable data format, and transmitted to system 100 and/or to medical transcriptionist 130. Another way that clinician 120 may provide the spoken dictation may be to speak into a telephone 118, from which an audio signal may be transmitted to be recorded at system 100, at the site of medical transcriptionist 130, or at any other suitable location. Alternatively, the audio signal may be recorded in any suitable data format at an intermediate facility, and the audio data may then be relayed to system 100 and/or to medical transcriptionist 130.

In some embodiments, medical transcriptionist 130 may receive the audio recording of the dictation provided by clinician 120, and may transcribe it into a textual representation of the free-form narration (e.g., into a text narrative). Medical transcriptionist 130 may be any human who listens to the audio dictation and writes or types what was spoken into a text document. In some embodiments, medical transcriptionist 130 may be specifically trained in the field of medical transcription, and may be well-versed in medical terminology. In some embodiments, medical transcriptionist 130 may transcribe exactly what she hears in the audio dictation, while in other embodiments, medical transcriptionist 130 may add formatting to the text transcription to comply with generally accepted medical document standards. When medical transcriptionist 130 has completed the transcription of the free-form narration into a textual representation, the resulting text narrative may in some embodiments be transmitted to system 100 or any other suitable location (e.g., to a storage location accessible to system 100). Specifically, in some embodiments the text narrative may be received from medical transcriptionist 130 by fact extraction component 104 within system 100. Exemplary functionality of fact extraction component 104 is described below.

In some other embodiments, the audio recording of the spoken dictation may be received, at system 100 or any other suitable location, by automatic speech recognition (ASR) engine 102. In some embodiments, ASR engine 102 may then process the audio recording to determine what was spoken. As discussed above, such processing may involve any suitable speech recognition technique, as aspects of the present invention are not limited in this respect. In some embodiments, the audio recording may be automatically converted to a textual representation, while in other embodiments, words identified directly from the audio recording may be represented in a data format other than text, or abstract concepts may be identified instead of words. Examples of further processing are described below with reference to a text narrative that is a textual representation of the free-form narration; however, it should be appreciated that similar processing may be performed on other representations of the free-form narration as discussed above. When a textual representation is produced, in some embodiments it may be reviewed by a human (e.g., a transcriptionist) for accuracy, while in other embodiments the output of ASR engine 102 may be accepted as accurate without human review. As discussed above, some embodiments are not limited to any particular method for transcribing audio data; an audio recording of a spoken dictation may be transcribed manually by a human transcriptionist, automatically by ASR, or semi-automatically by human editing of a draft transcription produced by ASR. Transcriptions produced by ASR engine 102 and/or by transcriptionist 130 may be encoded or otherwise represented as data in any suitable form, as aspects of the invention are not limited in this respect.

In some embodiments, ASR engine 102 may make use of a lexicon of medical terms (which may be part of, or in addition to, another more general speech recognition lexicon) while determining the sequence of words that were spoken in the free-form narration provided by clinician 120. However, aspects of the invention are not limited to the use of a lexicon, or any particular type of lexicon, for ASR. When used, the medical lexicon in some embodiments may be linked to a knowledge representation model such as a clinical language understanding ontology utilized by fact extraction component 104, such that ASR engine 102 might produce a text narrative containing terms in a form understandable to fact extraction component 104. In some embodiments, a more general speech recognition lexicon might also be shared between ASR engine 102 and fact extraction component 104. However, in other embodiments, ASR engine 102 may not have any lexicon developed to be in common with fact extraction component 104. In some embodiments, a lexicon used by ASR engine 102 may be linked to a different type of medical knowledge representation model, such as one not designed or used for language understanding. It should be appreciated that any lexicon used by ASR engine 102 and/or fact extraction component 104 may be implemented and/or represented as data in any suitable way, as aspects of the invention are not limited in this respect.

In some embodiments, a text narrative, whether produced by ASR engine 102 (and optionally verified or not by a human), produced by medical transcriptionist 130, directly entered in textual form through user interface 110, or produced in any other way, may be re-formatted in one or more ways before being received by fact extraction component 104. Such re-formatting may be performed by ASR engine 102, by a component of fact extraction component 104, by a combination of ASR engine 102 and fact extraction component 104, or by any other suitable software and/or hardware component. In some embodiments, the re-formatting may be performed in a way known to facilitate fact extraction, and may be performed for the purpose of facilitating the extraction of clinical facts from the text narrative by fact extraction component 104. For example, in some embodiments, processing to perform fact extraction may be improved if sentence boundaries in the text narrative are accurate. Accordingly, in some embodiments, the text narrative may be re-formatted prior to fact extraction to add, remove or correct one or more sentence boundaries within the text narrative. In some embodiments, this may involve altering the punctuation in at least one location within the text narrative. In another example, fact extraction may be improved if the text narrative is organized into sections with headings, and thus the re-formatting may include determining one or more section boundaries in the text narrative and adding, removing or correcting one or more corresponding section headings. In some embodiments, the re-formatting may include normalizing one or more section headings (which may have been present in the original text narrative and/or added or corrected as part of the re-formatting) according to a standard for the healthcare institution corresponding to the patient encounter (which may be an institution-specific standard or a more general standard for section headings in clinical documents). In some embodiments, a user (such as clinician 120, medical transcriptionist 130, or another user) may be prompted to approve the re-formatted text.

In some embodiments, either an original or a re-formatted text narrative may be received by fact extraction component 104, which may perform processing to extract one or more medical facts (e.g., clinical facts) from the text narrative. The text narrative may be received from ASR engine 102, from medical transcriptionist 130, directly from clinician 120 via user interface 110, or in any other suitable way. Any suitable technique(s) for extracting facts from the text narrative may be used, as aspects of the present invention are not limited in this respect. Exemplary techniques for medical fact extraction are described below.

In some embodiments, a fact extraction component may be implemented using techniques such as those described in U.S. Pat. No. 7,493,253, entitled "Conceptual World Representation Natural Language Understanding System and Method." U.S. Pat. No. 7,493,253 is incorporated herein by reference in its entirety. Such a fact extraction component may make use of a formal ontology linked to a lexicon of clinical terms. The formal ontology may be implemented as a relational database, or in any other suitable form, and may represent semantic concepts relevant to the medical domain, as well as linguistic concepts related to ways the semantic concepts may be expressed in natural language.

In some embodiments, concepts in a formal ontology used by a fact extraction component may be linked to a lexicon of medical terms and/or codes, such that each medical term and each code is linked to at least one concept in the formal ontology. In some embodiments, the lexicon may include the standard medical terms and/or codes used by the institution in which the fact extraction component is applied. For example, the standard medical terms and/or codes used by an EHR maintained by the institution may be included in the lexicon linked to the fact extraction component's formal ontology. In some embodiments, the lexicon may also include additional medical terms used by the various clinicians within the institution, and/or used by clinicians generally, when describing medical issues in a free-form narration. Such additional medical terms may be linked, along with their corresponding standard medical terms, to the appropriate shared concepts within the formal ontology. For example, the standard term "acute myocardial infarction" as well as other corresponding terms such as "heart attack", "acute MI" and "AMI" may all be linked to the same abstract concept in the formal ontology—a concept representing an interruption of blood supply to the heart. Such linkage of multiple medical terms to the same abstract concept in some embodiments may relieve the clinician of the burden of ensuring that only standard medical terms preferred by the institution appear in the free-form narration. For example, in some embodiments, a clinician may be free to use the abbreviation "AMI" or the colloquial "heart attack" in his free-form narration, and the shared concept linkage may allow the fact extraction component to nevertheless automatically extract a fact corresponding to "acute myocardial infarction".

In some embodiments, a formal ontology used by a fact extraction component may also represent various types of relationships between the concepts represented. One type of relationship between two concepts may be a parent-child relationship, in which the child concept is a more specific version of the parent concept. More formally, in a parent-child relationship, the child concept inherits all necessary properties of the parent concept, while the child concept may have necessary properties that are not shared by the parent concept. For example, "heart failure" may be a parent concept, and "congestive heart failure" may be a child concept of "heart failure." In some embodiments, any other type(s) of relationship useful to the process of medical documentation may also be represented in the formal ontology. For example, one type of relationship may be a symptom relationship. In one example of a symptom relationship, a concept linked to the term "chest pain" may have a relationship of "is-symptom-of" to the concept linked to the term "heart attack". Other types of relationships may include complication relationships, comorbidity relationships, interaction relationships (e.g., among medications), and many others. Any number and type(s) of concept relationships may be included in such a formal ontology, as aspects of the present invention are not limited in this respect.

In some embodiments, automatic extraction of medical facts from a clinician's free-form narration may involve parsing the free-form narration to identify medical terms that are represented in the lexicon of the fact extraction component. Concepts in the formal ontology linked to the medical terms that appear in the free-form narration may then be identified, and concept relationships in the formal ontology may be traced to identify further relevant concepts. Through these relationships, as well as the linguistic knowledge represented in the formal ontology, one or more medical facts may be extracted. For example, if the free-form narration includes the medical term "hypertension" and the linguistic context relates to the patient's past, the fact extraction component may automatically extract a fact indicating that the patient has a history of hypertension. On the other hand, if the free-form narration includes the medical term "hypertension" in a sentence about the patient's mother, the fact extraction component may automatically extract a fact indicating that the patient has a family history of hypertension. In some embodiments, relationships between concepts in the formal ontology may also allow the fact extraction component to automatically extract facts containing medical terms that were not explicitly included in the free-form narration. For example, the medical term "meningitis" can also be described as inflammation in the brain. If the free-form narration includes the terms "inflammation" and "brain" in proximity to each other, then relationships in the formal ontology between concepts linked to the terms "inflammation", "brain" and "meningitis" may allow the fact extraction component to automatically extract a fact corresponding to "meningitis", despite the fact that the term "meningitis" was not stated in the free-form narration.

It should be appreciated that the foregoing descriptions are provided by way of example only, and that any suitable technique(s) for extracting a set of one or more medical facts from a free-form narration may be used, as aspects of the present invention are not limited to any particular fact extraction technique. For instance, it should be appreciated that fact extraction component 104 is not limited to the use of an ontology, as other forms of knowledge representation models, including statistical models and/or rule-based models, may also be used. The knowledge representation model may also be represented as data in any suitable format, and may be stored in any suitable location, such as in a storage medium of system 100 accessible by fact extraction component 104, as aspects of the invention are not limited in this respect. In addition, a knowledge representation model such as an ontology used by fact extraction component 104 may be constructed in any suitable way, as aspects of the invention are not limited in this respect.

For instance, in some embodiments a knowledge representation model may be constructed manually by one or more human developers with access to expert knowledge about medical facts, diagnoses, problems, potential complications, comorbidities, appropriate observations and/or clinical findings, and/or any other relevant information. In other embodiments, a knowledge representation model may be generated automatically, for example through statistical analysis of past medical reports documenting patient encounters, of medical literature and/or of other medical documents. Thus, in some embodiments, fact extraction component 104 may have access to a data set 170 of medical literature and/or other documents such as past patient encounter reports. In some embodiments, past reports and/or other text documents may be marked up (e.g., by a human) with labels indicating the nature of the relevance of particular statements in the text to the patient encounter or medical topic to which the text relates. A statistical knowledge representation model may then be trained to form associations based on the prevalence of particular labels corresponding to similar text within an aggregate set of multiple marked up documents. For example, if "pneumothorax" is labeled as a "complication" in a large enough proportion of clinical procedure reports documenting pacemaker implantation procedures, a statistical knowledge representation model may generate and store a concept relationship that "pneumothorax is-complication-of pacemaker implantation." In some embodiments, automatically generated and hard coded (e.g., by a human developer) concepts and/or relationships may both be included in a knowledge representation model used by fact extraction component 104.

As discussed above, it should be appreciated that aspects of the invention are not limited to any particular technique(s) for constructing knowledge representation models. Examples of suitable techniques include those disclosed in the following:

Gómez-Pérez, A., and Manzano-Macho, D. (2005). *An overview of methods and tools for ontology learning from texts*. Knowledge Engineering Review 19, p. 187-212.

Cimiano, P., and Staab, S. (2005). *Learning concept hierarchies from text with a guided hierarchical clustering algorithm*. In C. Biemann and G. Paas (eds.), Proceedings of the ICML 2005 Workshop on Learning and Extending Lexical Ontologies with Machine Learning Methods, Bonn, Germany.

Fan, J., Ferrucci, D., Gondek, D., and Kalyanpur, A. (2010). *PRISMATIC: Inducing Knowledge from a Lange Scale Lexicalized Relation Resource*. NAACL Workshop on Formalisms and Methodology for Learning by Reading.

Welty, C., Fan, J., Gondek, D. and Schlaikjer, A. (2010). *Large scale relation detection*. NAACL Workshop on Formalisms and Methodology for Learning by Reading.

Each of the foregoing publications is incorporated herein by reference in its entirety.

Alternatively or additionally, in some embodiments a fact extraction component may make use of one or more statistical models to extract semantic entities from natural language input. In general, a statistical model can be described as a functional component designed and/or trained to analyze new inputs based on probabilistic patterns observed in prior training inputs. In this sense, statistical models differ from "rule-based" models, which typically apply hard-coded deterministic rules to map from inputs having particular characteristics to particular outputs. By contrast, a statistical model may operate to determine a particular output for an input with particular characteristics by considering how often (e.g., with what probability) training inputs with those same characteristics (or similar characteristics) were associated with that particular output in the statistical model's training data. To supply the probabilistic data that allows a statistical model to extrapolate from the tendency of particular input characteristics to be associated with particular outputs in past examples, statistical models are typically trained (or "built") on large training corpuses with great numbers of example inputs. Typically the example inputs are labeled with the known outputs with which they should be associated, usually by a human labeler with expert knowledge of the domain. Characteristics of interest (known as "features") are identified ("extracted") from the inputs, and the statistical model learns the probabilities with which different features are associated with different outputs, based on how often training inputs with those features are associated with those outputs. When the same features are extracted from a new input (e.g., an input that has not been labeled with a known output by a human), the statistical model can then use the learned probabilities for the extracted features (as learned from the training data) to determine which output is most likely correct for the new input. Exemplary implementations of a fact extraction component using one or more statistical models are described further below.

In some embodiments, fact extraction component 104 may utilize a statistical fact extraction model based on entity detection and/or tracking techniques, such as those disclosed in: Florian, R., Hassan, H., Ittycheriah, A., Jing, H., Kambhatla, N., Luo, X., Nicolov, N., and Roukos, S. (2004). *A Statistical Model for Multilingual Entity Detection and Tracking*. Proceedings of the Human Language Technologies Conference 2004 (HLT-NAACL'04). This publication is incorporated herein by reference in its entirety.

For example, in some embodiments, a list of fact types of interest for generating medical reports may be defined, e.g., by a developer of fact extraction component 104. Such fact types (also referred to herein as "entity types") may include, for example, problems, disorders (a disorder is a type of problem), diagnoses (a diagnosis may be a disorder that a clinician has identified as a problem for a particular patient), findings (a finding is a type of problem that need not be a disorder), medications, body sites, social history facts, allergies, diagnostic test results, vital signs, procedures, procedure steps, observations, devices, and/or any other suitable medical fact types. It should be appreciated that any suitable list of fact types may be utilized, and may or may not include any of the fact types listed above, as aspects of the invention are not limited in this respect. In some embodiments, spans of text in a set of sample patient encounter reports may be labeled (e.g., by a human) with appropriate fact types from the list. A statistical model may then be trained on the corpus of labeled sample reports to detect and/or track such fact types as semantic entities, using entity detection and/or tracking techniques, examples of which are described below.

For example, in some embodiments, a large number of past free-form narrations created by clinicians may be manually labeled to form a corpus of training data for a statistical entity detection model. As discussed above, in some embodiments, a list of suitable entities may be defined (e.g., by a domain administrator) to include medical fact types that are to be extracted from future clinician narrations. One or more human labelers (e.g., who may have specific knowledge about medical information and typical clinician narration content) may then manually label portions of the training texts with the particular defined entities to which they correspond. For example, given the training text, "Patient is complaining of acute sinusitis," a human labeler may label the text portion "acute sinusitis" with the entity label "Problem." In another example, given the training text, "He has sinusitis, which appears to be chronic," a human labeler may label the text "sinusitis" and "chronic" with a single label indicating that both words together correspond to a "Problem" entity. As should be clear from these examples, the portion of the text labeled as corresponding to a single conceptual entity need not be formed of contiguous words, but may have words split up within the text, having non-entity words in between.

In some embodiments, the labeled corpus of training data may then be processed to build a statistical model trained to detect mentions of the entities labeled in the training data. Each time the same conceptual entity appears in a text, that appearance is referred to as a mention of that entity. For example, consider the text, "Patient has sinusitis. His sinusitis appears to be chronic." In this example, the entity detection model may be trained to identify each appearance of the word "sinusitis" in the text as a separate mention of the same "Problem" entity.

In some embodiments, the process of training a statistical entity detection model on labeled training data may involve a number of steps to analyze each training text and probabilistically associate its characteristics with the corresponding entity labels. In some embodiments, each training text (e.g., free-form clinician narration) may be tokenized to break it down into various levels of syntactic substructure. For example, in some embodiments, a tokenizer module may be implemented to designate spans of the text as representing structural/syntactic units such as document sections, paragraphs, sentences, clauses, phrases, individual tokens, words, sub-word units such as affixes, etc. In some embodiments, individual tokens may often be single words, but some tokens may include a sequence of more than one word that is defined, e.g., in a dictionary, as a token. For example, the term "myocardial infarction" could be defined as a token, although it is a sequence of more than one word. In some embodiments, a token's identity (i.e., the word or sequence of words itself) may be used as a feature of that token. In some embodiments, the token's placement within particular syntactic units in the text (e.g., its section, paragraph, sentence, etc.) may also be used as features of the token.

In some embodiments, an individual token within the training text may be analyzed (e.g., in the context of the surrounding sentence) to determine its part of speech (e.g., noun, verb, adjective, adverb, preposition, etc.), and the token's part of speech may be used as a further feature of that token. In some embodiments, each token may be tagged with its part of speech, while in other embodiments, not every token may be tagged with a part of speech. In some embodiments, a list of relevant parts of speech may be pre-defined, e.g., by a developer of the statistical model, and any token having a part of speech listed as relevant may be tagged with that part of speech. In some embodiments, a parser module may be implemented to determine the syntactic structure of sentences in the text, and to designate positions within the sentence structure as features of individual tokens. For example, in some embodiments, the fact that a token is part of a noun phrase or a verb phrase may be used as a feature of that token. Any type of parser may be used, non-limiting examples of which include a bottom-up parser and/or a dependency parser, as aspects of the invention are not limited in this respect.

In some embodiments, section membership may be used as a feature of a token. In some embodiments, a section normalization module may be implemented to associate various portions of the narrative text with the proper section to which it should belong. In some embodiments, a set of standardized section types (e.g., identified by their section headings) may be defined for all texts, or a different set of normalized section headings may be defined for each of a number of different types of texts (e.g., corresponding to different types of documents). For example, in some embodiments, a different set of normalized section headings may be defined for each type of medical document in a defined set of medical document types. Non-limiting examples of medical document types include consultation reports, history & physical reports, discharge summaries, and emergency room reports, although there are also many other examples. In the medical field, the various types of medical documents are often referred to as "work types." In some cases, the standard set of sections for various types of medical documents may be established by a suitable system standard, institutional standard, or more widely applicable standard, such as the Meaningful Use standard (discussed above) or the Logical Observation Identifiers Names and Codes (LOINC) standard maintained by the Regenstrief Institute. For example, an expected set of section headings for a history & physical report under the Meaningful Use standard may include headings for a "Reason for Visit" section, a "History of Present Illness" section, a "History of Medication Use" section, an "Allergies, Adverse Reactions and Alerts" section, a "Review of Systems" section, a "Social History" section, a "Physical Findings" section, an "Assessment and Plan" section, and/or any other suitable section(s). Any suitable set of sections may be used, however, as aspects of the invention are not limited in this respect.

A section normalization module may use any suitable technique to associate portions of text with normalized document sections, as aspects of the invention are not limited in this respect. In some embodiments, the section normalization module may use a table (e.g., stored as data in a storage medium) to map text phrases that commonly occur in medical documents to the sections to which they should belong. In another example, a statistical model may be trained to determine the most likely section for a portion of text based on its semantic content, the semantic content of surrounding text portions, and/or the expected semantic content of the set of normalized sections. In some embodiments, once a normalized section for a portion of text has been identified, the membership in that section may be used as a feature of one or more tokens in that portion of text.

In some embodiments, other types of features may be extracted, i.e., identified and associated with tokens in the training text. For example, in some embodiments, an N-gram feature may identify the previous (N−1) words and/or tokens in the text as a feature of the current token. In another example, affixes (e.g., suffixes such as -ectomy, -oma, -itis, etc.) may be used as features of tokens. In another example, one or more predefined dictionaries and/or ontologies may be accessed, and a token's membership in any of those dictionaries may be used as a feature of that token. For example, a predefined dictionary of surgical procedures may be accessed, and/or a dictionary of body sites, and/or a dictionary of known diseases, etc. It should be appreciated, however, that all of the foregoing feature types are merely examples, and any suitable number and/or types of features of interest may be designated, e.g., by a developer of the statistical entity detection model, as aspects of the invention are not limited in this respect.

In some embodiments, the corpus of training text with its hand-labeled fact type entity labels, along with the collection of features extracted for tokens in the text, may be input to the statistical entity detection model for training. As discussed above, examples of suitable features include position within document structure, syntactic structure, parts of speech, parser features, N-gram features, affixes (e.g., prefixes and/or suffixes), membership in dictionaries (sometimes referred to as "gazetteers") and/or ontologies, surrounding token contexts (e.g., a certain number of tokens to the left and/or right of the current token), orthographic features (e.g., capitalization, letters vs. numbers, etc.), entity labels assigned to previous tokens in the text, etc. As one non-limiting example, consider the training sentence, "Patient is complaining of acute sinusitis," for which the word sequence "acute sinusitis" was hand-labeled as being a "Problem" entity. In one exemplary implementation, features extracted for the token "sinusitis" may include the token identity feature that the word is "sinusitis," a syntactic feature specifying that the token occurred at the end of a sentence (e.g., followed by a period), a part-of-speech feature of "noun," a parser feature that the token is part of a noun phrase ("acute sinusitis"), a trigram feature that the two preceding words are "of acute," an affix feature of "-itis," and a dictionary feature that the token is a member of a predefined dictionary of types of inflammation. It should be appreciated, however, that the foregoing list of features is merely exemplary, as any suitable features may be used. Aspects of the invention are not limited to any of the features listed above, and implementations including some, all, or none of the above features, as well as implementations including features not listed above, are possible.

In some embodiments, given the extracted features and manual entity labels for the entire training corpus as input, the statistical entity detection model may be trained to be able to probabilistically label new texts (e.g., texts not included in the training corpus) with automatic entity labels using the same feature extraction technique that was applied to the training corpus. In other words, by processing the input features and manual entity labels of the training corpus, the statistical model may learn probabilistic relationships between the features and the entity labels. When later presented with an input text without manual entity labels, the statistical model may then apply the same feature extraction techniques to extract features from the input text, and may apply the learned probabilistic relationships to automatically determine the most likely entity labels for word sequences in the input text. Any suitable statistical modeling technique may be used to learn such probabilistic relationships, as aspects of the invention are not limited in this respect. Non-limiting examples of suitable known statistical modeling techniques include machine learning techniques such as maximum entropy modeling, support vector machines, and conditional random fields, among others.

In some embodiments, training the statistical entity detection model may involve learning, for each extracted feature, a probability with which tokens having that feature are associated with each entity type. For example, for the suffix feature "-itis," the trained statistical entity detection model may store a probability $p1$ that a token with that feature should be labeled as being part of a "Problem" entity, a probability $p2$ that a token with that feature should be labeled as being part of a "Medication" entity, etc. In some embodiments, such probabilities may be learned by determining the frequency with which tokens having the "-itis" feature were hand-labeled with each different entity label in the training corpus. In some embodiments, the probabilities may be normalized such that, for each feature, the probabilities of being associated with each possible entity (fact type) may sum to 1. However, aspects of the invention are not limited to such normalization. In some embodiments, each feature may also have a probability $p0$ of not being associated with any fact type, such that the non-entity probability $p0$ plus the probabilities of being associated with each possible fact type sum to 1 for a given feature. In other embodiments, separate classifiers may be trained for each fact type, and the classifiers may be run in parallel. For example, the "-itis" feature may have probability p1 of being part of a "Problem" entity and probability (1−p1) of not being part of a "Problem" entity, probability p2 of being part of a "Medication" entity and probability (1−p2) of not being part of a "Medication" entity, and so on. In some embodiments, training separate classifiers may allow some word sequences to have a non-zero probability of being labeled with more than one fact type simultaneously; for example, "kidney failure" could be labeled as representing both a Body Site and a Problem. In some embodiments, classifiers may be trained to identify sub-portions of an entity label. For example, the feature "-itis" could have a probability $p_B$ of its token being at the beginning of a "Problem" entity label, a probability $p_I$ of its token being inside a "Problem" entity label (but not at the beginning of the label), and a probability $P_O$ of its token being outside a "Problem" entity label (i.e., of its token not being part of a "Problem" entity).

In some embodiments, the statistical entity detection model may be further trained to weight the individual features of a token to determine an overall probability that it should be associated with a particular entity label. For example, if the token "sinusitis" has n extracted features f1 ... fn having respective probabilities p1 ... pn of being associated with a "Problem" entity label, the statistical model may be trained to apply respective weights w1 ... wn to the feature probabilities, and then combine the weighted feature probabilities in any suitable way to determine the overall probability that "sinusitis" should be part of a "Problem" entity. Any suitable technique for determining such weights may be used, including known modeling techniques such as maximum entropy modeling, support vector machines, conditional random fields, and/or others, as aspects of the invention are not limited in this respect.

In some embodiments, when an unlabeled text is input to the trained statistical entity detection model, the model may process the text to extract features and determine probabilities for individual tokens of being associated with various entity (e.g., fact type) labels. In some embodiments, the most probable label (including the non-entity label, if it is most probable) may be selected for each token in the input text. In other embodiments, labels may be selected through more contextual analysis, such as at the phrase level or sentence level, rather than at the token level. Any suitable technique, such as Viterbi techniques, or any other suitable technique, may be used, as aspects of the invention are not limited in this respect. In some embodiments, a lattice may be constructed of the associated probabilities for all entity types for all tokens in a sentence, and the best (e.g., highest combined probability) path through the lattice may be selected to determine which word sequences in the sentence are to be automatically labeled with which entity (e.g., fact type) labels. In some embodiments, not only the best path may be identified, but also the (N−1)-best alternative paths with the next highest associated probabilities. In some embodiments, this may result in an N-best list of alternative hypotheses for fact type labels to be associated with the same input text.

In some embodiments, a statistical model may also be trained to associate fact types extracted from new reports with particular facts to be extracted from those reports (e.g., to determine a particular concept represented by the text portion that has been labeled as an entity mention). For example, in some embodiments, a statistical fact extraction model may be applied to automatically label "acute sinusitis" not only with the "Problem" entity (fact type) label, but also with a label indicating the particular medical fact (e.g., concept) indicated by the word sequence (e.g., the medical fact "sinusitis, acute"). In such embodiments, for example, a single statistical model may be trained to detect specific particular facts as individual entities. For example, in some embodiments, the corpus of training text may be manually labeled by one or more human annotators with labels indicating specific medical facts, rather than labels indicating more general entities such as fact types or categories. However, in other embodiments, the process of detecting fact types as entities may be separated from the process of relating detected fact types to particular facts. For example, in some embodiments, a separate statistical model (e.g., an entity detection model) may be trained to automatically label portions of text with fact type labels, and another separate statistical model (e.g., a relation model) may be trained to identify which labeled entity (fact type) mentions together indicate a single specific medical fact. In some cases, the relation model may identify particular medical facts by relating together two or more mentions labeled with the same entity type.

For example, in the text, "Patient is complaining of acute sinusitis," in some embodiments an entity detection model may label the tokens "acute" and "sinusitis" as being part of a "Problem" entity. In some embodiments, a relation model, given that "acute" and "sinusitis" have been labeled as "Problem," may then relate the two tokens together to a single medical fact of "sinusitis, acute." For another example, consider the text, "Patient has sinusitis, which appears to be chronic." In some embodiments, an entity detection model may be applied to label the tokens "sinusitis" and "chronic" as "Problem" entity mentions. In some embodiments, a relation model may then be applied to determine that the two "Problem" entity mentions "sinusitis" and "chronic" are related (even though they are not contiguous in the text) to represent a single medical fact of "sinusitis, chronic." For yet another example, consider the text, "She has acute sinusitis; chronic attacks of asthma may be a factor." In some embodiments, an entity detection model may label each of the tokens "acute," "sinusitis," "chronic," and "asthma" as belonging to "Problem" entity mentions. In some embodiments, a relation model may then be applied to determine which mentions relate to the same medical fact. For example, the relation model may determine that the tokens "acute" and "sinusitis" relate to a first medical fact (e.g., "sinusitis, acute"), while the tokens "chronic" and "asthma" relate to a different medical fact (e.g., "asthma, chronic"), even though the token "chronic" is closer in the sentence to the token "sinusitis" than to the token "asthma."

In some embodiments, a relation model may be trained statistically using methods similar to those described above for training the statistical entity detection model. For example, in some embodiments, training texts may be manually labeled with various types of relations between entity mentions and/or tokens within entity mentions. For example, in the training text, "Patient has sinusitis, which appears to be chronic," a human annotator may label the "Problem" mention "chronic" as having a relation to the "Problem" mention "sinusitis," since both mentions refer to the same medical fact. In some embodiments, the relation annotations may simply indicate that certain mentions are related to each other, without specifying any particular type of relationship. In other embodiments, relation annotations may also indicate specific types of relations between entity mentions. Any suitable number and/or types of relation annotations may be used, as aspects of the invention are not limited in this respect. For example, in some embodiments, one type of relation annotation may be a "split" relation label. The tokens "sinusitis" and "chronic," for example, may be labeled as having a split relationship, because "sinusitis" and "chronic" together make up an entity, even though they are not contiguous within the text. In this case, "sinusitis" and "chronic" together indicate a specific type of sinusitis fact, i.e., one that it is chronic and not, e.g., acute. Another exemplary type of relation may be an "attribute" relation. In some embodiments, one or more system developers may define sets of attributes for particular fact types, corresponding to related information that may be specified for a fact type. For example, a "Medication" fact type may have attributes "dosage," "route," "frequency," "duration," etc. In another example, an "Allergy" fact type may have attributes "allergen," "reaction," "severity," etc. It should be appreciated, however, that the foregoing are merely examples, and that aspects of the invention are not limited to any particular attributes for any particular fact types. Also, other types of fact relations are possible, including family relative relations, causes-problem relations, improves-problem relations, and many others. Aspects of the invention are not limited to use of any particular relation types.

In some embodiments, using techniques similar to those described above, the labeled training text may be used as input to train the statistical relation model by extracting features from the text, and probabilistically associating the extracted features with the manually supplied labels. Any suitable set of features may be used, as aspects of the invention are not limited in this respect. For example, in some embodiments, features used by a statistical relation model may include entity (e.g., fact type) labels, parts of speech, parser features, N-gram features, token window size (e.g., a count of the number of words or tokens present between two tokens that are being related to each other), and/or any other suitable features. It should be appreciated, however, that the foregoing features are merely exemplary, as embodiments are not limited to any particular list of features. In some embodiments, rather than outputting only the best (e.g., most probable) hypothesis for relations between entity mentions, a statistical relation model may output a list of multiple alternative hypotheses, e.g., with corresponding probabilities, of how the entity mentions labeled in the input text are related to each other. In yet other embodiments, a relation model may be hard-coded and/or otherwise rule-based, while the entity detection model used to label text portions with fact types may be trained statistically.

In some embodiments, the relation model or another statistical model may also be trained to track mentions of the same entity from different sentences and/or document sections and to relate them together. Exemplary techniques for entity tracking are described in the publication by Florian cited above.

In some embodiments, further processing may be applied to normalize particular facts extracted from the text to standard forms and/or codes in which they are to be documented. For example, medical personnel often have many different ways of phrasing the same medical fact, and a normalization/coding process in some embodiments may be applied to identify the standard form and/or code corresponding to each extracted medical fact that was stated in a non-standard way. The standard form and/or code may be derived from any suitable source, as aspects of the invention are not limited in this respect. Some standard terms and/or codes may be derived from a government or profession-wide standard, such as SNOMED (Systematized Nomenclature of Medicine), UMLS (Unified Medical Language System), RxNorm, RadLex, etc. Other standard terms and/or codes may be more locally derived, such as from standard practices of a particular locality or institution. Still other standard terms and/or codes may be specific to the documentation system including the fact extraction component being applied.

For example, given the input text, "His sinuses are constantly inflamed," in some embodiments, an entity detection model together with a relation model (or a single model performing both functions) may identify the tokens "sinuses," "constantly" and "inflamed" as representing a medical fact. In some embodiments, a normalization/coding process may then be applied to identify the standard form for documenting "constantly inflamed sinuses" as "sinusitis, chronic." Alternatively or additionally, in some embodiments the normalization/coding process may identify a standard code used to document the identified fact. For example, the ICD-9 code for "sinusitis, chronic" is ICD-9 code #473. Any suitable coding system may be used, as aspects of the invention are not limited in this respect. Exemplary standard codes include ICD (International Classification of Diseases) codes, CPT (Current Procedural Terminology) codes, E&M (Evaluation and Management) codes, MedDRA (Medical Dictionary for Regulatory Activities) codes, SNOMED codes, LOINC (Logical Observation Identifiers Names and Codes) codes, RxNorm codes, NDC (National Drug Code) codes and RadLex codes.

In some embodiments, a normalization/coding process may be rule-based (e.g., using lists of possible ways of phrasing particular medical facts, and/or using an ontology of medical terms and/or other language units to normalize facts extracted from input text to their standard forms). For example, in some embodiments, the tokens identified in the text as corresponding to a medical fact may be matched to corresponding terms in an ontology. In some embodiments, a list of closest matching terms may be generated, and may be ranked by their similarity to the tokens in the text. The similarity may be scored in any suitable way. For example, in one suitable technique, one or more tokens in the text may be considered as a vector of its component elements, such as words, and each of the terms in the ontology may also be considered as a vector of component elements such as words. Similarity scores between the tokens may then be computed by comparing the corresponding vectors, e.g., by calculating the angle between the vectors, or a related measurement such as the cosine of the angle. In some embodiments, one or more concepts that are linked in the ontology to one or more of the higher ranking terms (e.g., the terms most similar to the identified tokens in the text) may then be identified as hypotheses for the medical fact to be extracted from that portion of the text. Exemplary techniques that may be used in some embodiments are described in Salton, Wong, & Yang: "A vector space model for automatic indexing," Communications of the ACM, November 1975. This publication is incorporated herein by reference in its entirety. However, these are merely examples, and any suitable technique(s) for normalizing entity tokens to standard terms may be utilized in some embodiments, as aspects of the invention are not limited in this respect.

In some embodiments, the normalization/coding process may output a single hypothesis for the standard form and/or code corresponding to each extracted fact. For example, the single output hypothesis may correspond to the concept linked in the ontology to the term that is most similar to the token(s) in the text from which the fact is extracted. However, in other embodiments, the normalization/coding process may output multiple alternative hypotheses, e.g., with corresponding probabilities, for the standard form and/or code corresponding to an individual extracted fact. Thus, it should be appreciated that in some embodiments multiple alternative hypotheses for a medical fact to be extracted from a portion of input text may be identified by fact extraction component 104. Such alternative hypotheses may be collected at any or all of various processing levels of fact extraction, including entity detection, entity relation, and/or normalization/coding stages. In some embodiments, the list of alternative hypotheses may be thresholded at any of the various levels, such that the final list output by fact extraction component 104 may represent the N-best alternative hypotheses for a particular medical fact to be extracted.

It should be appreciated that the foregoing are merely examples, and that fact extraction component 104 may be implemented in any suitable way and/or form, as aspects of the invention are not limited in this respect.

In some embodiments, a user such as clinician 120 may monitor, control and/or otherwise interact with the fact extraction and/or fact review process through a user interface provided in connection with system 100. For example, in some embodiments, user interface 140 may be provided by fact review component 106, e.g., through execution (e.g., by one or more processors of system 100) of programming instructions incorporated in fact review component 106. One exemplary implementation of such a user interface is graphical user interface (GUI) 200, illustrated in FIG. 2. In some embodiments, when the user is clinician 120, GUI 200 may be presented via user interface 110. In some embodiments, a user may be a person other than a clinician; for example, another person such as coding specialist 150 may be presented with GUI 200 via user interface 140. However, it should be appreciated that "user," as used herein, refers to an end user of system 100, as opposed to a software and/or hardware developer of any component of system 100.

The user interface is not limited to a graphical user interface, as other ways of providing data from system 100 to users may be used. For example, in some embodiments, audio indicators may be transmitted from system 100 and conveyed to a user. It should be appreciated that any type of user interface may be provided in connection with fact extraction, fact review and/or other related processes, as aspects of the invention are not limited in this respect. While the exemplary embodiments illustrated in FIG. 1 involve data processing at system 100 and data communication between system 100 and user interfaces 110 and/or 140, it should be appreciated that in other embodiments any or all processing components of system 100 may instead be implemented locally at user interface 110 and/or user interface 140, as aspects of the invention are not limited to any particular distribution of local and/or remote processing capabilities.

Figure 2:
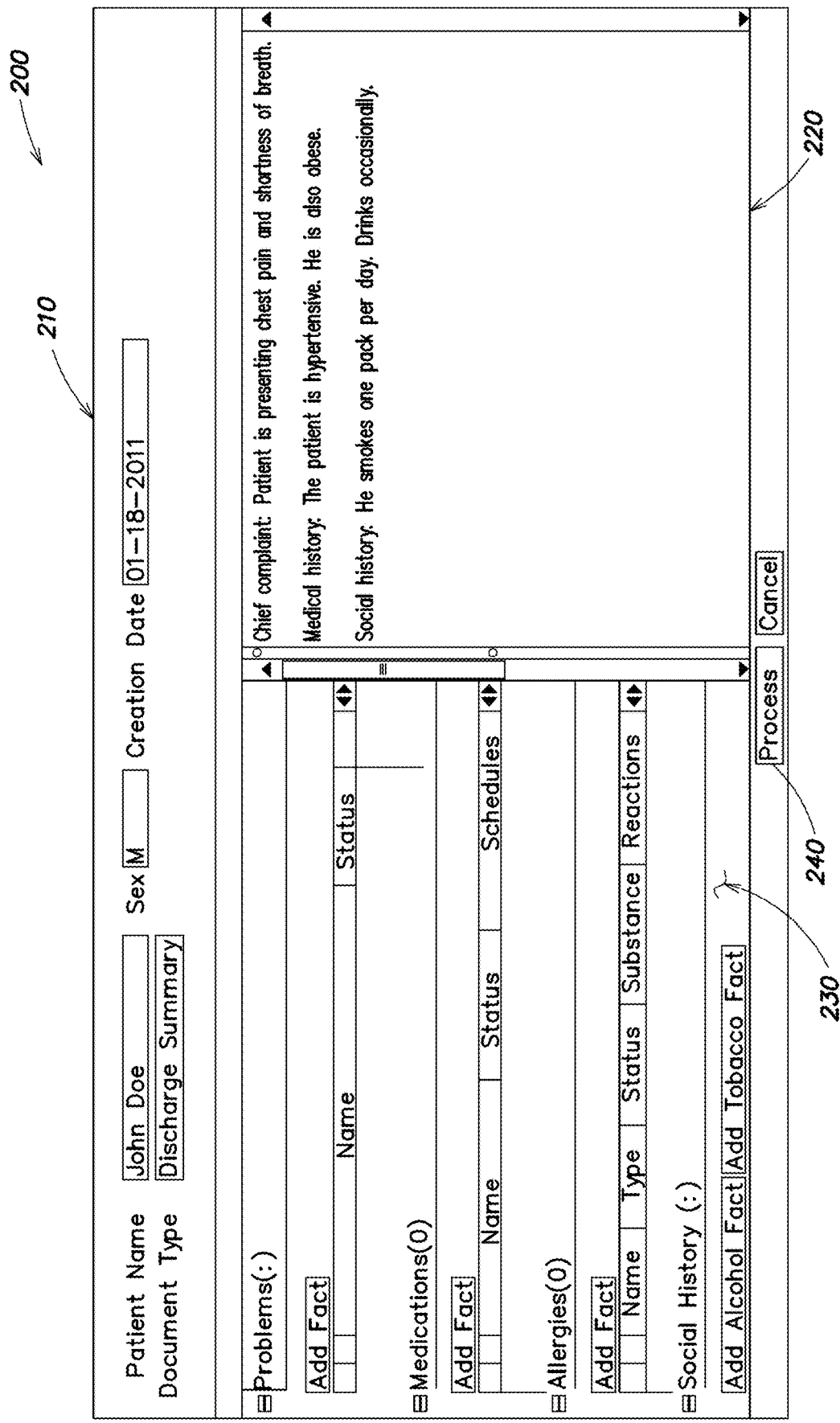
FIG. 2 is a screenshot illustrating an exemplary graphical user interface for review of extracted medical facts in accordance with some embodiments.

As depicted in FIG. 2, GUI 200 includes a number of separate panes displaying different types of data. Identifying information pane 210 includes general information identifying patient 222 as a male patient named John Doe. Such general patient identifying information may be entered by clinician 120, or by other user 150, or may be automatically populated from an electronic medical record for patient 122, or may be obtained from any other suitable source. Identifying information pane 210 also displays the creation date and document type of the report currently being worked on. This information may also be obtained from any suitable source, such as from stored data or by manual entry. When referring herein to entry of data by clinician 120 and/or other user 150, it should be appreciated that any suitable form of data entry may be used, including input via mouse, keyboard, touchscreen, stylus, voice, or any other suitable input form, as aspects of the invention are not limited in this respect.

GUI 200 as depicted in FIG. 2 includes a text panel 220 in which a text narrative referring to the encounter between clinician 120 and patient 122 is displayed. In some embodiments, text panel 220 may include text editor functionality, such that clinician 120 may directly enter the text narrative into text panel 220, either during the patient encounter or at some time thereafter. If ASR is used to produce the text narrative from a spoken dictation provided by clinician 120, in some embodiments the text may be displayed in text panel 220 as it is produced by ASR engine 102, either in real time while clinician 120 is dictating, or with a larger processing delay. In other embodiments, the text narrative may be received as stored data from another source, such as from medical transcriptionist 130, and may be displayed in completed form in text panel 220. In some embodiments, the text narrative may then be edited if desired by clinician 120 and/or other user 150 within text panel 220. However, text editing capability is not required, and in some embodiments text panel 220 may simply display the text narrative without providing the ability to edit it.

Exemplary GUI 200 further includes a fact panel 230 in which one or more medical facts, once extracted from the text narrative and/or entered in another suitable way, may be displayed as discrete structured data items. When clinician 120 and/or other user 150 is ready to direct fact extraction component 104 to extract one or more medical facts from the text narrative, in some embodiments he or she may select process button 240 via any suitable selection input method. However, a user indication to begin fact extraction is not limited to a button such as process button 240, as any suitable way to make such an indication may be provided by GUI 200. In some embodiments, no user indication to begin fact extraction may be required, and fact extraction component 104 may begin a fact extraction process as soon as a requisite amount of text (e.g., enough text for fact extraction component 104 to identify one or more clinical facts that can be ascertained therefrom) is entered and/or received. In some embodiments, a user may select process button 240 to cause fact extraction to be performed before the text narrative is complete. For example, clinician 120 may dictate, enter via manual input and/or otherwise provide a part of the text narrative, select process button 240 to have one or more facts extracted from that part of the text narrative, and then continue to provide further part(s) of the text narrative. In another example, clinician 120 may provide all or part of the text narrative, select process button 240 and review the resulting extracted facts, edit the text narrative within text pane 220, and then select process button 240 again to review how the extracted facts may change.

Figure 3B:
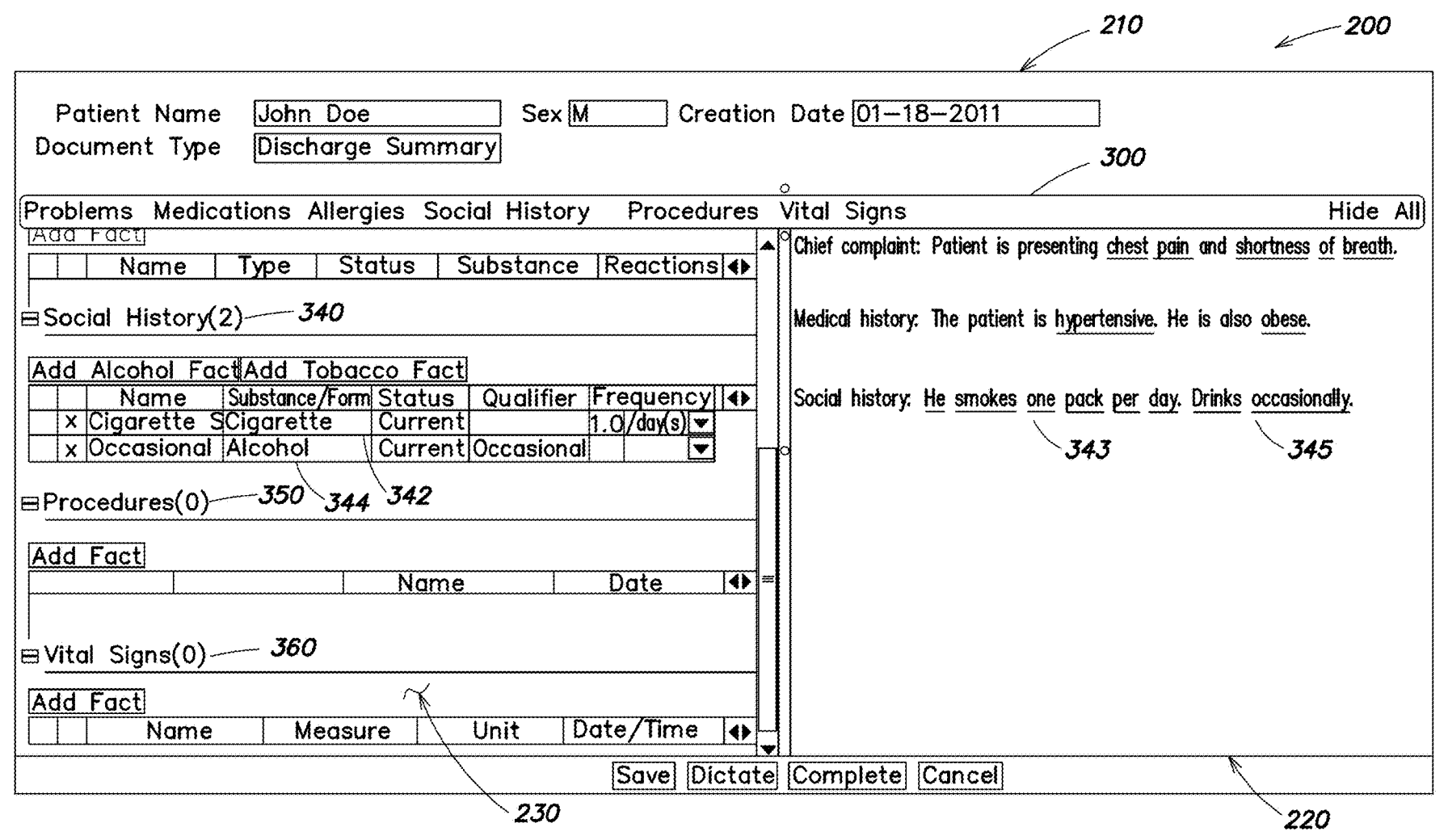

In some embodiments, one or more medical facts extracted from the text narrative by fact extraction component 104 may be displayed to the user via GUI 200 in fact panel 230. Screenshots illustrating an example display of medical facts extracted from an example text narrative are provided in FIGS. 3A and 3B. FIG. 3A is a screenshot with fact panel 230 scrolled to the top of a display listing medical facts extracted from the example text narrative, and FIG. 3B is a screenshot with fact panel 230 scrolled to the bottom of the display listing the extracted medical facts. In some embodiments, as depicted in FIGS. 3A and 3B, medical facts corresponding to a patient encounter may be displayed in fact panel 230, and organized into a number of separate categories of types of facts. An exemplary set of medical fact categories includes categories for problems, medications, allergies, social history, procedures and vital signs. However, it should be appreciated that any suitable fact categories may be used, as aspects of the invention are not limited in this respect. In addition, organization of facts into categories is not required, and displays without such organization are possible. As depicted in FIGS. 3A and 3B, in some embodiments GUI 200 may be configured to provide a navigation panel 300, with a selectable indication of each fact category available in the display of fact panel 230. In some embodiments, when the user selects one of the categories within navigation panel 300 (e.g., by clicking on it with a mouse, touchpad, stylus, or other input device), fact panel 230 may be scrolled to display the corresponding fact category. As depicted in FIGS. 3A and 3B, all available fact categories for the current document type are displayed, even if a particular fact category includes no extracted or otherwise entered medical facts. However, this is not required; in some embodiments, only those fact categories having facts ascertained from the patient encounter may be displayed in fact panel 230.

Fact panel 230 scrolled to the top of the display as depicted in FIG. 3A shows problem fact category 310, medications fact category 320, and allergies fact category 330. Within problem fact category 310, four clinical facts have been extracted from the example text narrative; no clinical facts have been extracted in medications fact category 320 or in allergies fact category 330. Within problem fact category 310, fact 312 indicates that patient 122 is currently presenting with unspecified chest pain; that the chest pain is a currently presenting condition is indicated by the status "active". Fact 314 indicates that patient 122 is currently presenting with shortness of breath. Fact 316 indicates that the patient has a history (status "history") of unspecified essential hypertension. Fact 318 indicates that the patient has a history of unspecified obesity. As illustrated in FIG. 3A, each clinical fact in problem fact category 310 has a name field and a status field. In some embodiments, each field of a clinical fact may be a structured component of that fact represented as a discrete structured data item. In this example, the name field may be structured such that only a standard set of medical terms for problems may be available to populate that field. For example, the status field may be structured such that only statuses in the Systematized Nomenclature of Medicine (SNOMED) standard (e.g., "active" and "history") may be selected within that field, although other standards (or no standard) could be employed. An exemplary list of fact categories and their component fields is given below. However, it should be appreciated that this list is provided by way of example only, as aspects of the invention are not limited to any particular organizational system for facts, fact categories and/or fact components.

Exemplary list of fact categories and component fields:
Category: Problems. Fields: Name, SNOMED status, ICD code.
Category: Medications. Fields: Name, Status, Dose form, Frequency, Measures, RxNorm code, Administration condition, Application duration, Dose route.
Category: Allergies. Fields: Allergen name, Type, Status, SNOMED code, Allergic reaction, Allergen RxNorm.
Category: Social history—Tobacco use. Fields: Name, Substance, Form, Status, Qualifier, Frequency, Duration, Quantity, Unit type, Duration measure, Occurrence, SNOMED code, Norm value, Value.
Category: Social history—Alcohol use. Fields: Name, Substance, Form, Status, Qualifier, Frequency, Duration, Quantity, Quantifier, Unit type, Duration measure, Occurrence, SNOMED code, Norm value, Value.
Category: Procedures. Fields: Name, Date, SNOMED code.
Category: Vital signs. Fields: Name, Measure, Unit, Unit type, Date/Time, SNOMED code, Norm value, Value.

In some embodiments, a linkage may be maintained between one or more medical facts extracted by fact extraction component 104 and the portion(s) of the text narrative from which they were extracted. As discussed above, such a portion of the text narrative may consist of a single word or may include multiple words, which may be in a contiguous sequence or may be separated from each other by one or more intervening words, sentence boundaries, section boundaries, or the like. For example, fact 312 indicating that patient 122 is currently presenting with unspecified chest pain may have been extracted by fact extraction component 104 from the words "chest pain" in the text narrative. The "active" status of extracted fact 312 may have been determined by fact extraction component 104 based on the appearance of the words "chest pain" in the section of the text narrative with the section heading "Chief complaint". In some embodiments, fact extraction component 104 and/or another processing component may be programmed to maintain (e.g., by storing appropriate data) a linkage between an extracted fact (e.g., fact 312) and the corresponding text portion (e.g., "chest pain").

In some embodiments, GUI 200 may be configured to provide visual indicators of the linkage between one or more facts displayed in fact panel 230 and the corresponding portion(s) of the text narrative in text panel 220 from which they were extracted. In the example depicted in FIG. 3A, the visual indicators are graphical indicators consisting of lines placed under the appropriate portions of the text narrative in text panel 220. Indicator 313 indicates the linkage between fact 312 and the words "chest pain" in the "Chief complaint" section of the text narrative; indicator 315 indicates the linkage between fact 314 and the words "shortness of breath" in the "Chief complaint" section of the text narrative; indicator 317 indicates the linkage between fact 316 and the word "hypertensive" in the "Medical history" section of the text narrative; and indicator 319 indicates the linkage between fact 318 and the word "obese" in the "Medical history" section of the text narrative. However, these are merely examples of one way in which visual indicators may be provided, as other types of visual indicators may be provided. For example, different or additional types of graphical indicators may be provided, and/or linked text in text panel 220 may be displayed in a distinctive textual style (e.g., font, size, color, formatting, etc.). Aspects of the invention are not limited to any particular type of linkage indicator.

In some embodiments, when the textual representation of the free-form narration provided by clinician 120 has been re-formatted and fact extraction has been performed with reference to the re-formatted version, the original version may nevertheless be displayed in text panel 220, and linkages may be maintained and/or displayed with respect to the original version. For example, in some embodiments, each extracted clinical fact may be extracted by fact extraction component 104 from a corresponding portion of the re-formatted text, but that portion of the re-formatted text may have a corresponding portion of the original text of which it is a formatted version. A linkage may therefore be maintained between that portion of the original text and the extracted fact, despite the fact actually having been extracted from the re-formatted text. In some embodiments, providing an indicator of the linkage between the extracted fact and the original text may allow clinician 120 and/or other user 150 to appreciate how the extracted fact is related to what was actually said in the free-form narration. However, other embodiments may maintain linkages between extracted facts and the re-formatted text, as an alternative or in addition to the linkages between the extracted facts and the original text, as aspects of the invention are not limited in this respect.

Fact panel 230 scrolled to the bottom of the display as depicted in FIG. 3B shows social history fact category 340, procedures fact category 350, and vital signs fact category 360. Within social history fact category 340, two clinical facts have been extracted; no facts have been extracted in procedures fact category 350 and vital signs fact category 360. Within social history fact category 340, fact 342 indicates that patient 122 currently smokes cigarettes with a frequency of one pack per day. Fact 344 indicates that patient 122 currently occasionally drinks alcohol. Indicator 343 indicates that fact 342 was extracted from the words "He smokes one pack per day" in the "Social history" section of the text narrative; and indicator 345 indicates that fact 344 was extracted from the words "Drinks occasionally" in the "Social history" section of the text narrative. In some embodiments, visual indicators such as indicators 343 and 345 may be of a different textual and/or graphical style or of a different indicator type than visual indicators such as indicators 313, 315, 317 and 319, to indicate that they correspond to a different fact category. For example, in some embodiments indicators 343 and 345 corresponding to social history fact category 340 may be displayed in a different color than indicators 313, 315, 317 and 319 corresponding to problems fact category 310. In some embodiments, linkages for different individual facts may be displayed in different textual and/or graphical styles or indicator types to allow the user to easily appreciate which fact corresponds to which portion of the text narrative. For example, in some embodiments indicator 343 may be displayed in a different color than indicator 345 because they correspond to different facts, even though both correspond to the same fact category.

Figure 4:
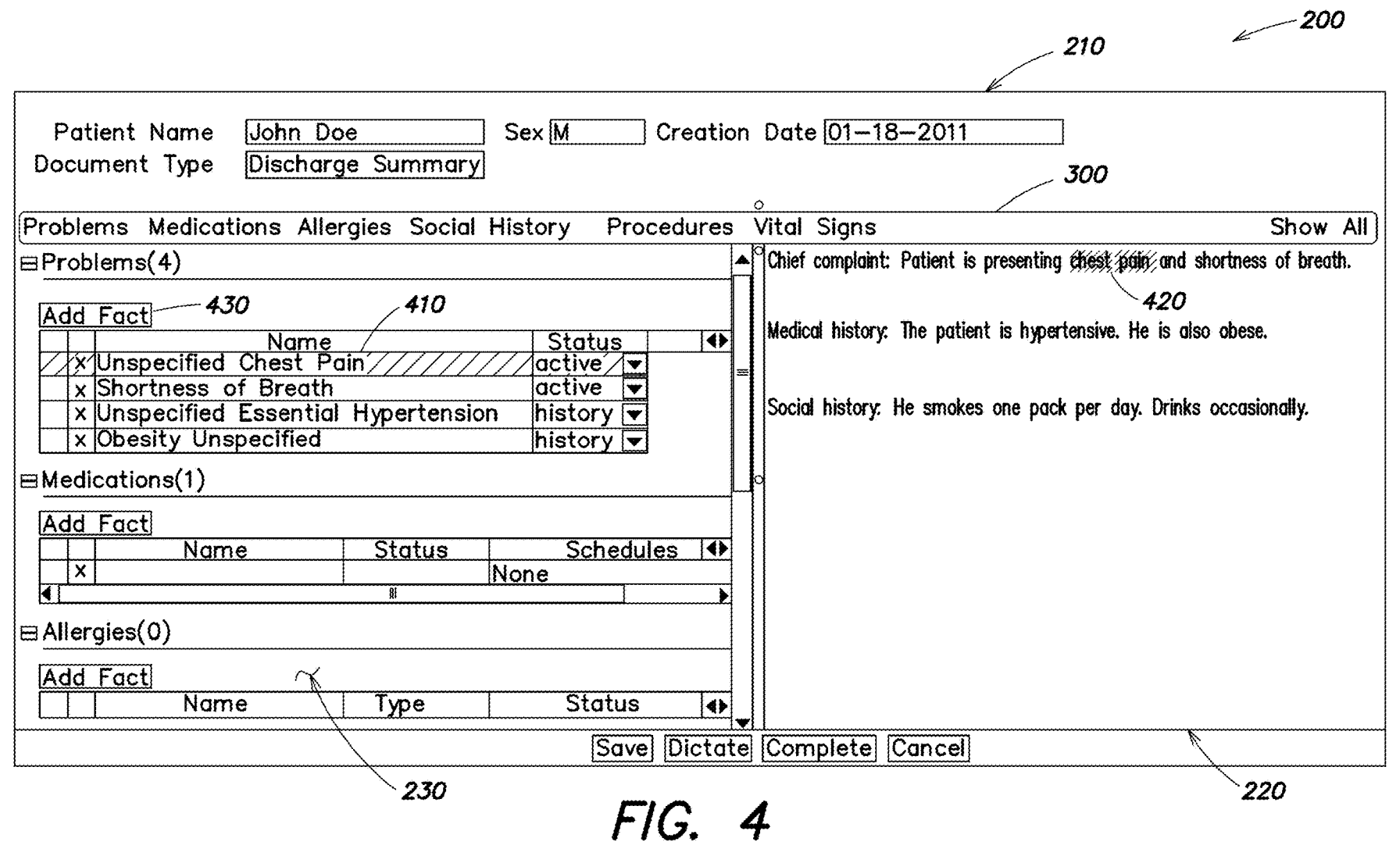

In some embodiments, GUI 200 may be configured to allow the user to select one or more of the medical facts in fact panel 230, and in response to the selection, to provide an indication of the portion(s) of the text narrative from which those fact(s) were extracted. An example is illustrated in FIG. 4. In this example, fact 312 ("unspecified chest pain") has been selected by the user in fact panel 230, and in response visual indicator 420 of the portion of the text narrative from which fact 312 was extracted ("chest pain") is provided. Such a user selection may be made in any suitable way, as aspects of the invention are not limited in this respect. Examples include using an input device (e.g., mouse, keyboard, touchpad, stylus, etc.) to click on or otherwise select fact 312, hovering the mouse or other input mechanism above or nearby to fact 312, speaking a selection of fact 312 through voice, and/or any other suitable selection method. Similarly, in some embodiments GUI 200 may be configured to visually indicate the corresponding fact in fact panel 230 when the user selects a portion of the text narrative in text panel 220. In some embodiments, a visual indicator may include a line or other graphical connector between a fact and its corresponding portion of the text narrative. Any visual indicator may be provided in any suitable form (examples of which are given above) as aspects of the invention are not limited in this respect. In addition, aspects of the invention are not limited to visual indicators, as other forms of indicators may be provided. For example, in response to a user selection of fact 312, an audio indicator of the text portion "chest pain" may be provided in some embodiments. In some embodiments, the audio indicator may be provided by playing the portion of the audio recording of the clinician's spoken dictation comprising the words "chest pain". In other embodiments, the audio indicator may be provided by playing an audio version of the words "chest pain" generated using automatic speech synthesis. Any suitable form of indicator or technique for providing indicators may be used, as aspects of the invention are not limited in this respect.

In some embodiments, GUI 200 may be configured to provide any of various ways for the user to make one or more changes to the set of medical facts extracted from the text narrative by fact extraction component 104 and displayed in fact panel 230, and these changes may be collected by fact review component 106 and applied to the documentation of the patient encounter. For example, the user may be allowed to delete a fact from the set in fact panel 230, e.g., by selecting the "X" option appearing next to the fact. In some embodiments, the user may be allowed to edit a fact within fact panel 230. In one example, the user may edit the name field of fact 312 by selecting the fact and typing, speaking or otherwise providing a different name for that fact. As depicted in FIG. 3A and FIG. 4, in some embodiments the user may edit the status field of fact 312 by selecting a different status from the available drop-down menu, although other techniques for allowing editing of the status field are possible. In some embodiments, the user may alternatively or additionally be allowed to edit a fact by interacting with the text narrative in text panel 220. For example, the user may add, delete, or change one or more words in the text narrative, and then the text narrative may be re-processed by fact extraction component 104 to extract an updated set of medical facts. In some embodiments, the user may be allowed to select only a part of the text narrative in text panel 220 (e.g., by highlighting it), and have fact extraction component 104 re-extract facts only from that part, without disturbing facts already extracted from other parts of the text narrative.

Figure 5:
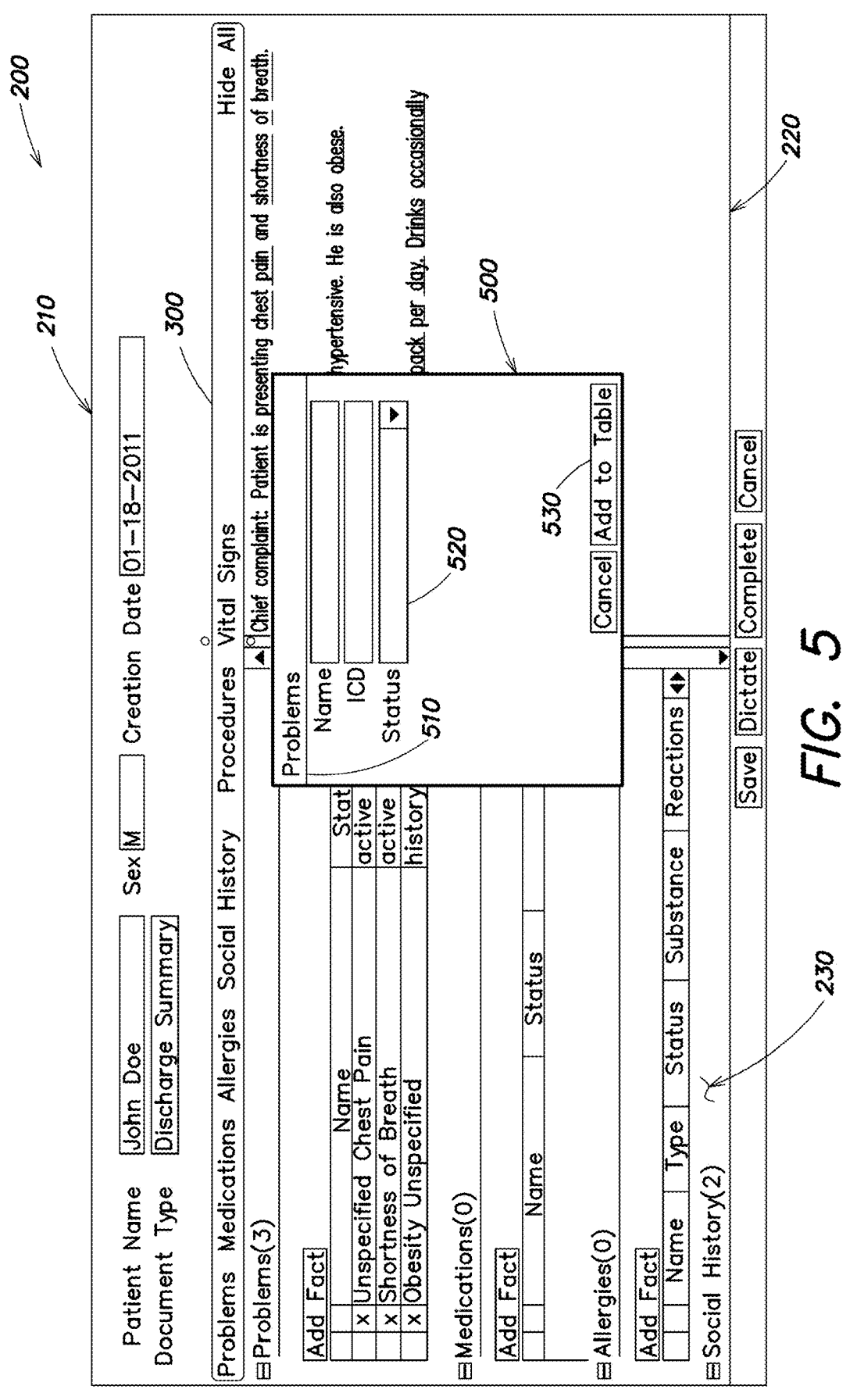

In some embodiments, GUI 200 may be configured to provide any of various ways for one or more facts to be added as discrete structured data items. As depicted in FIG. 4, GUI 200 in some embodiments may be configured to provide an add fact button for each fact category appearing in fact panel 230; one such add fact button is add fact button 430. When the user selects add fact button 430, in some embodiments GUI 200 may provide the user with a way to enter information sufficient to populate one or more fields of a new fact in that fact category, for example by displaying pop-up window 500 as depicted in FIG. 5. It should be appreciated that this is merely one example, as aspects of the invention are not limited to the use of pop-up windows or any other particular method for adding a fact. In this example, pop-up window 500 includes a title bar 510 that indicates the fact category ("Problems") to which the new fact will be added. Pop-up window 500 also provides a number of fields 520 in which the user may enter information to define the new fact to be added. Fields 520 may be implemented in any suitable form, including as text entry boxes, drop-down menus, radio buttons and/or checkboxes, as aspects of the invention are not limited to any particular way of receiving input defining a fact. Finally, pop-up window 500 includes add button 530, which the user may select to add the newly defined fact to the set of facts corresponding to the patient encounter, thus entering the fact as a discrete structured data item.

In some embodiments, GUI 200 may alternatively or additionally be configured to allow the user to add a new fact by selecting a (not necessarily contiguous) portion of the text narrative in text panel 220, and indicating that a new fact should be added based on that portion of the text narrative. This may be done in any suitable way. In one example, the user may highlight the desired portion of the text narrative in text panel 220, and right-click on it with a mouse (or perform another suitable input operation), which may cause the designated text to be processed and any relevant facts to be extracted. In other embodiments, the right-click or other input operation may cause a menu to appear. In some embodiments the menu may include options to add the new fact under any of the available fact categories, and the user may select one of the options to indicate which fact category will correspond to the new fact. In some embodiments, an input screen such as pop-up window 500 may then be provided, and the name field may be populated with the words selected by the user from the text narrative. The user may then have the option to further define the fact through one or more of the other available fields, and to add the fact to the set of medical facts for the patient encounter as described above.

In some embodiments, the set of medical facts corresponding to the current patient encounter (each of which may have been extracted from the text narrative or provided by the user as a discrete structured data item) may be added to an existing electronic medical record (such as an EHR) for patient 122, or may be used in generating a new electronic medical record for patient 122. In some embodiments, clinician 120 and/or coding specialist (or other user) 150 may finally approve the set of medical facts before they are included in any patient record; however, aspects of the present invention are not limited in this respect. In some embodiments, when there is a linkage between a fact in the set and a portion of the text narrative, the linkage may be maintained when the fact is included in the electronic medical record. In some embodiments, this linkage may be made viewable by simultaneously displaying the fact within the electronic medical record and the text narrative (or at least the portion of the text narrative from which the fact was extracted), and providing an indication of the linkage in any of the ways described above. Similarly, extracted facts may be included in other types of patient records, and linkages between the facts in the patient records and the portions of text narratives from which they were extracted may be maintained and indicated in any suitable way.

Figure 6:
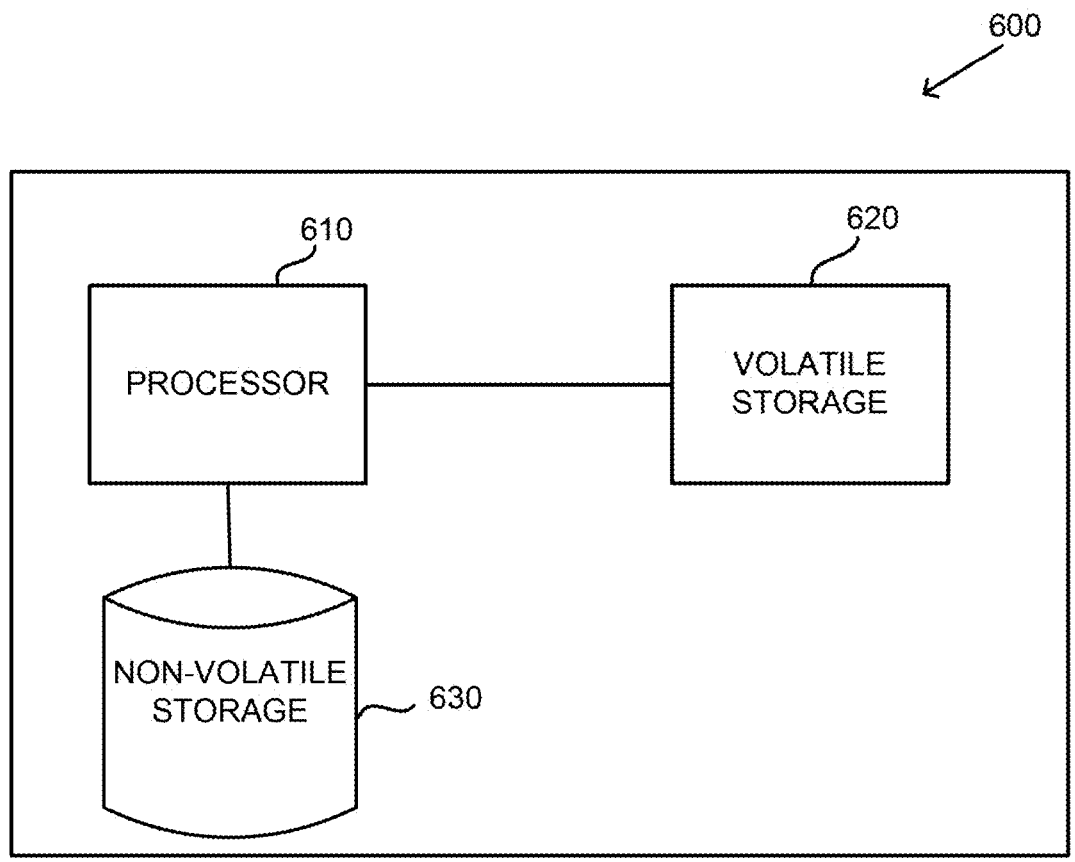
FIG. 6 is a block diagram of an exemplary computer system on which aspects of some embodiments may be implemented.

A CLU system in accordance with the techniques described herein may take any suitable form, as aspects of the present invention are not limited in this respect. An illustrative implementation of a computer system 600 that may be used in connection with some embodiments of the present invention is shown in FIG. 6. One or more computer systems such as computer system 600 may be used to implement any of the functionality described above. The computer system 600 may include one or more processors 610 and one or more tangible, non-transitory computer-readable storage media (e.g., volatile storage 620 and one or more non-volatile storage media 630, which may be formed of any suitable non-volatile data storage media). The processor 610 may control writing data to and reading data from the volatile storage 620 and the non-volatile storage device 630 in any suitable manner, as the aspects of the present invention are not limited in this respect. To perform any of the functionality described herein, the processor 610 may execute one or more instructions stored in one or more computer-readable storage media (e.g., volatile storage 620), which may serve as tangible, non-transitory computer-readable storage media storing instructions for execution by the processor 610.

Computer-Assisted Coding (CAC) System

As discussed above, medical coding has conventionally been a manual process whereby a human professional (the "coder") reads all of the documentation for a patient encounter and enters the appropriate standardized codes (e.g., ICD codes, HCPCS codes, etc.) corresponding to the patient's diagnoses, procedures, etc. The coder is often required to understand and interpret the language of the clinical documents in order to identify the relevant diagnoses, etc., and assign them their corresponding codes, as the language used in clinical documentation often varies widely from the standardized descriptions of the applicable codes. For example, the coder might review a hospital report saying, "The patient coded at 5:23 pm." The coder must then apply the knowledge that "The patient coded" is hospital slang for a diagnosis of "cardiac arrest," which corresponds to ICD-9-CM code 427.5. This diagnosis could not have been identified from a simple word search for the term "cardiac arrest," since that standard term was not actually used in the documentation; more complex interpretation is required in this example.

As also discussed above, conventional medical coding systems may provide a platform on which the human coder can read the relevant documents for a patient encounter, and an interface via which the human coder can manually input the appropriate codes to assign to the patient encounter. By contrast, some embodiments described herein may make use of a type of medical coding system referred to herein as a "computer-assisted coding" (CAC) system, which may automatically analyze medical documentation for a patient encounter to interpret the document text and derive standardized codes hypothesized to be applicable to the patient encounter. The automatically derived codes may then be suggested to the human coder, clinician, or other user of the CAC system. In some embodiments, the CAC system may make use of an NLU engine to analyze the documentation and derive suggested codes, such as through use of one or more components of a CLU system such as exemplary system 100 described above. In some embodiments, the NLU engine may be configured to derive standardized codes as a type of medical fact extracted from one or more documents for the patient encounter, and/or the CLU system may be configured to access coding rules corresponding to the standardized code set(s) and apply the coding rules to extracted medical facts to derive the corresponding codes.

In some embodiments, the CAC system may be configured to provide a user interface via which the automatically suggested codes may be reviewed by a user such as a medical coder. The user interface may take on any of numerous forms, and aspects of the invention are not limited to any particular implementation Like the user interfaces for the CLU system 100 described above, the user interface for the CAC system may provide tools that allow a coder to interact with the CAC system in any suitable form, including visual forms, audio forms, combined forms, or any other form providing the functionality described herein. When the tools are provided in visual form, their functionality may be accessed in some embodiments through a graphical user interface (GUI), which may be implemented in any suitable way. An example of a suitable GUI 700 for a CAC system is illustrated in FIG. 7A.

The exemplary GUI 700 provides the user with the ability to simultaneously view the list of codes for a patient encounter along with the documentation from which the codes are derived. Some embodiments may also allow the user to view structured encounter- or patient-level data such as the patient's age, gender, etc. (not shown in FIG. 7A), some or all of which information may be useful in arriving at the appropriate codes for the patient encounter. In panel 710 is displayed a list of available documents for the patient encounter currently being coded. In the example illustrated in FIG. 7A, these include two History & Physical reports, a Discharge Summary, an Emergency Room Record, a Consultation report, a Progress Note, and an Operative Report. Indicator 712 shows that the current document being viewed is the Discharge Summary dated Jun. 18, 2014, and this document appears in panel 720 where the user can view the text of the document. Shown in panel 730 is the current list of codes for the patient encounter. An indicator 732 shows, for each code in the list, whether the code was automatically suggested or added manually by the user. In this particular example, the empty circles indicate that all of the codes in the current list were automatically suggested by the CAC system.

Exemplary GUI 700 also provides the user with the ability to view and/or query which portion(s) of the available documentation gave rise to the suggestion of which code(s) in the list of codes for the patient encounter. In some embodiments, any suitable indicator(s) may be provided of the link between a particular code and the portion(s) of the documentation text from which the code was derived. Each automatically suggested code may be linked to one or more portions of text from which the code was derived, and each linked portion of text may be linked to one or more codes that are derivable from that portion of text. For instance, viewing together FIGS. 7A and 7D, which show the Discharge Summary viewed at different scroll locations in panel 720, it can be seen that there are two different mentions of "respiratory failure" in the document from which code 518.81 may have been derived (an example of a link between a code and multiple portions of text), and that there are two different codes 303.90 and 571.5 that may have been derived at least in part from the mention of "Alcoholism" in the text (an example of a link between a portion of text and multiple codes).

In the example of FIG. 7A, an indicator 722 is provided (underlining in this particular example) to visually distinguish portions of the document text linked to codes in the current list. Exemplary GUI 700 also allows the user to query a particular linked portion of text to see which code(s) are linked to that portion of text. FIG. 7B illustrates an exemplary indicator 724 of the corresponding link that may be displayed in response to the user querying the linked portion of text in any suitable way, such as by selecting or hovering over it with the mouse pointer. Exemplary GUI 700 further allows the user to query a particular code to see which portion(s) of text are linked to that code. FIG. 7C illustrates an exemplary way of querying code 287.5 by right-clicking on the listed code in panel 730 and selecting "Show Highlights" in the context menu that then appears. In response, the document in which the linked text appears is displayed in panel 720 (in this case it is the same Discharge Summary, scrolled to a particular section), and the linked text is visually distinguished by indicator 726 (highlighting in this particular example), as illustrated in FIG. 7D.

If the user disagrees with the linked text and does not believe that the suggested portion(s) of text actually should correspond with the linked code, the user can select "Unlink Text" in the context menu of FIG. 7C to cause the link between that code and the corresponding text to be discarded. The user can also manually create a new link between a code and one or more portions of text, e.g., by selecting "Link Text" in the context menu of FIG. 7C and highlighting or otherwise designating the portion(s) of text in the documentation which should be linked to the selected code.

Figure 7E:
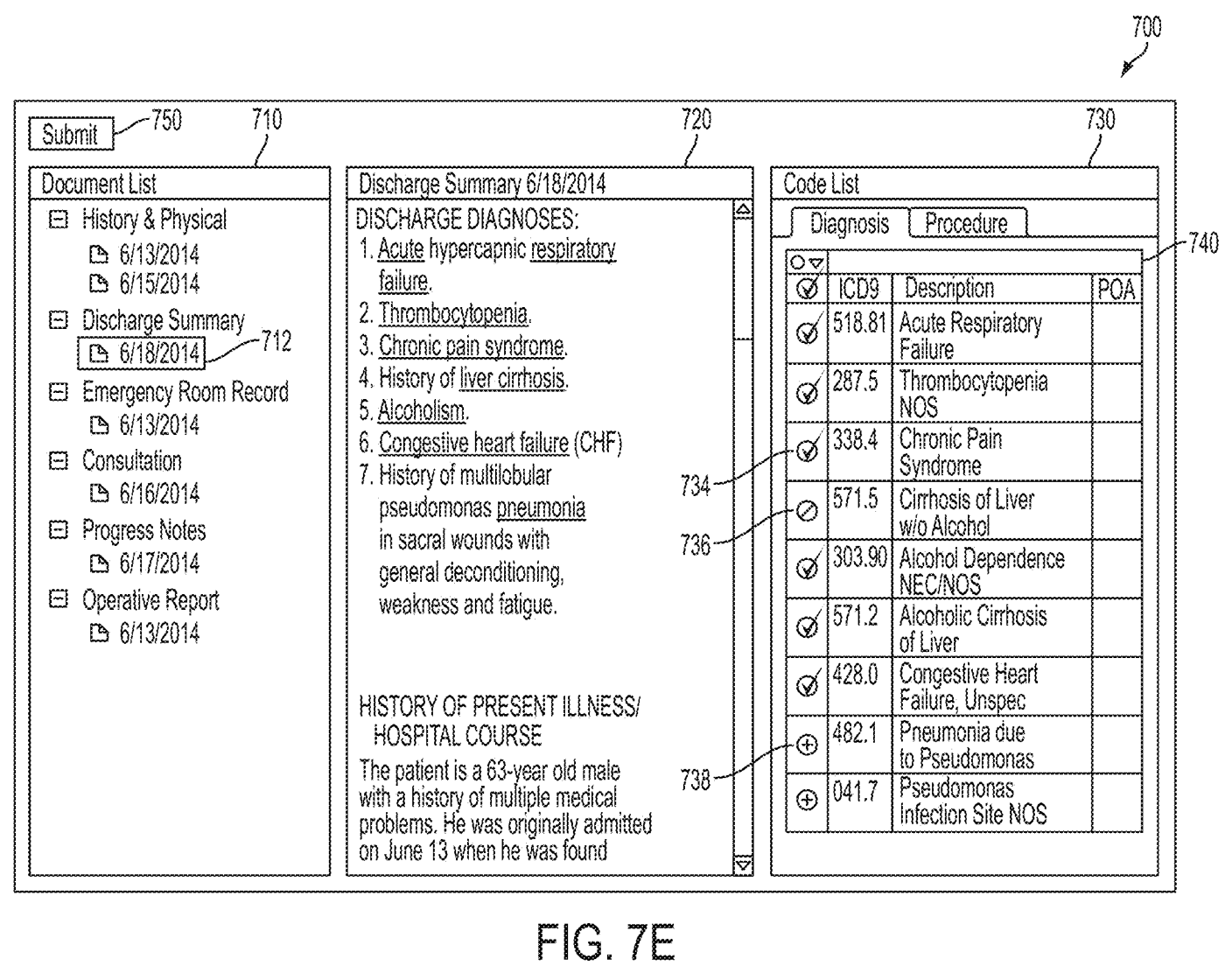

Exemplary GUI 700 further allows the user to accept or reject each of the automatically suggested codes, e.g., using the context menu of FIG. 7C for each suggested code. FIG. 7E illustrates exemplary indicators 734 and 736 which replace indicator 732 for each code that has been accepted or rejected, respectively. In this example, the user has accepted most of the suggested codes, but has rejected code 571.5 because the user believes the mention of "Alcoholism" in the documentation makes the diagnosis of "Cirrhosis of Liver w/o Alcohol" incorrect. Exemplary GUI 700 further allows the user to provide a reason for the rejection of a code, such as by using the exemplary context menu illustrated in FIG. 7F. In some embodiments, the reasons provided by users for rejecting particular automatically suggested codes may be used for review and/or training purposes (e.g., for training the NLU engine, e.g., of the CLU system to derive more accurate codes from documentation text).

GUI 700 may also allow the user to replace a code with a different code, instead of rejecting the code outright, e.g., using the context menu of FIG. 7C. In the example illustrated in FIG. 7E, the user has replaced code 482.9 with code 482.1, and indicator 738 shows that the new code was user-added. 482.9 (Pneumonia due to *Pseudomonas*) is a more specific diagnosis applicable to the patient encounter than the suggested 482.1 (Bacterial Pneumonia, Unspecified), so the user may provide "More specific code needed" as the reason for the replacement. In some embodiments, when a user replaces an automatically suggested code with a different code, any documentation text that was linked to the originally suggested code may then be linked to the replacement code. Such replacement codes, optionally with linked text and/or replacement reasons, may also be used as feedback, e.g., for training of the CLU system.

The user can also add a code to the list for a patient encounter by manually inputting the code in input field 740. For example, FIG. 7E shows a new code 041.7 that has been added by the user. The user may link the added code to supporting portion(s) of the text, such as the mention of "*pseudomonas*" in the Discharge Summary, e.g., by using the "Link Text" procedure described above. When the user has completed the review of the codes and supporting documentation, exemplary GUI 700 allows the user to submit the codes for finalization by selecting button 750.

FIG. 8 illustrates an exemplary code finalization screen 800 that may be displayed following the user's selection of submit button 750. In exemplary screen 800, all of the accepted and user-added codes are displayed for final review. Alternatively, in some embodiments the user may be required to affirmatively accept even user-added codes before they will appear in code finalization screen 800. The codes are displayed in screen 800 in an ordered sequence, which the user may change by re-ordering the codes. In some embodiments, the order of the finalized sequence of codes may be used in later processes such as billing, to determine the principal diagnosis, etc. Exemplary screen 800 also includes fields for "present on admission" (POA) indicators, which provide information on whether each diagnosis was present when the patient was admitted to the hospital, or was acquired during the hospital stay. This information may be required documentation in some circumstances, and in some embodiments may be used for review and/or training purposes. In some embodiments, POA indicators may be automatically suggested, e.g., using the CLU system; while in other embodiments, POA indicators may only be input manually.

When the user is satisfied with the finalized sequence of codes, exemplary screen 800 provides a button 810 for the codes to be saved, at which the coding process for the patient encounter becomes complete. In some embodiments, the CAC system may compare the finalized sequence of codes with stored coding rules, and may present the user with any applicable error or warning notifications prior to saving. As discussed above, once saved, the finalized sequence of codes may be sent to other processes such as billing and quality review, and in some embodiments may be used for performance review and/or training of the CLU and/or CAC systems.

Figure 9:
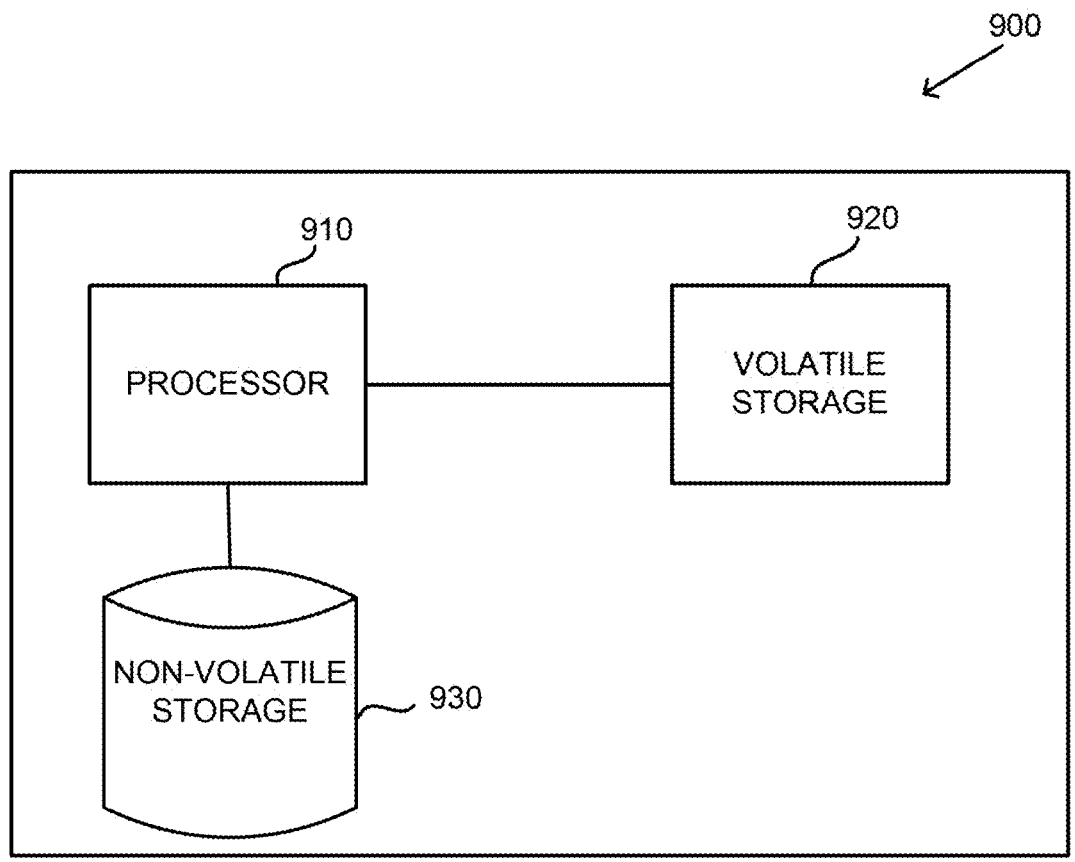
FIG. 9 is a block diagram of an exemplary computer system on which aspects of some embodiments may be implemented.

Like the embodiments of the CLU system 100 described above, the CAC system in accordance with the techniques described herein may take any suitable form, as embodiments are not limited in this respect. An illustrative implementation of a computer system 900 that may be used in connection with some implementations of a CAC system is shown in FIG. 9. One or more computer systems such as computer system 900 may be used to implement any of the functionality of the CAC system described above. As shown, the computer system 900 may include one or more processors 910 and one or more tangible, non-transitory computer-readable storage media (e.g., volatile storage 920 and one or more non-volatile storage media 930, which may be formed of any suitable non-volatile data storage media). The processor 910 may control writing data to and reading data from the volatile storage 920 and the non-volatile storage media 930 in any suitable manner, as the aspects of the present invention are not limited in this respect. To perform any of the functionality described herein, the processor 910 may execute one or more instructions stored in one or more computer-readable storage media (e.g., volatile storage 920), which may serve as tangible, non-transitory computer-readable storage media storing instructions for execution by the processor 910.

NLU Training Techniques

According to an aspect of the present application, training data for training a NLU engine is generated by providing a corpus of free-form text to both the NLU engine and one or more human annotators, both of which generate annotations that are then merged. The term "annotation" as used herein refers to an item derived from and linked to a portion of text, such as a fact (e.g., a medical fact, one particular example of which may be a medical code such as a medical billing code), a semantic label, or other such item having a link to one or more corresponding portions of text from which it was or could be derived. For example, in some embodiments, techniques described herein may be used for training a NLU engine used in a CLU system such as system 100 described above. In some embodiments, the NLU engine may be used to automatically derive medical billing codes for a CAC system such as described above, and in some embodiments, such a CAC system may be used by the human annotator(s) for entering codes as annotations. As described above, a CAC system may also be used in some embodiments by a human coder to enter some codes not as annotations (i.e., without linking the code to any text in a medical document); however, the CAC system may additionally allow the coder in some embodiments to create an annotation from a medical code by linking it to supporting document text, where appropriate.

Figure 10:
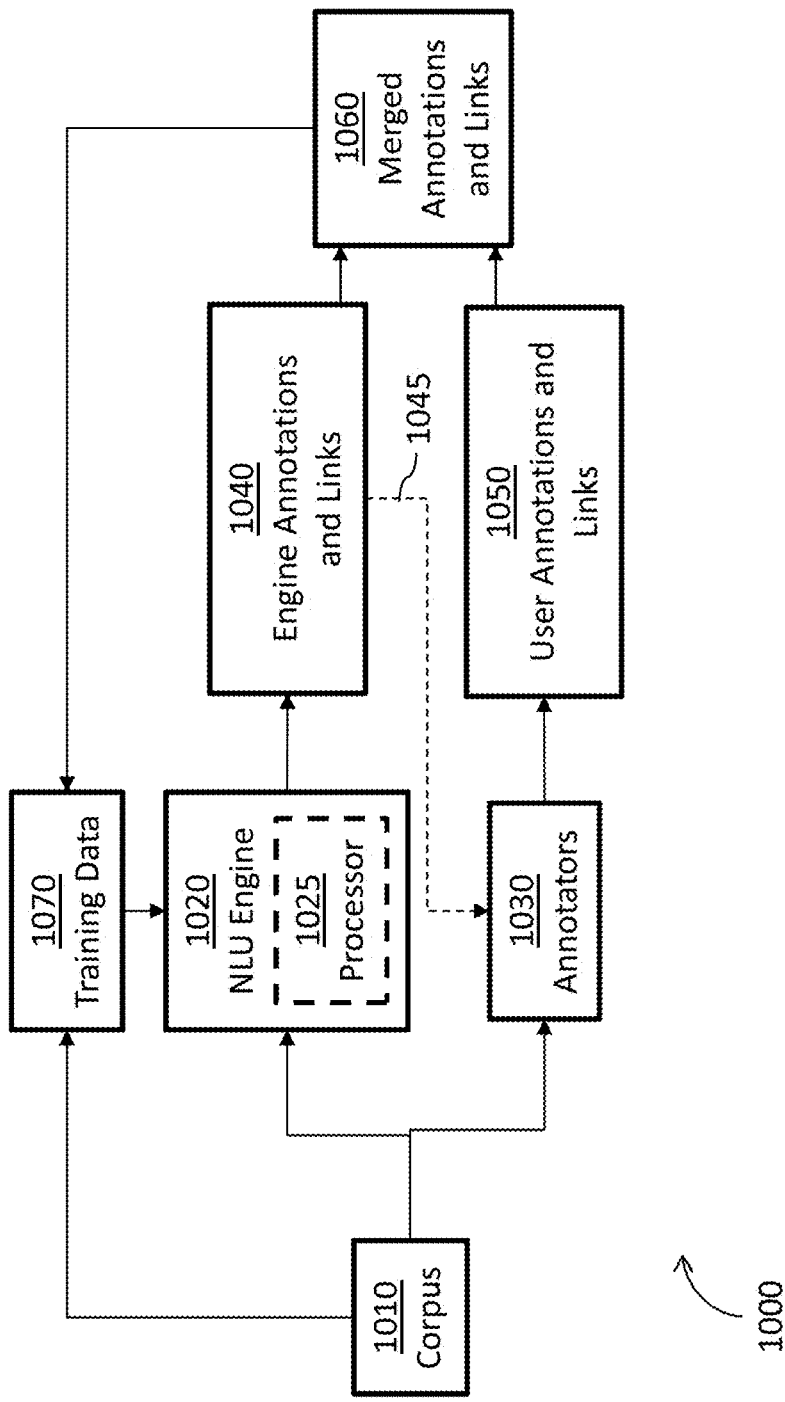
FIG. 10 is a block diagram of a system for training a natural language understanding (NLU) engine in accordance with some embodiments.

FIG. 10 is a block diagram of a system 1000 which may be used in some embodiments to generate training data for a NLU engine. In the example of FIG. 10, corpus 1010 is provided both to a NLU engine 1020 and to one or more human annotators 1030. NLU engine 1020 may be implemented on a processor 1025, which may be a processor specific to NLU engine 1020 or may be a processor on which NLU engine 1020 and any other suitable components are run, including, in some embodiments, other systems described herein. Corpus 1010 may include free-form text (in one or more documents) documenting one or more clinical patient encounters, although other text subjects are also possible. The text of the corpus 1010 may be in any suitable format.

In some embodiments, the documents of corpus 1010 may be selected based on the complexity and the medical field of the documents, and the documents of corpus 1010 may pertain to a common medical field and/or have the same complexity.

The NLU engine 1020 may analyze the corpus 1010 and generate annotations, for example, for appropriate portions of the corpus 1010, as well as links between the annotations and their corresponding portions of the corpus 1010, which together may constitute the engine annotations and links 1040. The annotations may be related to medical information such as medical billing codes and/or any other suitable information. Further examples of the annotations will be illustrated below in connection with FIG. 12.

The annotators 1030 may also study the corpus 1010 and input annotations for appropriate portions of the corpus 1010, as well as links between the annotations and their corresponding portions of the corpus 1010, which together may constitute the user annotations and links 1050. In some embodiments, multiple annotators may annotate the same document, so that the user annotations and links 1050 may include annotations by one or more annotators of the same documents. The annotators 1030 may provide evidence supporting the user annotations and links 1050. Providing evidence may include identifying portions of the text that justify the user annotations and links 1050, and/or providing reasons for the user annotations and links 1050. Reasons may include correcting a mistaken annotation or link, increasing the specificity of an annotation, or any other suitable reason.

The annotators 1030 may provide evidence by highlighting any desired portion or portions of the text, right-clicking on the portion or portions with a mouse, and/or any other suitable input operation. The annotators 1030 may provide a reason by entering the reason using a keyboard, selecting the reason by clicking an item in a drop-down menu using a mouse, or using any other suitable input operation.

In some embodiments, the NLU engine 1020 may optionally provide the engine annotations and links 1040 to the annotators 1030 (via a computer user interface similar to or the same as user interface 110 or any other suitable user interface) as illustrated by dashed arrow 1045, which the annotators 1030 may use in generating the user annotations and links 1050. The annotators 1030 may add to or otherwise alter the engine annotations and links 1040. The annotators 1030 may provide evidence supporting their additions or other alterations to the engine annotations and links 1040. Providing evidence may include identifying portions of the text that justify their additions or other alterations, and/or providing reasons for the additions or other alterations. Reasons may include correcting a mistaken annotation or link, increasing the specificity of an annotation, or any other suitable reason. For example, if the engine annotations and links 1040 include a generic medical billing code for a fracture while the corresponding text also includes a dislocation for the same clinical patient encounter, the annotators 1030 may replace the generic medical billing code for a fracture with a specific medical billing code for a fracture plus dislocation and may provide the reason, namely, that a more specific medical billing code was available.

The respective annotations and links 1040 and 1050 from the NLU engine 1020 and the annotators 1030 (e.g., received via a computer user interface similar to or the same as user interface 110 or any other suitable user interface) may be merged into merged annotations and links 1060. This merging may be accomplished in some embodiments by comparing the annotations and links from each source and removing redundant annotations, by flagging user annotations and/or links that conflict with engine annotations and/or links, by comparing the order of annotations from each source and identifying differences, etc. Where a difference exists between the annotations and links from each source, the user annotations and links 1050 may be assumed to be the correct annotations and links, while the conflicting engine annotations and links 1040 may be retained for training the NLU engine to avoid similar errors in future analyses. Also, multiple annotators may annotate the same document and the merged annotations may therefore include annotations from multiple annotators.

It should also be appreciated that while in some embodiments the annotations from different sources may be merged, in other embodiments, the annotations from multiple sources may be used separate for training purposes. For example, the annotations from multiple sources may be separately provided to an NLU engine for training.

Training data 1070 including the merged annotations and links 1060 and the corpus 1010 may be provided to the NLU engine 1020 for training of the NLU engine 1020. The training may advantageously occur in real time, but it may also occur at any other suitable time. In some embodiments, the NLU engine 1020 may use for training the corpus 1010 it received initially, and the corpus 1010 need not be provided to the NLU engine 1020 a second time in the form of the training data 1070. However, for purposes of illustrating that the corpus 1010 may be used for training, the corpus 1010 is illustrated in FIG. 10 as being provided to the NLU engine distinctly in the form of the training data 1070 and in fact in some embodiments the corpus 1010 may be provided to the NLU engine as part of the training data 1070.

The training data may be used to increase the accuracy of the NLU engine 1020 by providing the merged annotations and links 1060, which include both the engine annotations and links 1040 and the user annotations and links 1050 (i.e., annotations and links from two different sources), to the NLU engine. The resulting training data 1070 may provide greater information in training the NLU engine 1020 than could be obtained otherwise, leading to this increase in accuracy.

In some embodiments, the annotators 1030 may be employees or contractors of a developer (e.g., a developer of a software application for performing annotations of transcribed text) or may have any other suitable affiliation with the developer. The system 1000 may be implemented with these annotators 1030 at a batch level in some embodiments, and the process may be performed by the developer, for instance as part of a dedicated training process for the NLU engine 1020. For example, a company developing the NLU engine may, as part of a dedicated process of training the NLU engine, hire coders (e.g., annotators 1030) to annotate the same documents annotated by the NLU engine, with the annotations from both sources (the NLU engine and the human annotators) being used to train the engine. In this sense, the method may, in some embodiments, be applied in a controlled training setting.

Figure 11:
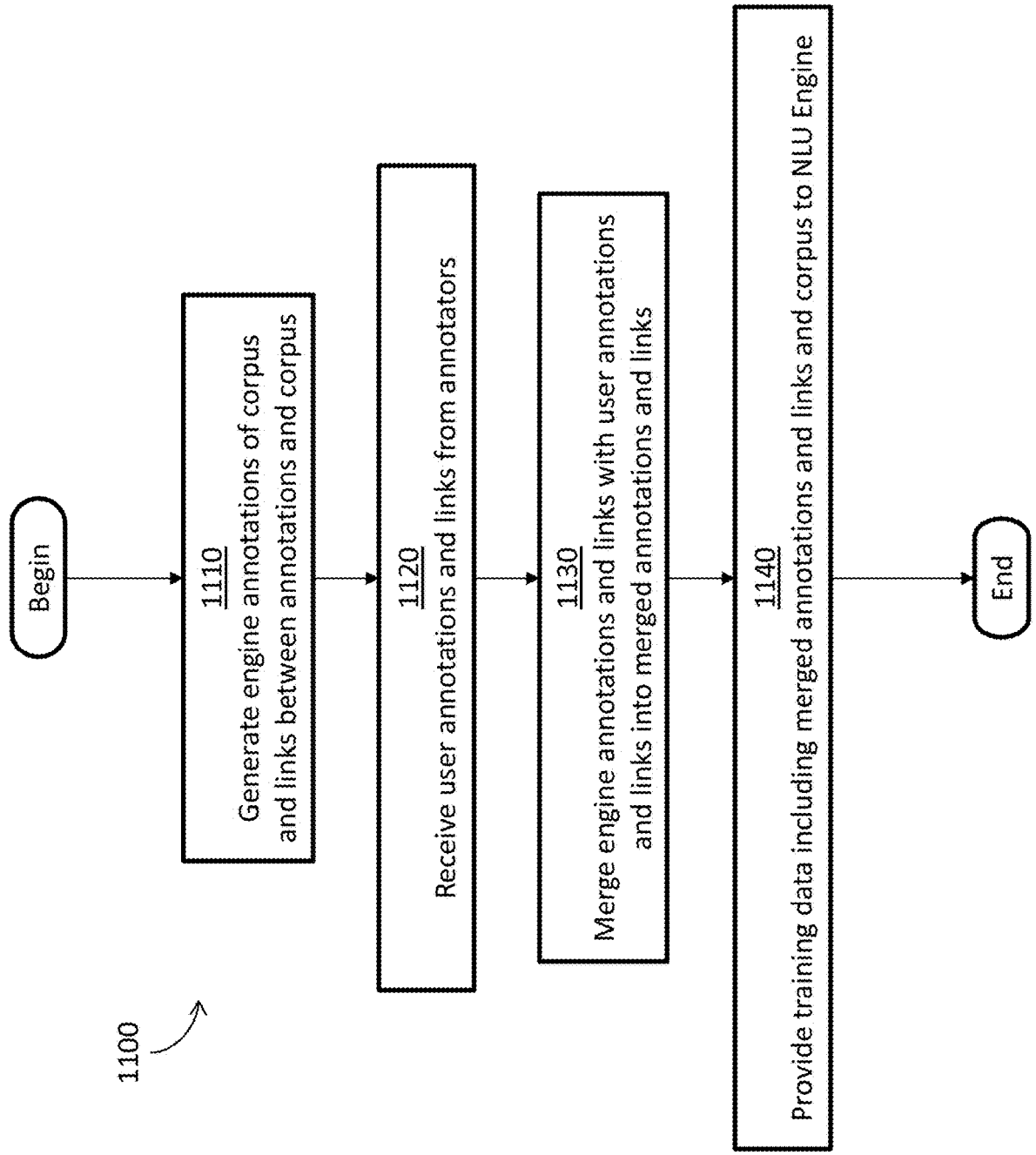
FIG. 11 is a flowchart of a method for training a NLU engine in accordance with some embodiments.

Referring now to FIG. 11, a flowchart of a method 1100 for training a NLU engine, in accordance with some embodiments, is depicted. At stage 1110, engine annotations of a corpus of free-form text and links between the annotations and corresponding portions of the text may be generated by applying the NLU engine to the corpus using a processor. At stage 1120, user annotations of the same text and links between the annotations and corresponding portions of the text may be received from one or more human annotators of the types described in connection with FIG. 10. At stage 1130, the engine annotations and links and the user annotations and links may be merged into merged annotations and links in any of the manners described in connection with FIG. 10 or in any other suitable manner. At stage 1140, training data including the merged annotations and links and the text may be provided to the NLU engine. Training of the NLU engine may then proceed in any suitable manner. In some embodiments, the NLU engine may use for training the corpus described at stage 1110, and the corpus need not be separately or additionally provided to the NLU engine in the form of the training data. However, for purposes of illustrating that the corpus may be used for training, the corpus is shown in FIG. 11 as being provided to the NLU engine distinctly in the form of the training data and in fact in some embodiments the corpus may be provided to the NLU engine as part of the training data.

Figure 12:
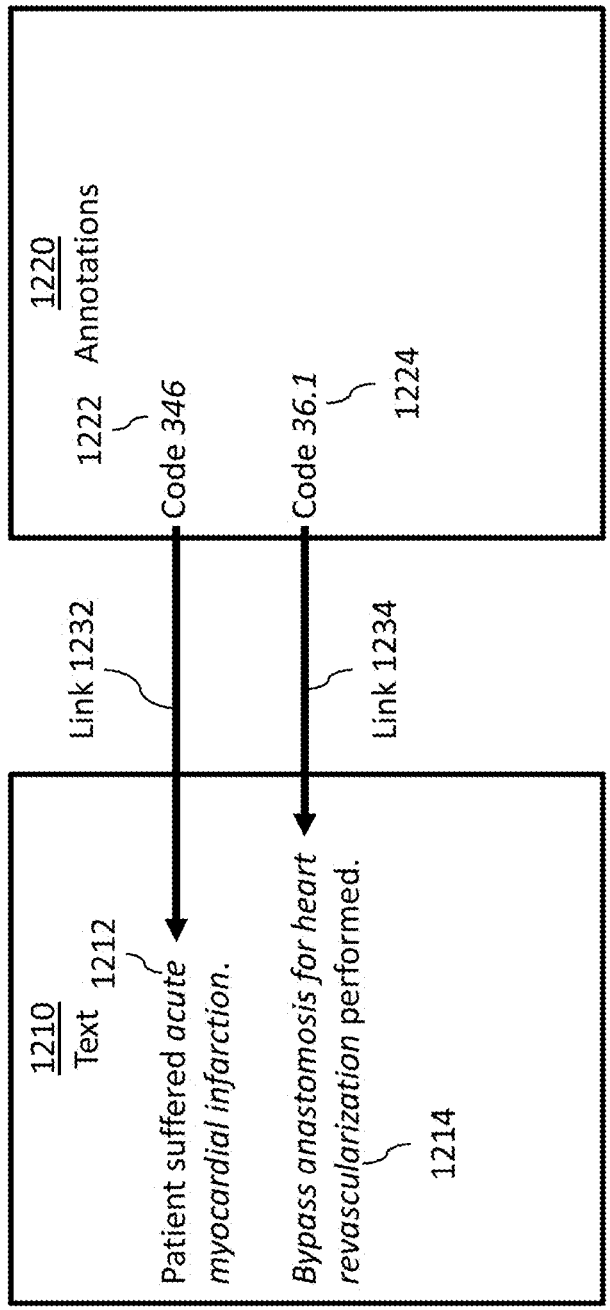
FIG. 12 illustrates an example of text and corresponding annotations and links in accordance with some embodiments.

FIG. 12 illustrates an example of text and corresponding annotations and links in accordance with some embodiments, and as may be used in connection with the systems and methods of FIGS. 10 and 11. Text 1210, which may be part of corpus 1010, may represent free-form text documenting a clinical patient encounter, and in some embodiments may represent transcribed text. For instance, in the particular example of FIG. 12, the text 1210 includes a portion documenting a diagnosis 1212 and a portion documenting a procedure 1214, shown in italics. Annotations 1220, which may be generated by a NLU engine (e.g., NLU engine 1020) or a human annotator (e.g., annotator 1030) may include a medical code (e.g., a medical billing code) for each appropriate portion of the text 1210. For example, the annotations 1210 may include a diagnostic code 1222 corresponding to the diagnosis 1212 and a procedure code 1224 corresponding to the procedure 1214, with the codes also shown in italics. The diagnostic code 1222 may be associated with the diagnosis 1212 using a link 1232, and the procedure code 1224 may be associated with the procedure 1214 using a link 1234. The links 1232 and 1234 may be entries in a field of a database table associating annotations 1220 with portions of the text 1210, or they may be pointers or any other suitable data association. It should be appreciated that the examples of annotations illustrated in FIG. 12 are non-limiting, and that various other types and forms of annotations are possible, including those not related to medical annotations.

Figure 13:
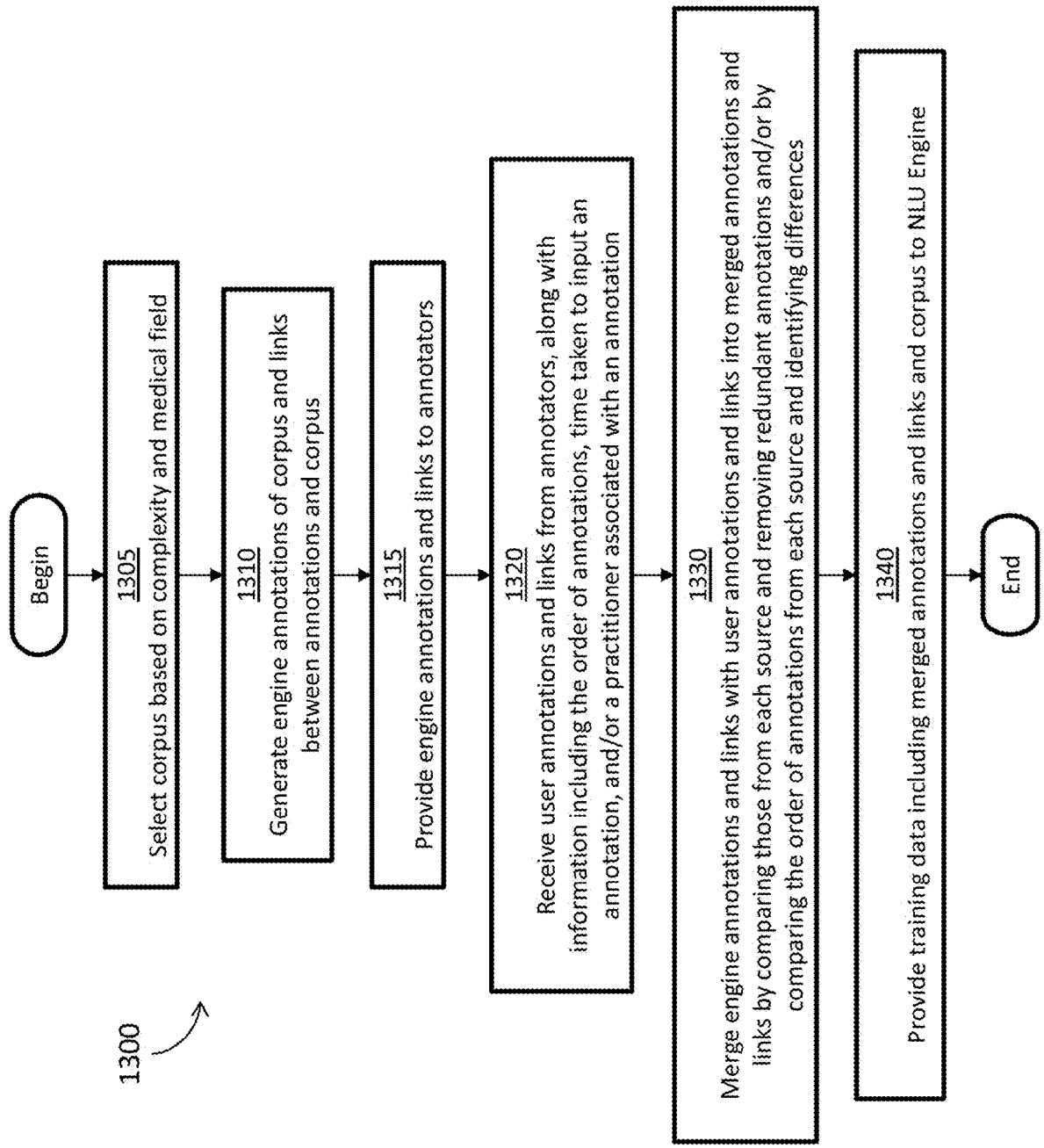
FIG. 13 is a flowchart of a method for training a NLU engine in accordance with some embodiments.

Referring now to FIG. 13, a flowchart of a method 1300 for training a NLU engine, in accordance with some embodiments, is depicted. At stage 1305, a corpus of text may be selected based on its complexity and its medical field. At stage 1310, engine annotations of the corpus of free-form text and links between the annotations and corresponding portions of the text may be generated by applying the NLU engine using a processor. In some embodiments, at stage 1315, the engine annotations and links may be provided to one or more human annotators (see, e.g., dashed arrow 1045 in FIG. 10). At stage 1320, user annotations of the text and links between the annotations and corresponding portions of the text may be received from the annotators (e.g., annotators 1030 in FIG. 10).

In some embodiments, information including the order of annotations (e.g., the order of medical codes), the time taken to input an annotation, the clinical practitioner associated with an annotation, the date associated with an annotation, an indication of an annotation representing a chief complaint and/or principal diagnosis for a patient encounter, a present-on-admission indication for a medical code annotation, one or more clinical indicators and/or modifiers for a medical code annotation, and/or any other suitable information of potential interest may be received along with the user annotations and links. At stage 1330, the engine annotations and links and the user annotations and links may be merged into merged annotations and links. This merging may be accomplished, in some embodiments, by comparing the annotations and links from each source (e.g., from the engine and from one or more annotators) and removing redundant annotations and/or by comparing the order of annotations from each source and identifying differences. At stage 1340, training data including the merged annotations and links and the text may be provided to the NLU engine, and training of the NLU engine may be performed in any suitable manner. The NLU engine may use for training the corpus described at stage 1310, and the corpus need not be separately or additionally provided to the NLU engine in the form of the training data in some embodiments. However, for purposes of illustrating that the corpus may be used for training, the corpus is illustrated in FIG. 13 as being provided to the NLU engine distinctly in the form of the training data.

According to an additional aspect of the present application, training data for training a NLU engine may be generated by providing a free-form text to the NLU engine, using the NLU engine to generate medical billing codes (or other annotations) and links of the types described herein, and applying corrections by human annotators to the medical billing codes and links generated by the NLU engine. Such a process may be performed with "live" documents being used in a business (e.g., in a live production environment), rather than in a dedicated NLU training setting. For example, such a process may be performed in a medical office setting with the human annotator(s) (e.g., one or more medical coders) editing the NLU engine-generated medical billing codes or other annotations for the purpose of performing medical billing. In some embodiments, then, the process according to the present aspect of the application may be considered to be performed in real time with use of the NLU engine, and in some embodiments may be performed by a customer or other end-user of the NLU product rather than during development of the NLU product.

As discussed above, a CAC system may make use of the output from a trained NLU engine to provide information to the user, for example, via a CAC application that suggests medical billing codes for the documentation of a patient encounter analyzed by the NLU engine. The CAC application may present the suggested medical billing codes via an interface, along with other relevant information such as links to the underlying medical facts or evidence supporting the respective medical billing codes, and may provide user interface functionality (e.g., a GUI) that allows the user (e.g., a coder employed by a customer) to interact with the presented information (e.g., to view suggested medical billing codes and the supporting evidence in the documentation and to accept, reject, add, delete or otherwise edit or interact with the information). When the coder is finished editing and is comfortable with the results, the coder may finalize the set of codes for the patient encounter, which can then be sent, for example, to a payment provider to determine the level of reimbursement for the encounter according to set of codes that were accepted for submission.

Figure 14:
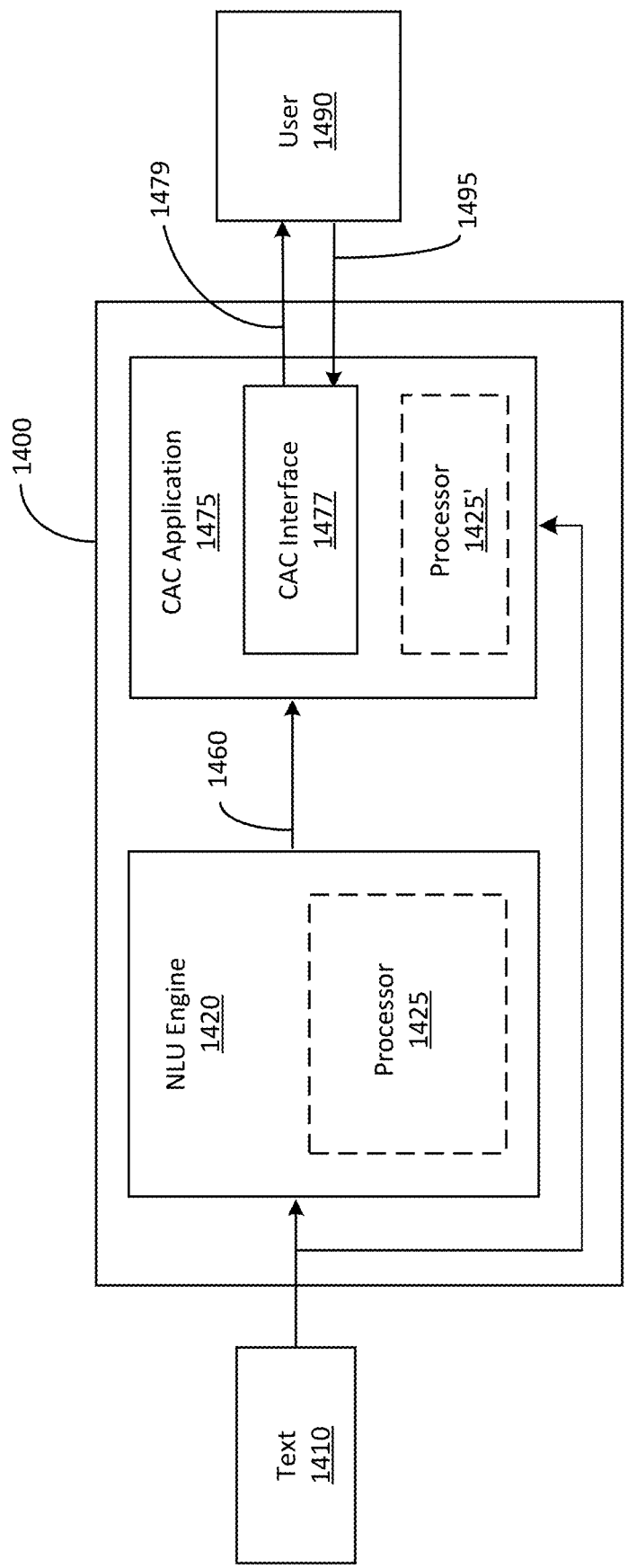
FIG. 14 is a block diagram of a CAC system comprising an NLU engine and a CAC application configured to suggest medical billing codes to a user, in accordance with some embodiments.

FIG. 14 is a block diagram of a CAC system 1400 that, among other functions, presents suggested medical billing codes to a user 1490 for a text 1410 documenting a patient encounter. CAC system 1400 may make use of a NLU engine 1420 (which may be implemented via a processor 1425) to analyze text 1410 to extract particular information provided to CAC application 1475 (which may be implemented via processor '1425) as annotations 1460. As discussed above, the term "annotation" refers to information detected in and/or derived from a portion of text, such as facts (e.g., a medical fact, one particular example of which may be a medical code), semantic labels, relationships between facts and/or semantic labels, etc.). An annotation typically also includes a link or reference to the portion of text from which it was derived. Text 1410 may include free-form text (in one or more documents) documenting one or more clinical patient encounters. The text 1410 may be in any suitable format and may have been obtained from any suitable source. For example, text 1410 may include a transcription of dictation from a physician documenting a patient encounter, transcribed using ASR, a human transcriptionist or a combination of both. Text 1410 may include text input by medical personnel documenting a patient encounter, or may include other text for which extraction of facts, semantic meaning, etc., may be desired, as the aspects are not limited with respect to the source or the nature of text 1410.

The NLU engine 1420 may analyze the text 1410 and generate annotations 1460 that are provided to CAC application 1475 as a basis for providing medical billing code suggestions 1479 that are presented to user 1490 via CAC interface 1477. As an example, text 1410 may include the sentence "These finding are likely related to diverticulitis." For this sentence, NLU engine 1420 may produce the following annotations 1460 for this portion of text 1410. The term "diverticulitis" may be detected as a medical fact of type DISORDER, the word "likely" may be detected as a fact of type HEDGE, and the "likely" and "diverticulitis" may be identified as having a relationship to one another. NLU engine 1420 may further assign an internal code to the medical fact "diverticulitis" extracted from text 1410 (e.g., NLU engine 1420 may assign the medical code 307496006, which is the SNOMED code for the disorder diverticulitis).

The above exemplary annotations extracted from this portion of text may then be provided (along with annotations extracted from other portions of the text being analyzed) in conjunction with text 1410 (or portions of text 1410 linked to by the annotations) to CAC application 1475 to assess whether any medical billing code should be suggested to the user. For example, user 1490 may be employed by a customer that performs medical coding in accordance with ICD10 codes, and CAC application 1475 may evaluate the above exemplary annotations to determine whether to suggest the ICD10 code of K57.92 corresponding to diverticulitis. That is, whether this portion of text documents a consequential billable event, or whether this mention of diverticulitis is inconsequential from a billing perspective. Similarly, CAC application 1475 may assess all annotations 1460 received from NLU engine in processing text 1410 to determine the set of medical billing codes 1479 to be presented to user 1490 via CAC interface 1477 for review and editing as needed.

As indicated above, NLU engine 1420 may assign medical codes to facts extracted from text 1410. These medical codes may be internal medical codes that differ from the medical billing codes suggested by the CAC application 1475. For example, NLU engine 1420 may assign SNOMED codes to medical facts and CAC application 1475 may suggest one or more ICD10 codes to medical facts based on evaluating the annotations 1460 (including the assigned SNOMED codes) produced by NLU engine 1420. Thus, the medical codes used internally by the NLU engine may, but need not, differ from the medical codes suggested to users by the CAC application for billing purposes. Use of internal medical codes may facilitate providing a customized CAC application 1475 that can derive medical billing code suggestions in accordance with the particular set of coding standards utilized by the customer. However, it should be appreciated that internal medical codes need not differ from the medical billing codes suggested to the user, nor is the use of internal medical codes a requirement, as the techniques described herein are not limited for use with any particular representation utilized by the NLU engine and/or CAC application.

It should be appreciated that other relevant information, in addition to suggested medical billing codes 1479, may be presented to the user via CAC interface 1477. For example, CAC interface 1477 may be similar to GUI 700 illustrated in FIGS. 7A-7G and may present any of the information and provide any of the functionality described in connection with GUI 700 to allow a user 1490 to interact with the CAC system, for example, to accept one or more suggested medical billing codes, edit one or more medical billing codes, add or delete one or more medical billing codes, increase the specificity of a medical billing code (e.g., if the medical billing codes and links include a generic medical billing code for a fracture while the corresponding text also indicates a dislocation for the same clinical patient encounter, user 1490 may replace the generic medical billing code for a fracture with a specific medical billing code for a fracture plus dislocation), or provide other feedback 1495 to the CAC system via CAC interface 1477 (e.g., reasons for a correction, modifications to the evidence supporting a medical billing code, etc.).

As discussed above, the inventors have recognized that a problem of many conventional CAC systems is unsatisfactorily high false positive rates in suggesting medical billing codes, leading to expensive and tedious manual correction and reduced customer satisfaction. More specifically, text regions having non-diagnostic language present a significant difficulty for conventional CAC systems in making correct medical billing code suggestions to the user. To provide a solution to this problem, inventors have developed diagnostic language relevance (DLR) components that are trained using user feedback to reduce the false positive rates of the CAC system in suggesting medical billing codes for documentation of a patient encounter. According to some embodiments, a DLR component is trained to assess the likelihood that particular regions of text are non-diagnostic in nature, or otherwise to not describe a billable event, based on user feedback in order to suppress false positive rates in suggesting medical billing codes to a user, further details of which are described below.

Figure 15:
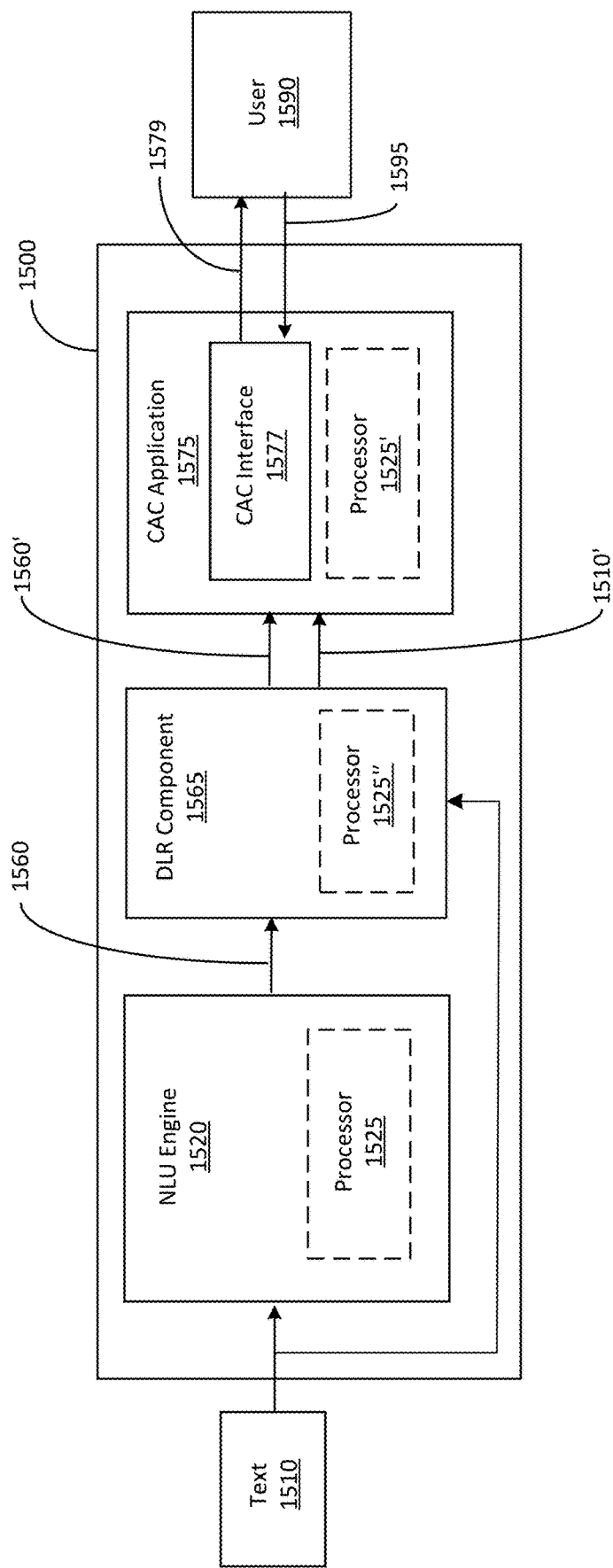
FIG. 15 is a block diagram of a CAC system utilizing a diagnostic language relevance (DLR) component configured to facilitate reducing false positive rates in suggesting medical billing codes to a user, in accordance with some embodiments.

FIG. 15 illustrates a CAC system 1500 in which a DLR component, trained at least in part on user feedback (e.g., a coder employed by a customer), is configured to reduce the false positive rate of the CAC system in suggesting medical billing codes, in accordance with some embodiments, thus addressing problems of conventional CAC systems in this respect. In many ways, CAC system 1500 may be similar to system 1400, making use of an NLU engine (e.g., NLU engine 1520) to analyze text (e.g., text 1510) to extract information from the text and derive annotations 1560 (e.g., medical facts and/or assigned medical codes, semantic labels, relationships, links to the corresponding evidence in the text itself, etc.) corresponding to respective portions of text 1510. At least some of the annotations 1560 output from NLU engine 1520 are provided to CAC application 1575 to evaluate the annotations and provide suggested medical billing codes 1579, via CAC interface 1577, to user 1590. The user 1590 interacts with CAC interface 1577 to review and edit the medical billing code suggestions made by the CAC system to, for example, accept, reject, modify, augment or supplement suggestions provided by CAC application 1575.

Additionally, CAC system 1500 includes a DLR component 1565 trained at least in part using feedback (e.g., feedback 1595 received from the user in reviewing suggested medical billing codes from the CAC system) to suppress false positive rates of the CAC system in suggesting medical billing codes to the user. DLR component 1565, for example, implemented by processor 1525" (which may be the same or different than processor 1525 and/or 1525'), is configured to receive text 1510 and may also be configured to receive annotations 1560 from NLU engine 1520 or some indication of which portions of text 1510 giving rise to one or more of annotations. DLR component 1565 is configured to analyze text 1510 (or portions indicated as giving rise to one or more annotations) and, depending on the analysis, may exclude one or more portions of text 1510 so that CAC application 1575 considers only text subset 1510' and, by virtue, evaluates only a subset of the annotations 1560'. For example, DLR component may evaluate text 1510 and determine that one or more regions of text 1510 are not diagnostically relevant and/or otherwise do not describe a billable event and, as a result, may exclude the identified one or more regions of text from further consideration by CAC application. In FIG. 15, DLR component 1565 is schematically illustrated as passing on text 1510' and annotations 1560' based on its analysis of text 1510 (and alternatively annotations 1560) to illustrate the effect of DLR component 1565. However, it should be appreciated that, in some embodiments, text 1510 and annotations 1560 from NLU engine 1520 may be provided to CAC application 1575, in full and/or directly, and DLR component 1565 may simply provide an indication to CAC application 1575 which portions of text 1510 and/or corresponding annotations 1560 should be ignored when suggesting medical billing codes to the user (e.g., as shown in FIG. 16 described below).

According to some embodiments, DLR component 1565 is configured to evaluate text 1510 (or text regions of text 1510 that gave rise to one or more annotations 1560) to determine the likelihood that regions of text from which one or more facts were extracted by the NLU engine are not relevant from a billing standpoint based on certain features of the text region. DLR component 1565 may then exclude the text region with low probability of being relevant (or a high probability of being irrelevant) from being evaluated by CAC application 1575. In this respect, DLR component 1565 may operate as a filter, eliminating some of the regions of text 1510 (and the corresponding annotations) that are likely sources of false positive medical billing code suggestions from further consideration by CAC application 1575 (e.g., text 1510' may be a subset of text 1510 with text regions deemed not to be relevant excluded and annotations 1560' may be a subset of annotations 1560 with the annotations derived from the excluded text regions removed from further consideration). As discussed above, rather than actively excluding text and annotations and providing subsets 1510' and 1560', DLR component 1575 may simply indicate which text regions and/or annotations should not be considered by CAC application 1575 when assigning and presenting medical billing codes to user 1590.

It should be appreciated that DLR component 1565 may be configured to reduce the rate at which CAC application 1575 suggests false positive medical billing codes in other ways, as the aspects are not limited in this respect. According to some embodiments, DLR component 1565 may be trained at least in part using user feedback to learn characteristics of text regions in documentation of patient encounters that frequently give rise to false positive medical billing code suggestions and/or to learn characteristics of text regions that frequently give rise to true positive medical billing code suggestions. Thus, the trained DLR component 1565 may evaluate text regions giving rise to annotations 1560 and identify which text regions exhibit characteristic features that the DLR component has learned are associated with high false positive rates (e.g., text regions including non-diagnostic content or that otherwise describe non-billable events) and/or identify which text regions exhibit characteristic features that the DLR component has learned are associated with high true positive rates. The DLR component may respond to this evaluation by excluding the former text regions from further consideration and retaining the latter text regions for further consideration in recommending medical billing codes to the end user (or alternatively indicating to the CAC application that the former text regions should not be further evaluated when suggesting medical billing codes to the user).

Figure 16:
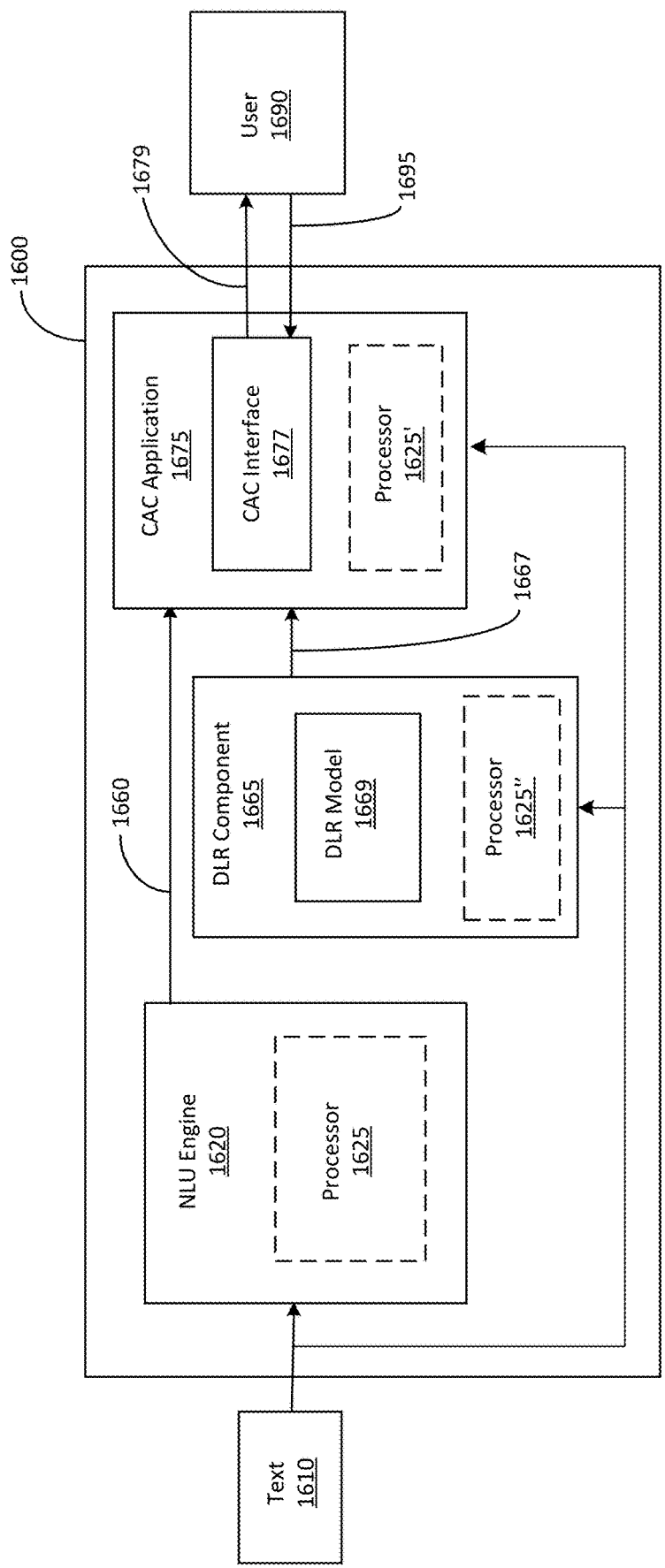
FIG. 16 is a block diagram of a CAC system comprising a DLR component having a DLR model trained to reduce false positive rates in suggesting medical billing codes to a user, in accordance with some embodiments.

FIG. 16 illustrates a CAC system 1670 having a DLR component 1665 comprising a DLR model 1669 to facilitate suppressing false positive medical billing code suggestions, in accordance with some embodiments. DLR component 1665, for example, implemented by processor 1625" (which may be the same or different than processor(s) 1625 and 1625' implementing NLU engine 1620 and CAC application 1675), may be configured to analyze text 1610 to exclude at least one text region from further evaluation by CAC application 1675 in suggesting medical billing codes to user 1690. For example, DLR component 1665 may analyze text 1610 and provide instruction 1667 to CAC application 1675 indicating which text regions of text 1610 (and corresponding annotations 1660) should be excluded from the CAC processes that assign and suggest medical billing codes to user 1690, thus preventing text regions deemed sufficiently likely to produce false positive rates from being further considered.

According to some embodiments, DLR model 1669 is configured to evaluate text regions to assess whether each text region is more like text regions associated with high false positive rates or high true positive rates to determine whether the text region should be excluded from consideration by CAC application 1675 as a basis for possible medical billing code suggestion(s). According to some embodiments, DLR model 1669 identifies text to be excluded from further consideration as a result of being trained so that it has learned the characteristic features of language that appears in documentation of a patient encounter that is not relevant from a billing perspective (e.g., includes non-diagnostic language such as risk assessment, precautions, etc., or otherwise does not describe a billable event) and therefore frequently gives rise to false positive medical billing code suggestions. For example, DLR model 1669 may be trained using feedback (e.g., customer feedback, expert feedback, etc.) to be able to classify text regions by comparing text regions to labeled clusters representing text regions generated during training of the model, examples of which are described in further detail below.

Figure 17:
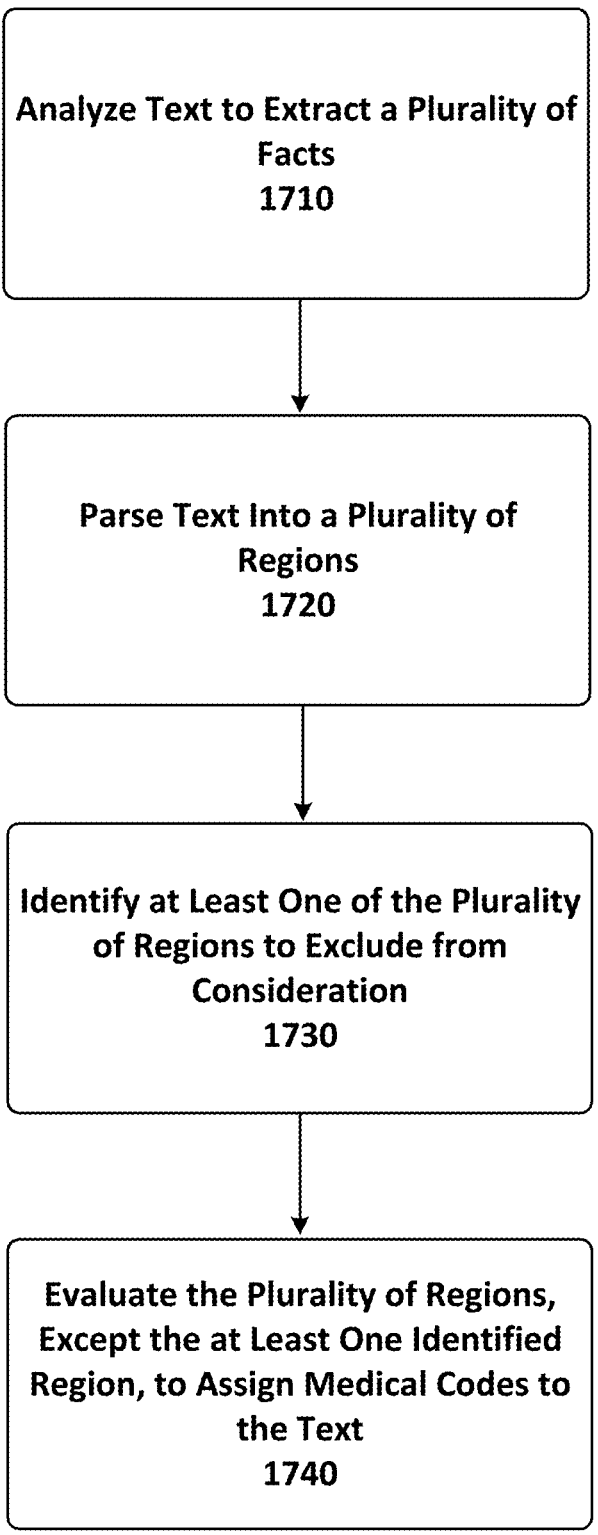
FIG. 17 is a flowchart of a method of reducing false positive rates in suggesting medical billing codes to a user, in accordance with some embodiments.

FIG. 17 is a flowchart illustrating a method of processing text comprising information regarding a patient encounter to facilitate accurately suggesting one or more medical billing codes to a user, in accordance with some embodiments. Method 1700 may be performed, for example, by a CAC system (e.g., the CAC systems illustrated in FIGS. 15 and 16) to reduce the number of false positive medical billing codes that are suggested to the user that require the user to edit or reject the incorrectly assigned medical billing codes. In act 1710, text is processed to extract a plurality of facts. For example, free-form text documenting a patient encounter may be processed by an NLU engine to extract a plurality of facts that, along with other pertinent information such as medical codes associated with at least some of the facts, semantic labels of the facts, relationships between facts and/or labels, etc., form annotations for the free-form text. As discussed above, the text may have resulted from transcribing physician dictation, either automatically, manually or combination of both, or the text may have resulted from another source, as method 1700 may be performed on any suitable text independent of the source.

In act 1720, the text is parsed into a plurality of regions. For example, the text may be parsed according to sections within the text, may be parsed into regions based on the regions of text associated with annotations extracted from the text, parsed into paragraphs, sentences or parsed in any other suitable manner. According to some embodiments, the text is parsed into separate paragraphs where each paragraph is the set of words delimited by a blank line (e.g., a blank line in the text is presumed to indicate the start of a new paragraph). According to some embodiments, each of the plurality of regions corresponds to the textual evidence underlying a medical code annotating the text region as determined by an NLU engine. The plurality of text regions can be of any size or makeup, as parsing the text into a plurality of regions is not limited to any particular one or combination of techniques.

In act 1730, at least one of the plurality of regions is identified for exclusion from further consideration when providing medical billing code suggestions to a user. For example, one or more text regions may be identified as having a high likelihood of giving rise to one or more false positive medical billing code suggestions and therefore may be excluded from evaluation to avoid erroneous medical billing codes being assigned to the text and suggested to the user. According to some embodiments, act 1730 is performed by a trained DLR component configured to evaluate text regions to identify text regions that are consistent with those that have given rise to false positives in the past (e.g., language that is not clinically relevant or that are inconsequential from a billing perspective). For example, a DLR component may have been trained using user feedback obtained from users reviewing and correcting medical billing codes that were suggested to the user to learn the language and contexts that give rise to false positive medical billing code suggestions. According to some embodiments, text regions (or representations thereof) are compared to a model that has learned characteristics that have given rise to relatively high false positive rates and/or relatively high true positive rates to classify the region of text accordingly. Regions of text that are classified as having a sufficient likelihood of giving rise to false positive medical billing codes suggestions may be excluded from further consideration. Details regarding training an exemplary DLR component are discussed in further detail below.

In act 1740, the text is evaluated, except for the text regions identified in act 1730, to provide suggested medical billing codes to the user. For example, a text documenting a patient encounter, except for those text regions identified for exclusion from further consideration in act 1730, may be evaluated by a CAC application to assign medical billing codes that are presented to a user as suggestions so that the user can review and edit as needed. As discussed above, a DLR component configured to reduce false positive rates of a CAC system in suggesting medical billing codes may be trained based at least in part on user feedback. In particular, user feedback may be used as "ground truth" with respect to whether portions of documentation from which one or more facts were extracted was correctly or incorrectly assigned one or more medical billing codes (e.g., the training data may be labeled according to whether a user accepted or rejected a medical billing code suggested by the CAC application). Using this information, a DLR component can be configured to distinguish between text regions that are likely to produce false positive medical billing code suggestions and those that are likely to produce true positive medical billing code suggestions, examples of which are described in further detail below.

Figure 18:
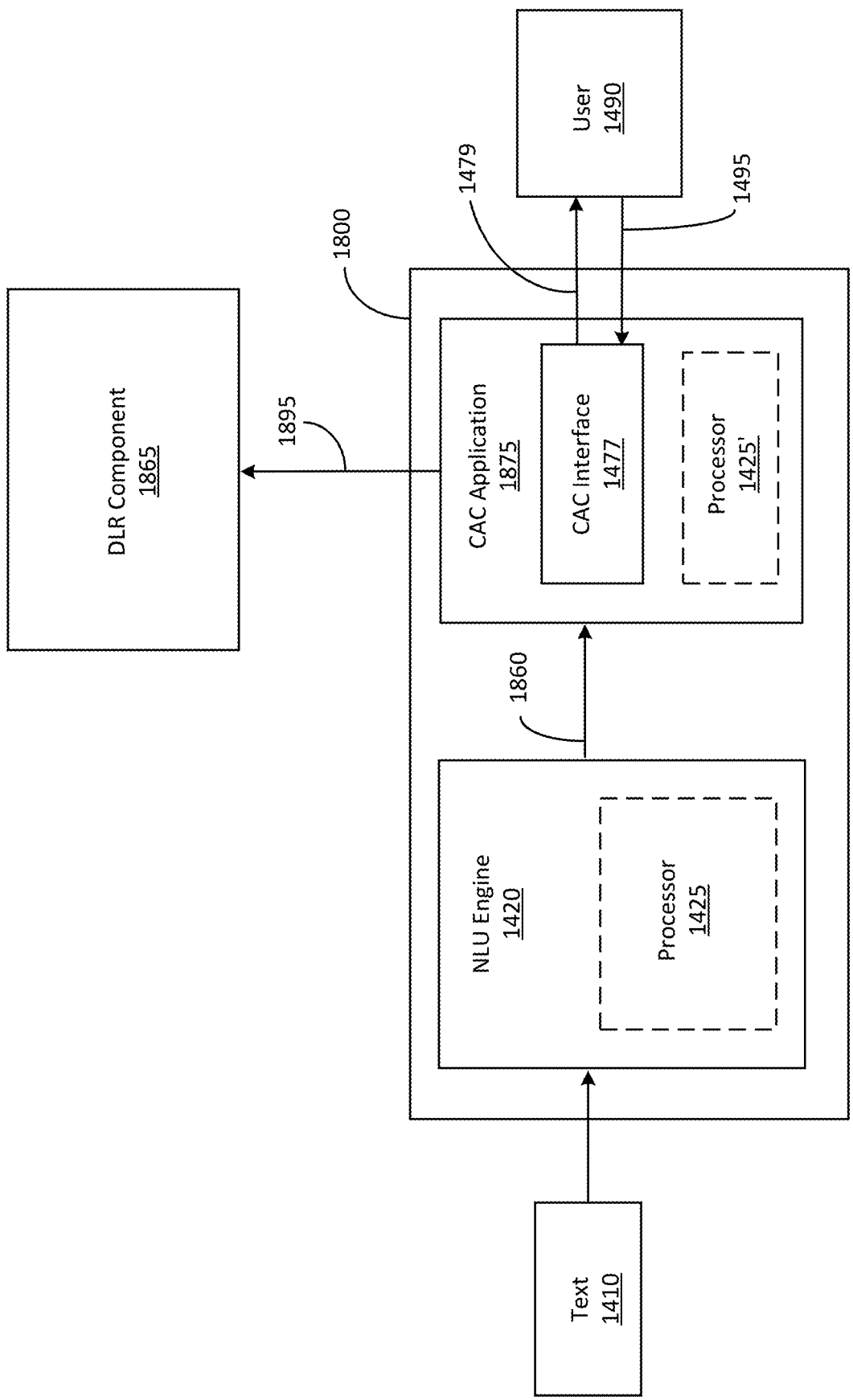
FIG. 18 is a block diagram of a DLR component trained based in part on feedback from a CAC system, in accordance with some embodiments.

FIG. 18 illustrates a DLR component 1865 that is trained using training data 1895, which may include or be based on information associated with, or obtained as a result of, user 1490 interacting with a CAC application 1875 system. As discussed above, user 1490 may interact with CAC application 1875 via a CAC interface 1477 that allows user 1490 to add, delete, modify, accept, reject and/or otherwise provide feedback 1495 to CAC application 1875 regarding the medical billing codes suggested by the CAC application. This information provides information about instances where medical billing codes were correctly assigned by the CAC application and instances where medical billing codes were incorrectly assigned by the CAC application. This feedback can be used to train a DLR component to facilitate reducing false positive rates of the CAC application. For example, user feedback 1495 can be used to identify text regions that are prone to give rise to erroneous medical billing code suggestions (e.g., medical billing code suggestions that are rejected by a user). User feedback 1495 can also be used to identify text regions that tend to give rise to correct medical billing codes suggestions (e.g., medical billing code suggestions accepted by a user). This user feedback may be the focus of the training data 1895 used to train DLR component, though DLR component 1865 may be trained in any suitable way. For example, training data 1895 may also include feedback from an expert (e.g., an independent expert not employed by a customer) that provides feedback on medical billing codes suggested by CAC application 1875.

Training data 1895 used to train DLR component 1865 may include any relevant information associated with, obtained from, based on and/or derived from feedback 1495 received from user 1490, as well as any other suitable information obtained from other sources, some example of which are discussed below. For example, user feedback 1495 may indicate that a particular medical billing code was erroneously assigned by the CAC application based on one or more facts extracted from a corresponding portion of text 1410. In view of this feedback, the corresponding text region may be included in training data 1895 to provide example context where text was assessed as being clinically relevant from a billing perspective but was in fact not clinically relevant or otherwise described a non-billable event. False positive and true positive examples may be compiled and added to training data 1895 to provide a corpus of information by which DLR component 1865 is trained.

Training data 1895 may be used to establish a rules-based DLR component 1865, train a statistics-based DLR component 1865 (e.g., to train a statistical model, machine learning model, etc.), provide a combination of both rules-based and statistics-based, or otherwise train a DLR component configured to reduce false positive rates of CAC application 1875 in suggesting medical billing codes to a user (e.g., by excluding text and the fact(s) derived therefrom from consideration by CAC application 1875). With respect to a rules-based approach, the training data 1895 may be analyzed by an expert to produce a set of rules that, when applied to documentation of a patient encounter during operation, determine whether a region of text from documentation of a patient encounter is consequential or not (e.g., is the text region clinically relevant for purposes of billing). With respect to statistical-based approaches, training data 1895 may be introduced to a machine learning model to learn the characteristics of text that tend to produce false positive and true positive medical billing code suggestions, examples of which are described in further detail below. A combination of statistical-based approaches and a rules-based approach may also be used, examples of which are described below. Once trained, DLR component 1865 may be utilized by CAC system 1800, for example, as discussed above in connection with the CAC systems 1500 and 1600 illustrated in FIGS. 15 and 16, respectively, and as described by method 1700 illustrated by the flowchart of FIG. 17.

Figure 19:
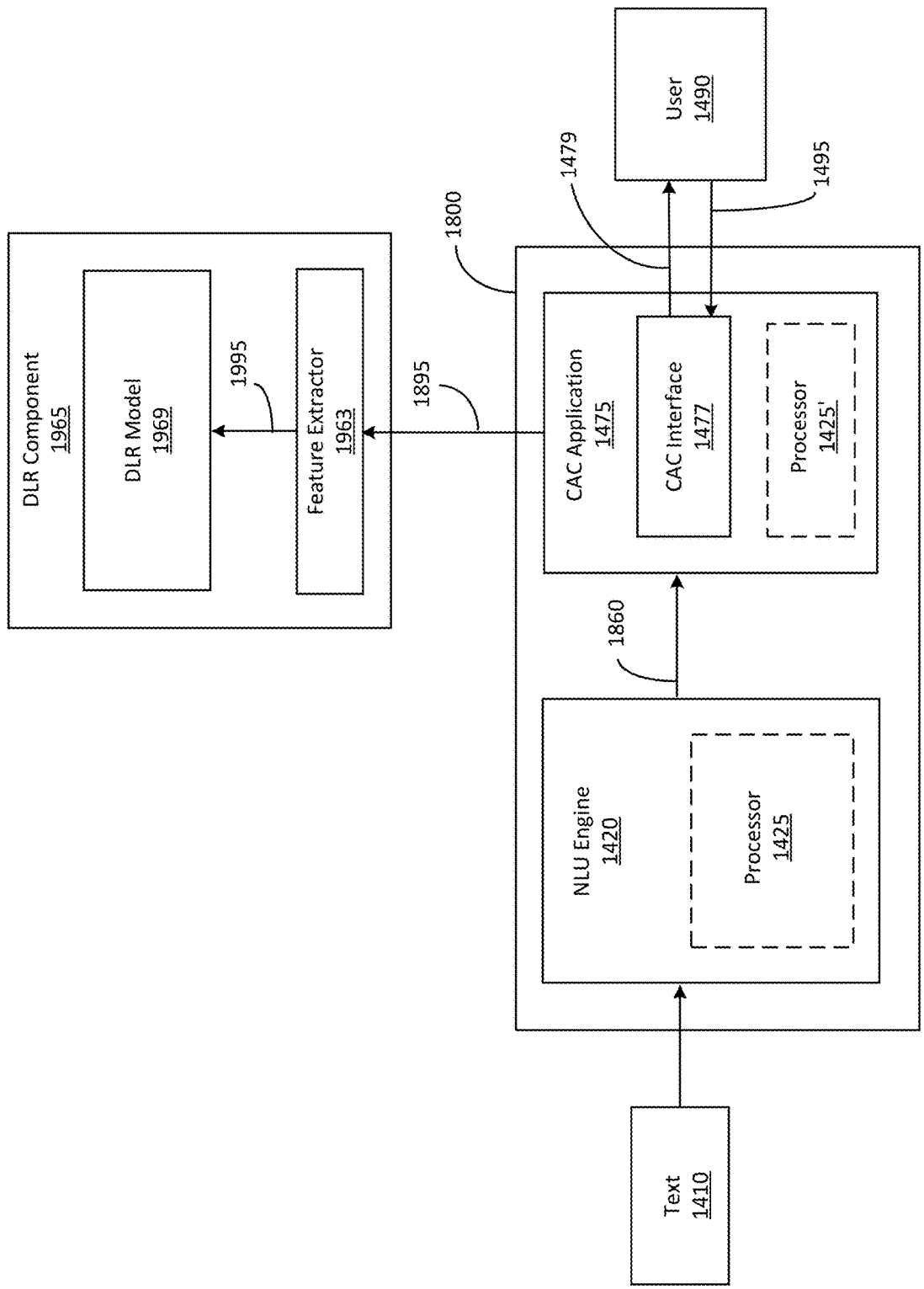
FIG. 19 is a block diagram of a DLR component comprising a DLR model trained based in part on features extracted from feedback from a CAC system, in accordance with some embodiments.

FIG. 19 illustrates a DLR component 1965 that comprises a DLR model 1969 that is trained using features 1995 extracted from training data 1895 by feature extractor 1963. For example, feature extractor 1963 may be configured to extract salient features from training data 1895 that facilitate DLR model 1969 learning the characteristics of text regions that are prone to give rise to false positive medical billing code suggestions and/or characteristics of text regions that tend to give rise to true positive medical billing code suggestions. As discussed above, once trained, DLR component 1965 may be used to evaluate the likelihood that text regions from a given text 1410 will result in one or more false positive medical billing code suggestions based on the learned characteristics and/or context. A number of rule based and/or statistic models (e.g., machine learning models such as statistical classifiers) may be used to embed and/or learn the characteristics of text to predict whether a given text region is likely to produce false positive medical billing code suggestions that may be suitable for implementing DLR component 1965, some examples of which are described in further detail below.

As discussed above, the inventors have recognized that certain characteristics of text may be indicative of whether the text is clinically relevant from a diagnostic perspective (e.g., whether it describes a billable event), or whether the text should be ignored for purposes of assigning medical billing codes. According to some embodiments, feature extractor 1963 converts the training data into a plurality of text regions that can be transformed or converted to a representation on which a clustering algorithm can be performed. For example, a text-to-vector representation made be used to convert text regions into vectors that can be compared in vector space. By transforming text regions into a vector space, any of various clustering techniques may be used to identify clusters of training data that are "near" each other in a given vector space. However, other representations of respective text regions may be used, as the aspects are not limited in this respect.

The inventors have recognized that language embedding may be used to derive a representation of text regions that can be used to distinguish between, for example, diagnostically relevant and irrelevant text from a billing perspective (e.g., a representation that facilitates distinguishing between text that describes billable and non-billable events). For example, some language embedding techniques may transform text into a vector space where semantically similar text appears closer in vector space than does semantically dissimilar text and/or where text with similar content appears closer in vector space than does text with dissimilar content. In this manner, text regions that are not diagnostically relevant may transform into vectors that tend to cluster in vector space and text regions that do include diagnostically relevant information (e.g., relevant from a billing perspective) may also tend to cluster in vector space. This separation in vector space may provide an indication of whether a given text region is likely to be relevant from a billing perspective or whether it is likely to be diagnostically irrelevant and so produce a false positive medical billing code suggestion.

According to some embodiments, a DLR model may be trained by converting each text region in the training data into a fixed-length representation of the text, for example, using a language embedding technique. Word or language embedding refers herein to any technique that learns fixed-length representations from variable-length text. In this way, variable-length text can be converted to a fixed-length representation (e.g., a vector) that can be used for training a cluster model and for subsequently evaluating variable-length text using its corresponding fixed-length representation. Techniques for training a DLR model comprising a language embedding model and a cluster model to facilitate reducing false positive rates of a CAC application in suggesting medical billing codes are discussed in further detail below.

Figure 20B:
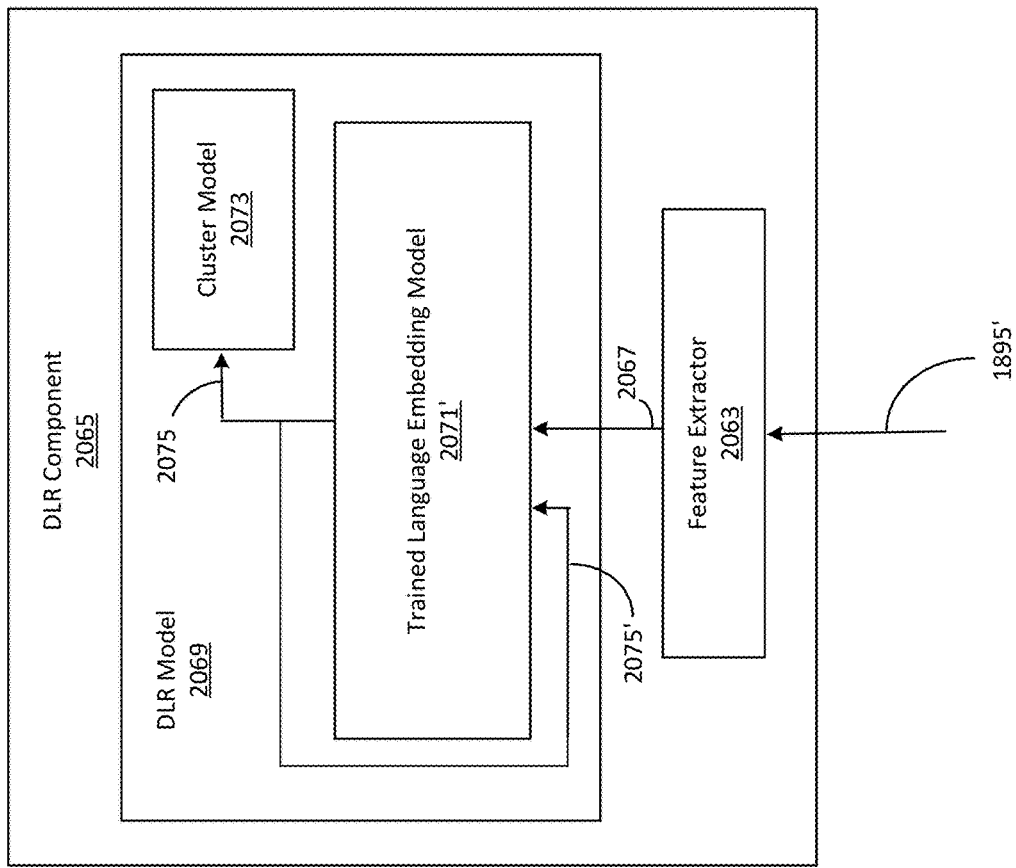
FIGS. 20A and 20B are block diagrams of a DLR component comprising a DLR model trained using a first stage to train a language embedding model and a second stage to produce a cluster model, in accordance with some embodiments.
Figure 20A:
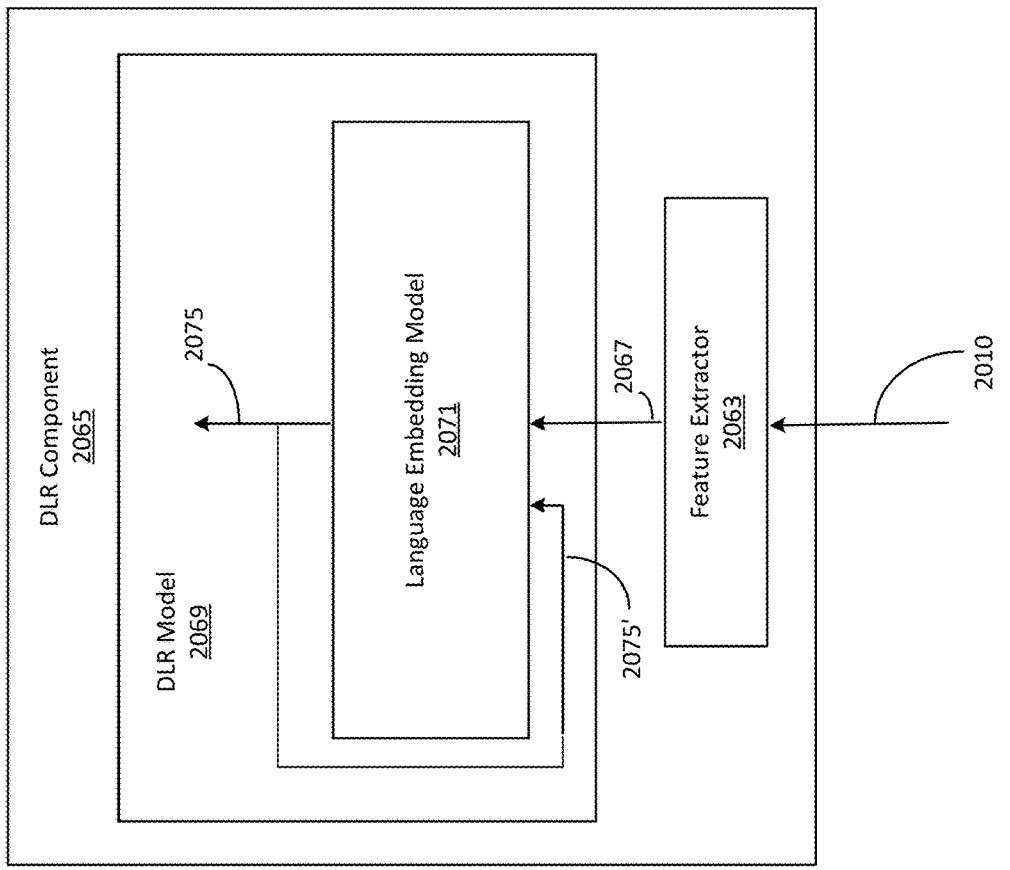

FIGS. 20A and 20B illustrate training a DLR component 2065 in two stages: 1) a first training stage illustrated in FIG. 20A configured to train a language embedding model 2071 of DLR model 2069; and 2) a second training stage illustrated in FIG. 20B configured to provide cluster model 2073 of DLR model 2069 using the trained language embedding model 2071'. In FIG. 20A, language embedding model 2071 is trained using training data 2010. Training data may comprise a corpus of text compiled from documentation of patient encounters. For example, a DLR component 2065 may be trained for a particular customer and training data 2010 may comprise a corpus of documentation of patient encounters associated with the customer (e.g., documentation of patient encounters for a particular hospital or other medical or healthcare institution). However, it should be appreciated that training data 2010 may be compiled from different sources and need not be limited to a particular institution or customer, as the aspects are not limited in this respect. Language embedding model 2017 may undergo unsupervised training (e.g., training data 2010 may be unlabeled text).

Feature extractor 2063 may operate to partition the text into paragraphs or some other suitable text region. For example, according to some embodiments, training data 2010 is processed to parse the text into text regions separated by a blank line. That is, feature extractor 2063 may process the training data 2010 in standard reading order (left to right, top to bottom) and assign successive words to the same text region until a blank line in the training data 2010 is encountered. Words following a blank line are grouped into a subsequent text region until the next blank line is encountered. In this manner, training data 2010 can be segmented into paragraphs (or an approximation of paragraphs) to provide a plurality of text regions with which to train language embedding model 2071. Small text regions (e.g., text regions that have fewer than a threshold number of words) may be appended or prepended to an adjacent text region. It should be appreciated that segmenting training data 2010 into paragraphs is only one method of partitioning the training data and training data 2010 may be parsed into text regions into any desired grouping of words (e.g., sentences) in any suitable way, as the aspects are not limited in this respect.

Thus, features 2067 provided to language embedding model may be words grouped into paragraphs (or an estimate of paragraphs) or words grouped into text regions based on proximity or one or more other factors or criteria (e.g., words in a section, field, etc.). Features 2067 are then provided to language embedding model 2071 to train the language embedding model to produce an output 2075 that may be representative of some aspect of the text region (e.g., semantic content, word content, contextual meaning, etc.). According to some embodiments, the result of training language embedding model 2071 is that the trained model 2071' produces output 2075 that tends to be more similar for semantically similar text regions and tends to be more dissimilar for semantically dissimilar text regions. According to some embodiments, the result of training language embedding model 2071 is that the trained model 2071' produces output 2075 that tends to be more similar for text regions that have similar word content and/or word arrangement and tends to be more dissimilar for text regions that have dissimilar word content and/or word arrangements. According to some embodiments, output 2075 is an n-dimensional vector that can be used as a characteristic vector for the corresponding feature 2067 (e.g., paragraph, sentence, section, or other text region) that can be compared to other characteristic vectors, as discussed in further detail below. As illustrated in FIG. 20A, output 2075 is utilized as feedback 2075' to train the language embedding model in an iterative manner. According to some embodiments, feedback 2075' is initialized to some value (e.g., a pre-determined or an arbitrary value) for the first iteration for a corresponding feature 2067 or at the beginning of training.

Figure 21:
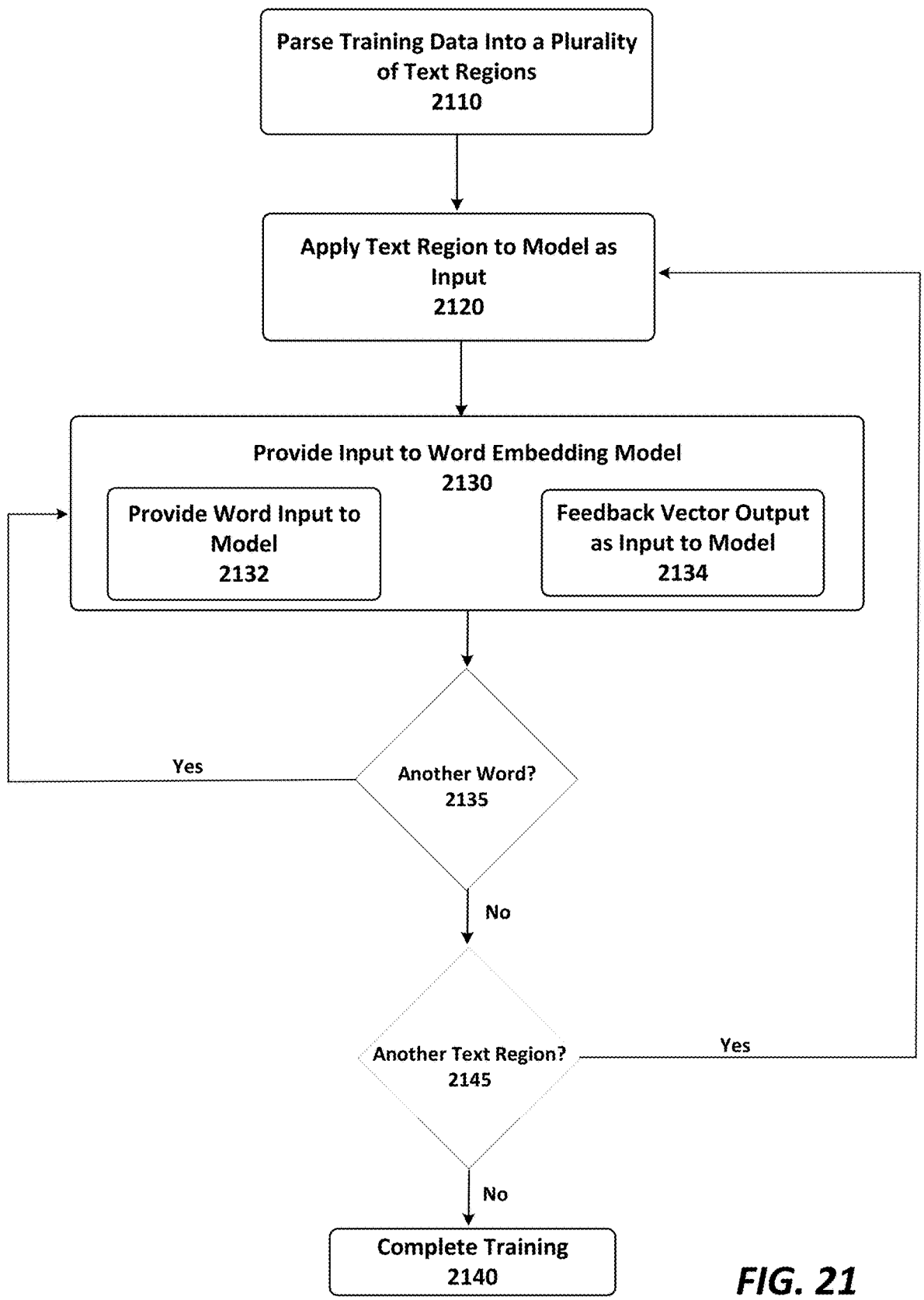
FIG. 21 is a flowchart illustrating a method of training a language embedding model, in accordance with some embodiments.

FIG. 21 illustrates an exemplary method of training a language embedding model (e.g., language embedding model 2071 illustrated in FIG. 20A), in accordance with some embodiments. In act 2110, training data is parsed into a plurality of text regions. As discussed above, training data may be obtained by collecting a corpus of text from documentation of patient encounters, for example, a healthcare institution's archive of medical reports obtained from clinicians reporting on patient encounters. The training data may be parsed into a plurality of paragraphs (e.g., the training data may be parsed into text regions demarcated by a blank line) or any other suitable text regions (e.g., sentences) for use in training a language embedding model. It should be appreciated that the training corpus may include any number of documents deemed sufficient to expose the language embedding model to enough training data (e.g., tens, hundreds, thousands, tens of thousands, hundreds of thousands of documents or more).

In act 2120, a first text region of the plurality of text regions is applied to the language embedding model for training. According to some embodiments, the language embedding model is a word2vec or paragraph2vec technique in which a word is input into the model and a representative vector is output. The model may be, for example, a neural network or other suitable machine learning framework. According to some embodiments, a text region is applied to the language embedding model by providing each word in the text region as input to the language embedding model. For example, in act 2130, a first word in the first text region may be provided as input to the language embedding model (act 2132) and to produce an output vector. The output vector is fed back to the language embedding model (act 2134) as an input in conjunction with the next word in the first text region. According to some embodiments, the vector is initialized to a predetermined value on the first iteration (e.g., the first word of a text region may be input to the language embedding model along with a vector input initialized to a predetermined value) and the vector is modified by the language embedding model in response to the input word, thus being transformed to the output vector that is fed back to the input of the model on the next iteration. However, it should be appreciated that this specific framework is only an exemplary implementation, and a language embedding model can be implemented in other ways, as the aspects are not limited in this respect.

Each word in a text region is input, in turn (e.g., successively), to the language embedding model and a corresponding vector is output and fed back as input to the language embedding model on the next iteration until the last word in the text region has been input to the language embedding model (2135). According to some embodiments, the process of providing each word in a text region to the language embedding model is repeated a desired number of times (e.g., until the output vector converges) before moving to the next text region in the training data. According to some embodiments, however, each word in a given text region may be provided as input to the language embedding model a single time before applying the next text region to the language embedding model (e.g., by repeating acts 2120 and 2130 on the next of the plurality of text regions). This process may be repeated for each of the plurality of text regions in the training data to train the language embedding model (2145). Once each text region in the training data has been processed by the language embedding model at least once, initial training of the language embedding model may be completed (act 2140). The trained language embedding model may then be used to generate a cluster model, examples of which are described in further detail below.

Referring to FIG. 20B, trained language embedding model 2071' (e.g., a language embedding model trained using the exemplary technique described in connection with FIG. 21A) is used to produce a cluster model 2073 based on feedback data 1895', in accordance with some embodiments. As discussed above, a CAC application may provide medical billing code suggestions to a user who may, in turn, review and edit the medical billing code suggestions (e.g., via a CAC interface). Whether a user accepts, rejects, replaces or otherwise edits a medical billing code suggestion provides useful feedback that can be used to improve the performance of the CAC application is suggesting medical billing codes. For example, when a user corrects (e.g., replaces, deletes, etc.) a suggested medical billing code, the text region that gave rise to the incorrect medical billing code suggestion (e.g., the text from which one or more medical facts were extracted by an NLU engine that gave rise to an incorrect medical billing code suggested by the CAC application) can be flagged as a false positive text region. Similarly, when a user accepts a suggested medical billing code, the text region that gave rise to the correct medical billing code suggestion (e.g., the text from which one or more medical facts were extracted by an NLU engine that gave rise to a correct medical billing code suggested by the CAC application) can be flagged as a true positive text region. In this way, feedback data 1895' that includes examples of text regions that produced false positive medical billing code suggestions and true positive medical billing code suggestions can be compiled from user feedback via a respective user's editing and acceptance of suggested medical billing codes.

It should be appreciated that feedback data 1895' need not be provided by users employed by customers and/or exclusively by users employed by customers. For example, coding experts that are not affiliated with a customer may review medical billing code suggestions and provide feedback regarding correct and incorrect medical billing code suggestions. This feedback may be used alone or to supplement user feedback to train DLR component 2065. Accordingly, feedback 1895' may be obtained from customer users, non-customer personnel (e.g., hired coding experts), or a combination of both. Whatever the source, feedback data 1895' may be used to provide a cluster model that can be used to evaluate whether, during deployment of the DLR component after training, a text region is likely to produce a false positive medical billing code suggestion.

In FIG. 20B, feature extractor 2063 may segment a corpus of documentation (training data '1895') for which suggested medical billing codes have been reviewed by a user into a plurality of text regions. For example, feature extractor 2063 may parse the documentation into paragraphs, as described in connection with FIG. 20A (e.g., by using blank lines as paragraph delimiters). However, feature extractor 2063 may parse the training data 1895' into other regions such as sentences, sections, etc., as the aspects are not limited in this respect. Generally, feature extractor 2063 parses the training data 1895' into text regions in the manner in which the training data 2010 was parsed, however feature extractor 2063 is not limited to doing so.

Because of the feedback, it is known whether a text region gave rise to one or more false positives, one or more true positives, or a combination of both. According to some embodiments, only text regions giving rise exclusively to false positive medical billing code suggestions or exclusively to true positive medical billing code suggestions are used in the second stage of training DLR component 2065. Specifically, text regions 2067 may be labeled as false positive when giving rise exclusively to false positive medical billing code suggestions and text regions may be labeled as true positive when giving rise exclusively to true positive medical billing code suggestions. Text regions giving rise to a combination of false and true positive can be discarded. It should be appreciated, however, that text regions giving rise to both false and true positive medical billing code suggestions may be utilized in some implementations and labeled accordingly (e.g., text regions can be labeled as a ratio of false to true positives, as a percentage of false positives, etc.), as the aspects are not limited in this respect.

Text regions 2067 extracted from feedback data 1895' may each be applied to trained language embedding model 2071' to obtain a respective characteristic vector 2075, each characteristic vector 2075 labeled according to whether it resulted from a false positive or a true positive text region (or a combination in implementations that utilized mixed text regions) input to the trained language embedding model 2071'. The set of characteristic vectors 2075 resulting from applying each text region 2067 (e.g., each false positive and true positive text region extracted from feedback data 1895') may undergo a clustering algorithm to identify and label clusters of characteristic vectors that are located in proximity to one another to produce cluster model 2073.

As one example, each characteristic vector may be treated as a point in an n-dimensional vector space, where n is the length of the characteristic vectors output from trained language embedding model 2071'. A clustering algorithm such as k-means clustering, Gaussian mixture models (GMMs), k-nearest neighbors, etc. may be applied to the characteristic vectors to identify k clusters, each having a respective representative vector (e.g., a representative vector corresponding to the cluster centroid or mean vector of the m characteristic vectors that are identified as being part of or members of the respective cluster). By performing clustering, each of the characteristic vectors can be associated with one of k clusters represented by the centroid or mean vector of the respective cluster. According to some embodiments, cluster model 2073 stores the representative vector for the cluster and one or more labels. The one or more labels may include information or statistics on the cluster such as one or any combination of the percentage of false positive characteristic vectors that are members in the cluster, ratio of false positive characteristic vectors to true positive characteristic vectors that are members in the cluster, number of total member characteristic vectors, etc. Cluster model 2073 may also retain each of the characteristic vectors that underwent the clustering algorithm though, in some embodiments, the characteristic vectors themselves may be discarded. It should be appreciated that any information useful in labeling the cluster or for use in evaluating characteristic vectors during deployment of the trained DLR component 2065 may also be stored by or incorporated into cluster model 2073.

Cluster model 2073 may include any number of clusters and the number of clusters may be selected based on feedback data 1895'. As discussed above, according to some embodiments, a DLR component is trained for specific customers using training data obtained only from the respective customer, thereby allowing the DLR component to learn the preferences and billing behaviors of the specific customer. The different coding practices, priorities and preferences of specific customers may result in a set of characteristic vectors that cluster differently in the n-dimensional vector space and that may be best represented by a different number of clusters. Accordingly, the characteristic vectors derived from training data for a first customer may be better characterized using $k_1$ clusters, while the characteristic vectors derived from training data for a second customer may be better characterized using $k_2$ clusters. The number of clusters may include tens, hundreds or more clusters and the number of clusters may be chosen depending on the given set of characteristic vectors derived from the training data (e.g., on a per customer basis). In this way, a customer-tailored cluster model 2073 may be generated to train a DLR component that improves the accuracy and performance of a CAC application for the respective customer.

Once the cluster model 2073 has been determined (e.g., the set of characteristic vectors obtained from providing appropriate text regions extracted from feedback data 1895' as input to trained language embedding model 2071' have been clustered and the clusters labeled), it may be used to assess the likelihood that text regions will produce false positive medical billing code suggestions during operation and use of a CAC application. In particular, a given text region undergoing evaluation for diagnostic relevance may be input to the trained language embedding model 2071' to produce a corresponding characteristic vector that can be compared to cluster model 2073 to identify which cluster the characteristic vector is nearest. The label of the nearest vector may be used to assess whether the text region is likely to produce a false positive medical billing code suggestion.

The nearest cluster may be identified according to which cluster has a representative vector that is closest to the characteristic vector (e.g., the Euclidean distance, cosine distance, etc., between the cluster representative vector and the characteristic vector of the text region being evaluated). As another example, the nearest cluster may be identified by determining the distance between the characteristic vector and the distribution of characteristic vectors in each cluster (e.g., a Mahalanobis distance) and selecting the smallest distance. The nearest cluster may then be used to determine the likelihood that the corresponding text region will result in a false positive medical billing code suggestion (e.g., by evaluating the nearest cluster label, as discussed in further detail below). According to some embodiments, in addition to the nearest cluster being identified, the next one or more nearest clusters may also be identified in evaluating whether the text is likely to produce false positives. For example, the nearest j clusters may be identified and considered when determining whether a text region is likely to produce false positive medical billing code suggestions (e.g., whether or not the text region describes a billable event).

As discussed above, language embedding can be used to produce characteristic vectors whose distance from one another in vector space is related to the similarity in content, semantic meaning and/or word similarity of the text that gives rise to the respective vectors. Nonetheless, many clusters will include a combination of false positive characteristic vectors (e.g., characteristic vectors resulting from text regions from which false positive medical billing codes were derived) and true positive characteristic vectors (e.g., characteristic vectors resulting from text regions from which true positive medical billing codes were derived). Accordingly, each of the k clusters resulting from the clustering algorithm may be labeled with one or more values indicative of how strongly they reflect false positive text regions and/or true positive regions. For example, each cluster may be labeled with the percentage of the characteristic vectors in the cluster that arose from false positive text regions, the ratio of the number of characteristic vectors in the cluster that arose from false positive text regions to the number of characteristic vectors in the cluster that arose from true positive text regions, the number of characteristic vectors in the cluster and/or any other measure indicating how strongly a cluster reflects false positive text regions or true positive text regions or information that can be used to derive such a measure.

By labeling the clusters in this manner, a given text region can be assessed for how likely it is that a false positive medical billing code will be suggested (e.g., by assessing whether the most similar texts in the training data correspond to descriptions of non-billable events or observations). For example, the labels of one or more nearest clusters to a characteristic vector undergoing evaluation for diagnostic relevance may be assessed to determine whether the corresponding text region is likely to produce a false positive medical billing code suggestion. It should be appreciated that any information may be used to label the clusters (e.g., information stored in association with the respective clusters), as the aspects are not limited in this respect. According to some embodiments, each cluster is labeled as either a false positive cluster or a true positive cluster according to a predetermined criteria, for example, a criteria using one or more of the values described above (e.g., percentages, ratios, etc.). By labeling each cluster as either a false positive cluster or a true positive criteria according to how strongly the cluster reflects the former or the latter, a characteristic vector corresponding to a text region undergoing evaluation for diagnostic relevance can be quickly assessed as to whether it is sufficiently likely to produce false positive medical billing code suggestions.

Figure 22:
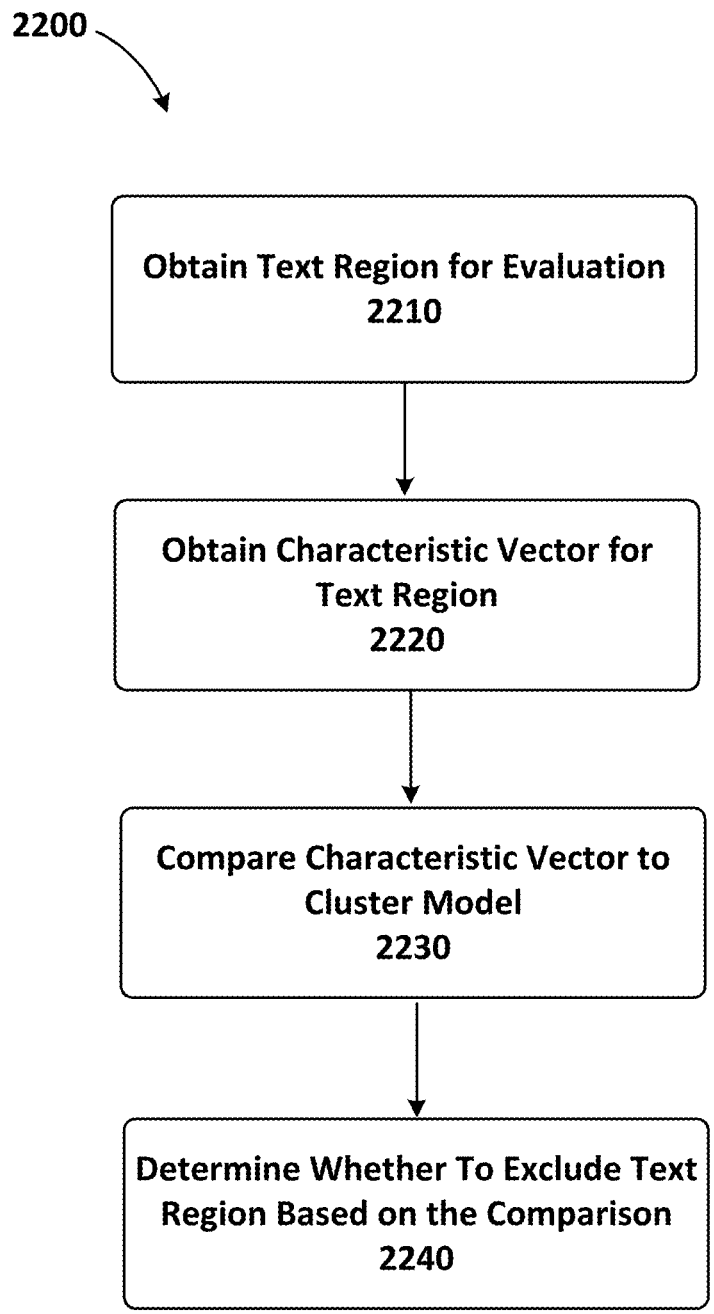
FIG. 22 is a flowchart illustrating a method of evaluating whether to exclude a text region from consideration when suggesting medical billing codes, in accordance with some embodiments.

FIG. 22 illustrates a method of determining whether a text region should be excluded from further consideration in suggesting medical billing codes to a user, in accordance with some embodiments. For example, DLR component 2065, trained using any of the techniques described herein (e.g., in connection with FIGS. 20A and 20B) may be used to perform method 2200. In act 2210, a text region to undergo diagnostic relevance evaluation is obtained. For example, a paragraph from a text documenting a patient encounter may be obtained from the text to evaluate whether the paragraph is diagnostically relevant (e.g., whether it describes a billable event or observation), or whether it should be excluded from further consideration when assigning medical billing codes to be presented to a user (e.g., suggested to a user employed by a customer via a CAC application). While text region can be a paragraph in some embodiments (e.g., a text block delimited by blank lines), the text region may be a word, phrase sentence, section (e.g., block of text delimited by section headings) or any desired set of words for which evaluation is desired, as the aspects are not limited in this respect.

In act 2220, a characteristic vector is produced from the text region. For example, the text region may be applied to a language encoding model that has been trained on a corpus of documentation of patient encounters, responsive to which the language encoding model produces a characteristic vector. According to some embodiments, the language encoding model is similar to trained language encoding model 2071' illustrated in FIG. 20B, and the text region is applied to the model (e.g., one word at a time) with the vector output for each word fed back as an input to the model along with the subsequent word in the text region. This process may be repeated until the output vector converges or substantially converges (e.g., the output vector ceases to change or change substantially when successive words are applied to the model). It should be appreciated that each word in the text region may be applied to the model a single time or multiple times before the output of the model converges. For example, the text region may be applied to the model by successively inputting the words in the text region repeatedly until the output vector converges. The output vector produced when the model converges (or converges sufficiently) may be used as the characteristic vector.

It should be appreciated that the process of applying a text region to a model may differ depending on the type of model and how the model produces characteristic vectors from respective text regions. For example, some of the techniques for applying a text region are suitable for language embedding models such as conventional word2vec or paragraph2vec algorithms that seek to predict the next word in a text region. The inventors have recognized that such language embedding models, when trained using techniques described herein, produce characteristic vectors that tend to cluster in a meaningful way with respect to the diagnostic relevance of the corresponding text, facilitating an accurate predictor of whether corresponding text describes a billable event (e.g., providing for more accurate assessment than may be achievable using other techniques such as statistical classifiers, bag of words, principal component analysis, etc.)

In act 2230, the characteristic vector is compared to a cluster model, for example, a cluster model similar to cluster model 2073 described in connection with FIG. 20B. According to some embodiments, comparing the characteristic vector to the cluster model includes identifying one or more nearest clusters. As discussed above, identifying the nearest cluster(s) may include determining a distance (e.g., a Euclidean distance, cosine distance, etc.) between the characteristic vector and the representative vector (e.g., centroid or mean vector) for each of the clusters to identify which cluster(s) the characteristic vector is nearest. Identifying the nearest cluster(s) may alternatively (or in addition to) include computing a distance between the characteristic vector and the distribution of characteristic vectors in each cluster (e.g., a Mahalanobis distance). According to some embodiments, multiple nearest clusters are identified by using multiple respective distance measures. It should be appreciated that there are numerous suitable ways in which a characteristic vector may be compared to the cluster model to obtain information about the corresponding text region (e.g., to assess the diagnostic relevance of the text region undergoing evaluation), as the aspects are not limited for use with any particular technique for comparing a characteristic vector to a cluster model.

In act 2240, it is determined whether to exclude the text region from further consideration when suggesting medical billing codes to a user based on the comparison of the characteristic vector to the cluster model. For example, if the nearest cluster is labeled as predominantly, primarily and/or substantially false positive (e.g., the cluster has a sufficiently high percentage of false positive characteristic vectors, a sufficiently high ratio of false positive to true positive vectors, etc.), the text region may be excluded because of the high likelihood that it will generate false positive medical billing code suggestions. According to some embodiments, a text region may be excluded only if the percentage of false positive characteristic vectors in the cluster is significant (e.g., above 80%, above 90%, above 95%, above 98%, etc.) to prevent exclusion of text regions that could produce true positive medical billing code suggestions. That is, according to some embodiments, it may be preferable to err on the side of producing some false positive medical billing code suggestions than to risk suppressing true positive medical billing code suggestions. As discussed above, each cluster may be labeled as a false positive cluster or a true positive cluster based upon one or more of the above described criteria to simplify the comparison in some instances, and in accordance with some embodiments.

According to some embodiments, multiple nearest clusters may be identified and evaluated when determining whether to exclude a text region. For example, if the nearest cluster is inconclusive (e.g., near one or more threshold values), the second (or third) nearest cluster may be evaluated to provide a more definitive answer. As another example, the nearest j clusters may be averaged (e.g., the percentages of false positives may be average, ratios combined, etc.) when determining whether a text region should be excluded. When evaluating multiple nearest clusters, the size of the cluster (i.e., how many characteristic vectors from the training data are cluster members) may be used to weight the significance of the cluster in the evaluation. For example, if a nearest cluster has only a small number of member characteristic vectors and the second nearest cluster has a significantly larger number of member characteristic vectors, the second nearest cluster may be accorded more significance, and vice versa. When evaluating multiple nearest clusters, the relative distances may be used to weight the significance of the respective cluster accordingly. For example, if the second nearest cluster is only slightly further from the characteristic vector than the nearest cluster, it may be given similar weight when evaluating whether to exclude the text region. On the other hand, if the second nearest cluster is significantly further away, it may be accorded proportionately less weight (or may be ignored altogether).

It should be appreciated that any number of clusters may be evaluated and any suitable criteria may be employed to determine whether to exclude the text region from further consideration based on the evaluation of one or more nearest clusters (e.g., based on the labels of the j nearest clusters), as the aspects are not limited in this respect. Accordingly, a variety of ways of comparing a characteristic vector to a cluster model (e.g., act 2230) and evaluating whether a text region should be excluded from further consideration when suggesting medical billing codes to a user based on the comparison (e.g., act 2240) may be suitable and the aspects are not limited for use to any particular technique or techniques for doing so. Method 2200 may be repeated for each text region in a text being processed by a CAC system to exclude any text regions that are deemed sufficiently likely to produce false positive medical billing code suggestions to the user.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of embodiments of the present invention comprises at least one computer-readable storage medium (i.e., a tangible, non-transitory computer-readable medium, such as a computer memory, a floppy disk, a compact disk, a magnetic tape, or other tangible, non-transitory computer-readable medium) encoded with a computer program (i.e., a plurality of instructions), which, when executed on one or more processors, performs above-discussed functions of embodiments of the present invention. The computer-readable storage medium can be transportable such that the program stored thereon can be loaded onto any computer resource to implement aspects of the present invention discussed herein. In addition, it should be appreciated that the reference to a computer program which, when executed, performs any of the above-discussed functions, is not limited to an application program running on a host computer. Rather, the term "computer program" is used herein in a generic sense to reference any type of computer code (e.g., software or microcode) that can be employed to program one or more processors to implement above-discussed aspects of the present invention.

The phraseology and terminology used herein is for the purpose of description and should not be regarded as limiting. The use of "including," "comprising," "having," "containing", "involving", and variations thereof, is meant to encompass the items listed thereafter and additional items. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements from each other.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. A system for automatically processing text comprising information regarding a patient encounter to assign medical codes to the text, the system comprising:
   at least one storage medium storing processor-executable instructions; and
   at least one processor configured to execute the processor-executable instructions to:
      assign one or more medical billing codes to a first plurality of facts extracted from first text, wherein the first plurality of facts is extracted from the first text by applying a natural language understanding engine to the first text;
      receive user feedback regarding whether the one or more medical codes were correctly or incorrectly assigned to the first text;
      generate training data to train a model used to identify text regions that should not be processed for medical code assignment, the training data including information regarding at least one text region of the first text for which the user feedback regarding whether the one or more medical codes were correctly or incorrectly assigned was received;
      parse second text into a plurality of text regions;
      identify at least one text region of the plurality of text regions of the second text that should not be processed for medical code assignment, wherein identifying the at least one text region of the plurality of text regions of the second text that should not be processed for medical code assignment comprises:
         determining, using the model trained based on the training data including information regarding the at least one text region of the first text for which the user feedback regarding whether the one or more medical codes were correctly or incorrectly assigned was received, whether the at least one text region of the plurality of text regions of the second text should not be processed for medical code assignment; and
      process each text region of the plurality of text regions of the second text, except for the identified at least one text region of the plurality of text regions of the second text, to assign one or more medical codes to the second text based, at least in part, on one or more of a second plurality of facts extracted from the processed text regions by applying the natural language understanding engine to the second text.

2. The system of claim 1, wherein the evaluating determining comprises determining using the model trained based on the training data including information regarding which of the one or more medical codes assigned to the first text were accepted by at least one user and/or which of the one or more medical codes assigned to the first text were not accepted by the at least one user.

3. The system of claim 1, wherein the at least one processor is configured to compare each of the plurality of text regions to the model to assess a likelihood that the each respective text region would be incorrectly assigned one or more medical codes.

4. The system of claim 3, wherein the model comprises:
a language embedding model configured to produce a characteristic vector output in response to receiving a text region as input; and
a cluster model comprising a plurality of labeled clusters of characteristic vectors output by the language embedding model in response to receiving text regions of the training data as input.

5. The system of claim 4, wherein the cluster model comprises more than one hundred clusters.

6. The system of claim 4, wherein the at least one processor is configured to input each of the plurality of text regions to the language embedding model to produce a respective plurality of characteristic vectors and to compare each of the plurality of characteristic vectors with each of the plurality of labeled clusters of the cluster model.

7. The system of claim 6, wherein the at least one processor is configured to determine which of the plurality of labeled clusters each of the plurality of characteristic vectors is nearest according to at least one distance measure.

8. The system of claim 7, wherein a nearest j clusters is identified for each of the plurality of characteristic vectors.

9. The system of claim 8, wherein j=1.

10. The system of claim 8, wherein j>1.

11. The system of claim 7, wherein the at least one processor is configured to identify a text region that should not be processed for medical code assignment if the nearest cluster to the respective characteristic vector represents a false positive cluster according to a first criteria.

12. The system of claim 11, wherein the first criteria includes a percentage of member characteristic vectors of a nearest cluster corresponding to false positive text regions that exceeds a percentage threshold.

13. The system of claim 11, wherein the first criteria includes a ratio of member characteristic vectors of a nearest cluster corresponding to false positive text regions to member characteristic vectors of the nearest cluster corresponding to true positive text regions that exceeds a ratio threshold.

14. The system of claim 4, wherein the model is trained using feedback received from a specific customer.

15. The system of claim 14, wherein the language embedding model is trained using first training data, and wherein the cluster model is produced using second training data consisting of the feedback from the specific customer.

16. The system of claim 6, wherein the at least one processor is configured to parse the second text into a plurality of paragraphs and to provide each of the plurality of paragraphs to the language embedding model to obtain a characteristic vector for each of the plurality of paragraphs.

17. The system of claim 16, wherein each of the plurality of labeled clusters that meets a first criteria is labeled as a false positive cluster, and wherein the at least one processor is configured to exclude each of the plurality of paragraphs from further consideration when a nearest cluster to the respective paragraph is labeled false positive.

18. A method for automatically processing text comprising information regarding a patient encounter to assign medical codes to the text, the method comprising:
assigning one or more medical billing codes to a first plurality of facts extracted from first text, wherein the first plurality of facts is extracted from the first text by applying a natural language understanding engine to the first text;
receiving user feedback regarding whether the one or more medical codes were correctly or incorrectly assigned to the first text;
generating training data to train a model used to identify text regions that should not be processed for medical code assignment, the training data including information regarding at least one text region of the first text for which the user feedback regarding whether the one or more medical codes were correctly or incorrectly assigned was received;
parsing second text into a plurality of text regions;
identifying at least one text region of the plurality of text regions of the second text that should not be processed for medical code assignment, wherein identifying the at least one text region of the plurality of text regions of the second text that should not be processed for medical code assignment comprises:
determining, using the model trained based on the training data including information regarding the at least one text region of the first text for which the user feedback regarding whether the one or more medical codes were correctly or incorrectly assigned was received, whether each text region of the plurality of text regions of the second text should not be processed for medical code assignment; and
processing each text region of the plurality of text regions of the second text, except for the identified at least one text region of the plurality of text regions of the second text, to assign one or more medical codes to the second text based, at least in part, on one or more of a second plurality of facts extracted from the processed text regions by applying the natural language understanding engine to the second text.

19. At least one computer readable medium storing instructions that, when executed by at least one processor, perform a method of automatically processing text comprising information regarding a patient encounter to assign medical codes to the text, the method comprising:
assigning one or more medical billing codes to a first plurality of facts extracted from first text, wherein the first plurality of facts is extracted from the first text by applying a natural language understanding engine to the first text;
receiving user feedback regarding whether the one or more medical codes were correctly or incorrectly assigned to the first text;
generating training data to train a model used to identify text regions that should not be processed for medical code assignment, the training data including information regarding at least one text region of the first text for which the user feedback regarding whether the one or more medical codes were correctly or incorrectly assigned was received;
parsing second text into a plurality of text regions;
identifying at least one text region of the plurality of text regions of the second text that should not be processed for medical code assignment, wherein identifying the at least one text region of the plurality of text regions of the second text that should not be processed for medical code assignment comprises:

determining, using the model trained based on the training data including information regarding the at least one text region of the first text for which the user feedback regarding whether the one or more medical codes were correctly or incorrectly assigned was received, whether the at least one text region of the plurality of text regions of the second text should not be processed for medical code assignment; and processing each text region of the plurality of text regions of the second text, except for the identified at least one text region of the plurality of text regions of the second text, to assign one or more medical codes to the second text based, at least in part, on one or more of a second plurality of facts extracted from the processed text regions by applying the natural language understanding engine to the second text.

\* \* \* \* \*